(12) United States Patent
Cha et al.

(10) Patent No.: US 10,562,876 B2
(45) Date of Patent: *Feb. 18, 2020

(54) ORGANIC COMPOUNDS FOR ORGANIC LIGHT-EMITTING DIODE AND ORGANIC LIGHT-EMITTING DIODE INCLUDING THE SAME

(71) Applicant: SFC CO., LTD., Cheongju-si (KR)

(72) Inventors: Soon-Wook Cha, Goyang-si (KR); Seok-Bae Park, Geumsan-gun (KR); Sang-woo Park, Seoul (KR); Yoona Shin, Seoul (KR); Hee-Dae Kim, Miryang-si (KR)

(73) Assignee: SFC CO., LTD., Cheongju-si (KR)

( * ) Notice: Subject to any disclaimer, the term of this patent is extended or adjusted under 35 U.S.C. 154(b) by 210 days.

This patent is subject to a terminal disclaimer.

(21) Appl. No.: 15/542,662

(22) PCT Filed: Jan. 4, 2016

(86) PCT No.: PCT/KR2016/000017
§ 371 (c)(1),
(2) Date: Jul. 11, 2017

(87) PCT Pub. No.: WO2016/117848
PCT Pub. Date: Jul. 28, 2016

(65) Prior Publication Data
US 2018/0009776 A1    Jan. 11, 2018

(30) Foreign Application Priority Data
Jan. 20, 2015 (KR) .................. 10-2015-0009241

(51) Int. Cl.
*H01L 51/50* (2006.01)
*C07D 307/91* (2006.01)
(Continued)

(52) U.S. Cl.
CPC .......... *C07D 307/91* (2013.01); *C07B 59/002* (2013.01); *C07C 13/567* (2013.01);
(Continued)

(58) Field of Classification Search
None
See application file for complete search history.

(56) References Cited

U.S. PATENT DOCUMENTS

2012/0056165 A1 † 3/2012 Kawamura

FOREIGN PATENT DOCUMENTS

JP    2005-314239 A   † 11/2005
JP    2005314239 A      11/2005
(Continued)

OTHER PUBLICATIONS

International Search Report of PCT/KR2016/000017, dated Apr. 15, 2016, English translation.
(Continued)

*Primary Examiner* — Gregory D Clark
(74) *Attorney, Agent, or Firm* — STIP Law Group, LLC

(57) ABSTRACT

The present invention relates to a compound for organic light-emitting diodes that can operate organic light-emitting diodes at a low driving voltage and an organic light-emitting diode comprising the same and, more particularly, to a compound for use as a fluorescent host in organic light-emitting diodes, which can bring about excellent diode properties by operating organic light-emitting diodes at a low driving voltage, and an organic light-emitting diode comprising the same.

9 Claims, 1 Drawing Sheet

(51) Int. Cl.
*C09K 11/06* (2006.01)
*C07C 13/567* (2006.01)
*H01L 51/00* (2006.01)
*C07B 59/00* (2006.01)

(52) U.S. Cl.
CPC .......... *C09K 11/06* (2013.01); *H01L 51/0052* (2013.01); *H01L 51/0073* (2013.01); *C07B 2200/05* (2013.01); *C07C 2603/18* (2017.05); *C09K 2211/1007* (2013.01); *C09K 2211/1011* (2013.01); *C09K 2211/1018* (2013.01); *C09K 2211/1029* (2013.01); *C09K 2211/1088* (2013.01); *C09K 2211/1092* (2013.01); *H01L 51/006* (2013.01); *H01L 51/0054* (2013.01); *H01L 51/0072* (2013.01); *H01L 51/0077* (2013.01); *H01L 51/5012* (2013.01)

(56) References Cited

FOREIGN PATENT DOCUMENTS

| | | | |
|---|---|---|---|
| JP | 5608978 | A | 4/2011 |
| JP | 2013216884 | A | 10/2013 |
| KR | 1020090086015 | A | 8/2000 |
| KR | 100910150 | B1 | 8/2009 |
| KR | 1020100017136 | A | 2/2010 |
| KR | 10-2012-0135501 | * | 12/2012 ............. H01L 51/50 |
| KR | 10-2012-0135501 | A † | 12/2012 |
| KR | 1020120135501 | A | 12/2012 |
| WO | WO2008143229 | A1 | 11/2008 |
| WO | WO2009063846 | A1 | 5/2009 |
| WO | WO2009069537 | S1 | 6/2009 |
| WO | WO2009116628 | A1 | 9/2009 |
| WO | WO2009154207 | A1 | 12/2009 |
| WO | WO1010010924 | A1 | 1/2010 |
| WO | WO2010010924 | A1 | 1/2010 |
| WO | WO2010052885 | A1 | 5/2010 |
| WO | WO2010122810 | A1 | 10/2010 |
| WO | WO2009069537 | A1 | 4/2011 |
| WO | WO2009154207 | A1 | 12/2011 |
| WO | WO2011074253 | A1 | 4/2013 |
| WO | WO2014014307 | A1 | 1/2014 |

OTHER PUBLICATIONS

Office Action from China National Intellectual Property Administration of 2016800047433, dated Jan. 3, 2016.
Office Action from Korean Intellectual Property Office of 10-2015-0009241, dated Sep. 10, 2018.

\* cited by examiner
† cited by third party

| 80 |
|----|
| 70 |
| 60 |
| 50 |
| 40 |
| 30 |
| 20 |
| 10 |

ORGANIC COMPOUNDS FOR ORGANIC LIGHT-EMITTING DIODE AND ORGANIC LIGHT-EMITTING DIODE INCLUDING THE SAME

CROSS-REFERENCE TO RELATED APPLICATIONS

This application is the U.S. National Phase under 35 U.S.C. § 371 of International Application No. PCT/KR2016/000017 filed on Jan. 4, 2016, which in turn claims the benefit of Korean Application No. 10-2015-0009241, filed on Jan. 20, 2015, the disclosures of which are incorporated by reference into the present application.

TECHNICAL FIELD

The present disclosure relates to a compound for organic light-emitting diodes that can operate organic light-emitting diodes at a low driving voltage and an organic light-emitting diode comprising the same and, more particularly, to a compound for use as a fluorescent host in organic light-emitting diodes, which can bring about excellent diode properties by operating organic light-emitting diodes at a low driving voltage and an organic light-emitting diode comprising the same.

BACKGROUND ART

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the illumination field as well as the full-color display field.

In general, the term "organic light-emitting phenomenon" refers to a phenomenon in which electrical energy is converted to light energy by means of an organic material. An OLED using the organic light-emitting phenomenon has a structure usually comprising an anode, a cathode, and an organic material layer interposed therebetween. In this regard, the organic material layer may be, for the most part, of a multilayer structure consisting of different materials, for example, a hole injecting layer, a hole transport layer, a light-emitting layer, an electron transport layer, and an electron injecting layer, in order to improve the efficiency and stability of the organic light-emitting diode (OLED). In the organic light-emitting diode having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively. Further, luminescent materials may be divided according to color into blue, green, and red light-emitting materials. Furthermore, yellow and reddish yellow light-emitting materials have been developed in order to achieve more natural colors.

Meanwhile, when a single material is employed as the luminescent material, intermolecular actions cause the wavelength of maximum luminescence to shift toward a longer wavelength, decreasing color purity or attenuating light with consequent reduction in the efficiency of the diode. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to related arts pertaining to host compounds in the light-emitting layer, reference may be made to Korean Patent No. 10-0910150 (Aug. 3, 2009), which discloses an OLED comprising a luminescent medium layer containing a compound in which an anthracene structure has a heterocyclic ring as a substituent at a terminal position thereof, and Japanese Patent No. 5608978 (Oct. 22, 2014), which describes on OLED comprising a luminescent medium layer containing an anthracene derivative in which an anthracene moiety has a dibenzofuran moiety as a substituent at a terminal position thereof.

Despite a variety of kinds of compounds prepared for use in luminescent media layers including the related art, there is still the continued need to develop organic layer materials capable of driving OLEDs at a lower voltage.

RELATED ART DOCUMENT

Korean Patent No. 10-0910150 (Aug. 3, 2009)

Japanese Patent No. 5608978 (Oct. 22, 2014)

DETAILED DESCRIPTION OF THE INVENTION

Technical Problem

Accordingly, a purpose of the present disclosure is to provide a compound for use in organic light-emitting layers which allows OLEDs to be driven at a low voltage.

Another purpose of the present disclosure is to provide an OLED comprising the compound.

Technical Solution

In order to accomplish one purpose thereof, the present disclosure provides an organic luminescent compound represented by the following Chemical Formula A:

[Chemical Formula A]

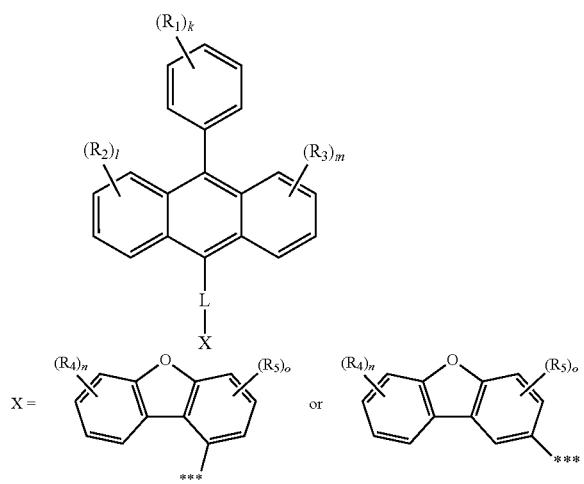

wherein,

R1 to R5 may be the same or different and are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxyl of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxyl, a selenium, a tellurium, an amide, an ether, and an ester, wherein each of unsubstituted carbon atoms of R1 to R5 is bound with a hydrogen atom or a deuterium atom, linker L is a single bond, or a substituted or unsubstituted arylene of 6 to 60 carbon atoms;

k is an integer of 1 to 5, l to n may be the same or different and are each independently an integer of 1 to 4, o is an integer of 1 to 3, with the proviso that when k to o are each an integer of 2 or greater, corresponding R1's to R5's are may be individually the same or different, and "***" of X denotes a bonding site to be linked to linker L.

The other purpose of the present disclosure may be accomplished by providing an OLED comprising a first electrode; a second electrode facing the first electrode; and an organic layer interposed therebetween, wherein the organic layer contains at least one of the organic luminescent compounds of the present disclosure.

Advantageous Effect

According to the present disclosure, the organic luminescent compound represented by Chemical Formula A exhibits the outstanding property of allowing OLEDs to be operated at lower voltages, compared to conventional organic luminescent compounds.

BRIEF DESCRIPTION OF THE DRAWINGS

FIG. 1 is a schematic diagram of an OLED according to some embodiments of the present disclosure.

MODE FOR CARRYING OUT THE INVENTION

Below, a detailed description is given of the present disclosure.

The present disclosure addresses a novel aromatic organic luminescent compound represented by the following Chemical Formula A:

[Chemical Formula A]

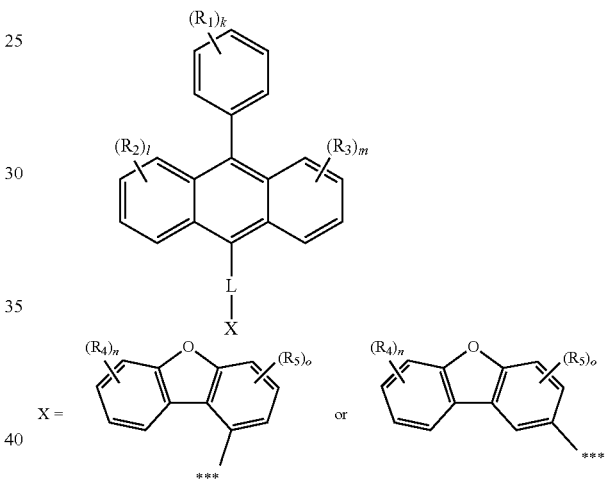

wherein,

R1 to R5 may be the same or different and are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxyl of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of 1 to 30 carbon atoms, a carbonyl, a phosphoryl, an amino, a thiol, a hydroxyl, a selenium, a tellurium, an amide, an ether, and an ester, wherein each of unsubstituted carbon atoms of R1 to R5 is bound with a hydrogen atom or a deuterium atom, linker L is a single bond, or a substituted or unsubstituted arylene of 6 to 60 carbon atoms;

k is an integer of 1 to 5, l to n may be the same or different and are each independently an integer of 1 to 4, o is an integer of 1 to 3, with the proviso that when k to o are each an integer of 2 or greater, corresponding R1's to R5's are may be individually the same or different, and "***" of X denotes a bonding site to be linked to linker L, wherein the term 'substituted' in the expression 'substituted or unsubstituted' used in Chemical Formula A means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Count is taken of the range of the alkyl or aryl moiety in phrases "a substituted or unsubstituted alkyl of 1 to 24 carbon atoms", "a substituted or unsubstituted aryl of 6 to 24 carbon atoms", etc., as used herein. The expression for a number of carbon atoms in "a substituted or unsubstituted alkyl of 1 to 24 carbon atoms", "a substituted or unsubstituted aryl of 6 to 24 carbon atoms" means the total number of carbon atoms in the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of 4 carbon atoms.

As used herein, the term "aryl" as a substituent used in the compounds of the present disclosure refers to an aromatic system consisting of hydrocarbons including one or more rings, and may form an additional ring fused with adjacent substituents attached thereto, if present.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—NH2, —NH(R), or —N(R')(R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 6 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, Si, S, Ge, Se, and Te. In the aromatic system, two or more rings may be fused. One or more hydrogen atoms on the heteroaryl may be substituted with the same substituents as in the aryl.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted with the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted with the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted with the same substituent as in the aryl.

In Chemical Formula A, linking occurs between the carbon atom at position 9 of the anthracene moiety and the carbon atom at position 1 or 2 of either phenyl ring of the substituted or unsubstituted dibenzofuran moiety, as shown in the following Diagram 1, through the linker L.

[Diagram 1]

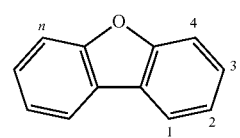

Given a light-emitting layer containing therein the compound represented by Chemical Formula A, an OLED can be driven at a low voltage.

In addition, the linker L in Chemical Formula A may each be a single bond or any one selected from among the following Structural Formulas 1 and 2:

[Structural Formula 1]

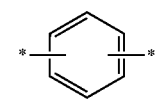

[Structural Formula 2]

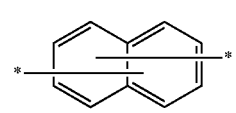

wherein each of the unsubstituted carbon atoms of the aromatic ring moiety is bound with a hydrogen atom or a deuterium atom.

For instance, the linker L may be a single bond or may have a structure represented by the following L1 to L6:

L1

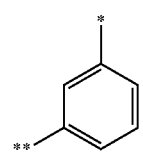

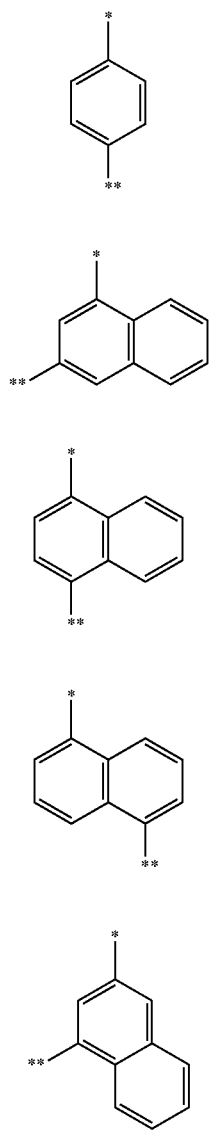

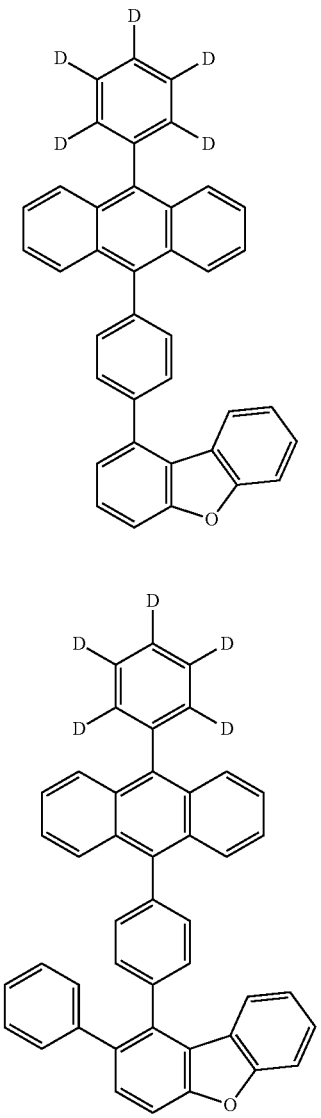

wherein '-*' denotes a bonding site to be linked to the anthracene moiety, and '-**' denotes a bonding site to linked to X.

In addition, at least one of the substituents R1 to R5 in Chemical Formula A may contain a deuterium.

In one embodiment, R1 is a deuterium, and k is 5.

In another embodiment, R2 and/or R3 is a deuterium, and l is an integer of 2 or greater or m is an integer of 2 or greater.

In another embodiment, R2 and R3 are both a deuterium, and l and m are each an integer of 2 or greater.

In another embodiment, R4 and/or R5 is a deuterium, and n is an integer of 2 or greater or o is an integer of 2 or greater.

In another embodiment, R4 and R5 are both a deuterium, and n and o are each an integer of 2 or greater.

Representative of the organic luminescent compounds of the present disclosure is any one selected from among, but not limited to, compounds represented by the following Chemical Formulas 1 to 138.

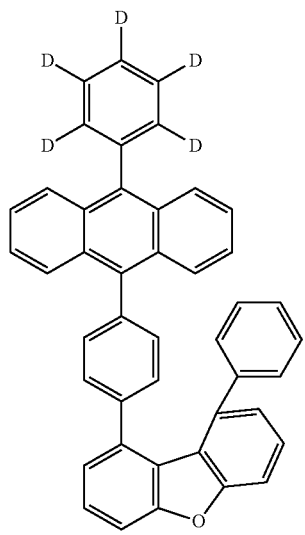

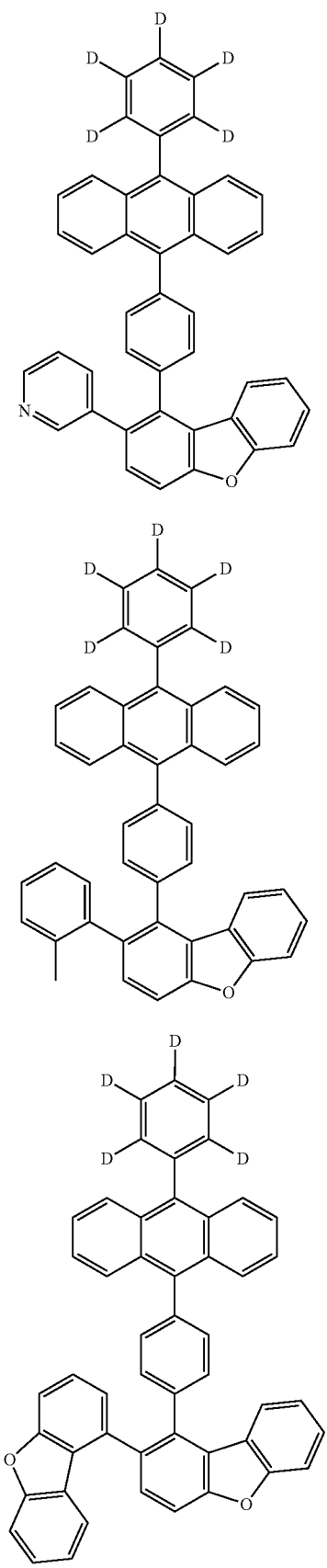
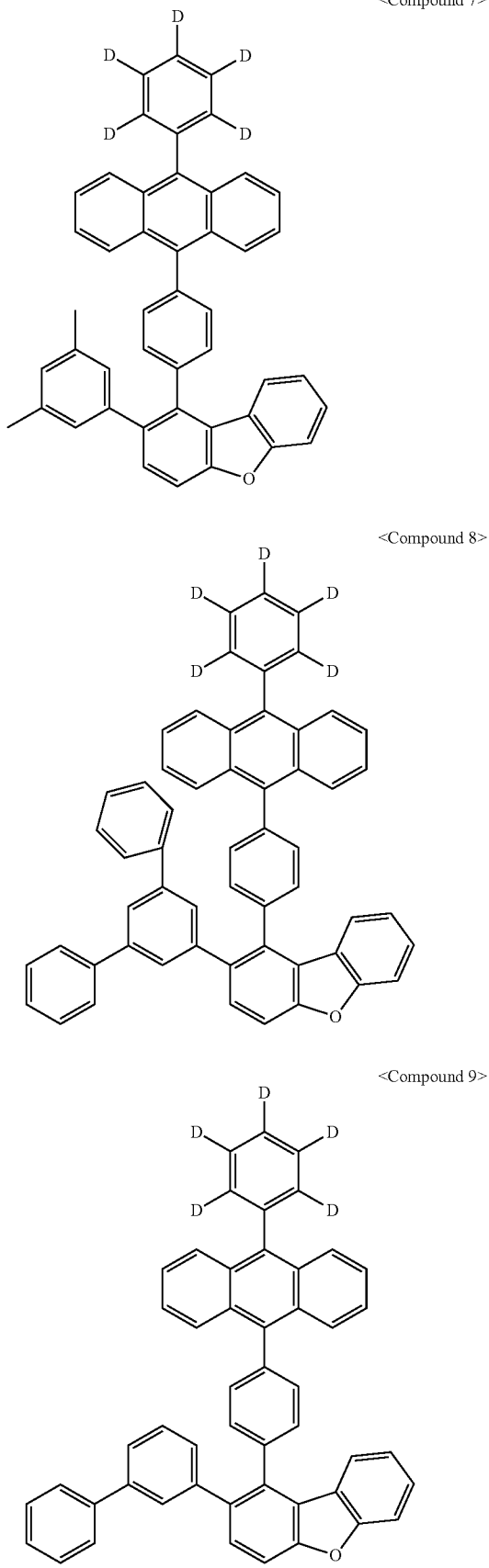

<Compound 10>
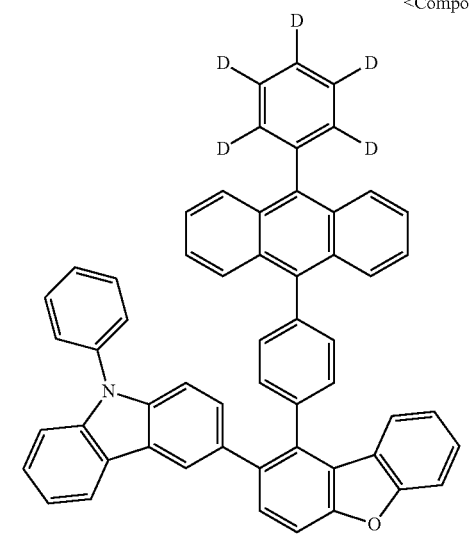
<Compound 11>
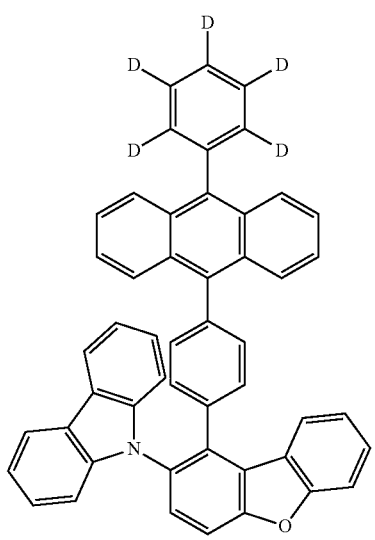
<Compound 12>
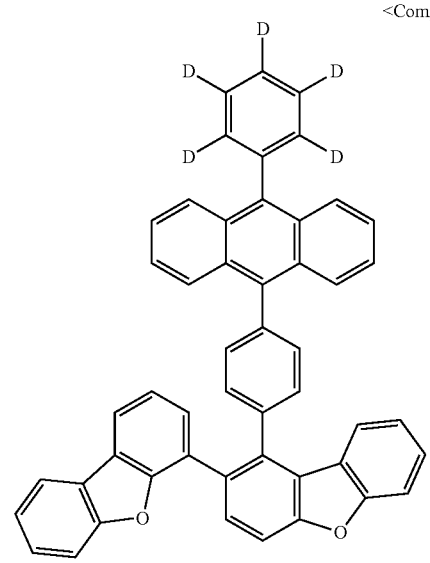
<Compound 13>
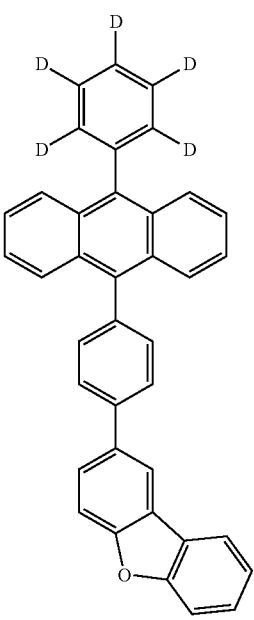
<Compound 14>
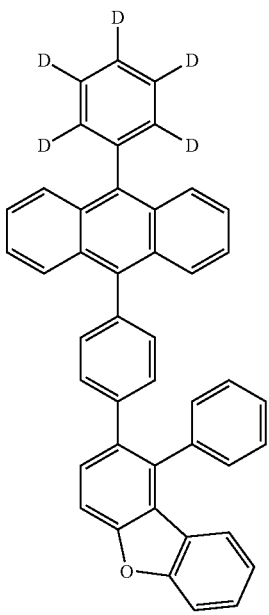

<Compound 15>
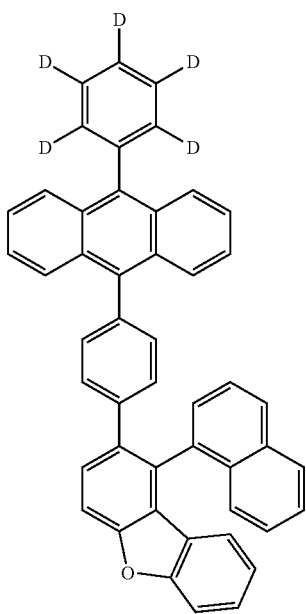
<Compound 16>
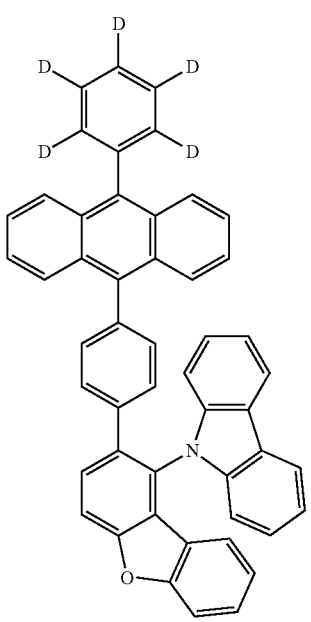
<Compound 17>
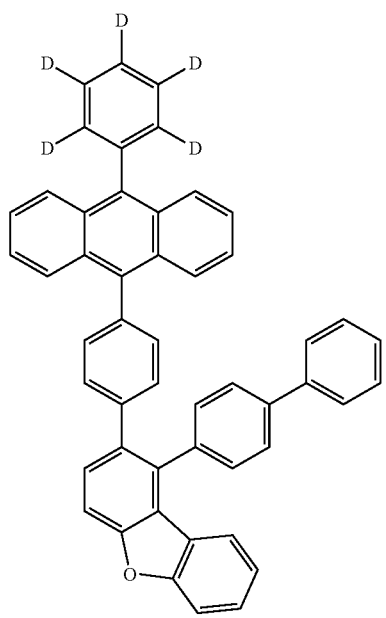
<Compound 18>
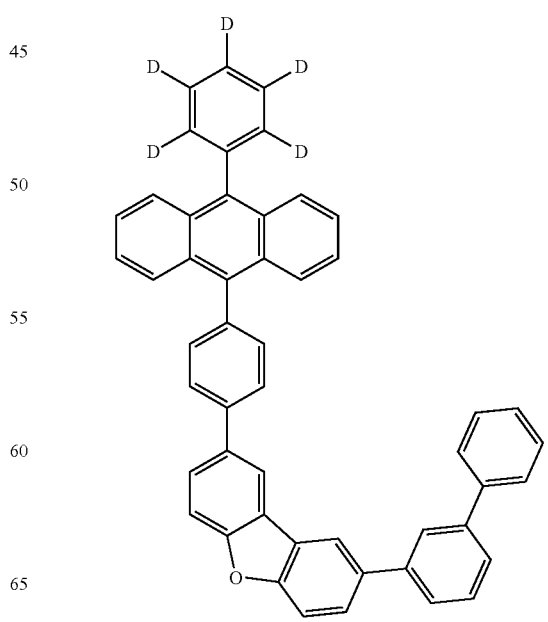

<Compound 19>
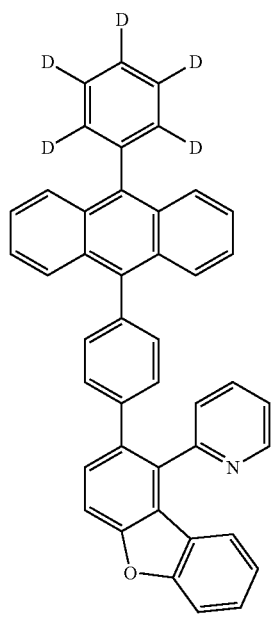
<Compound 20>
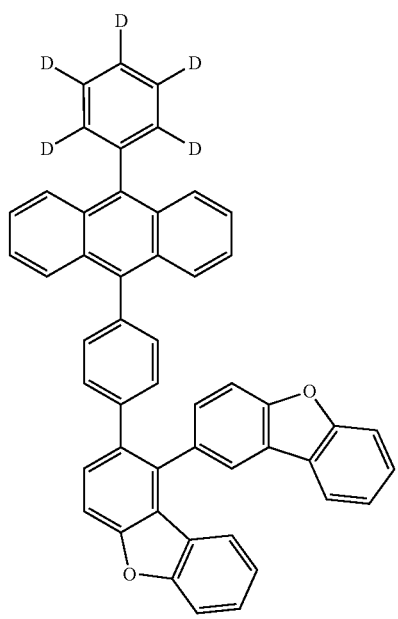
<Compound 21>
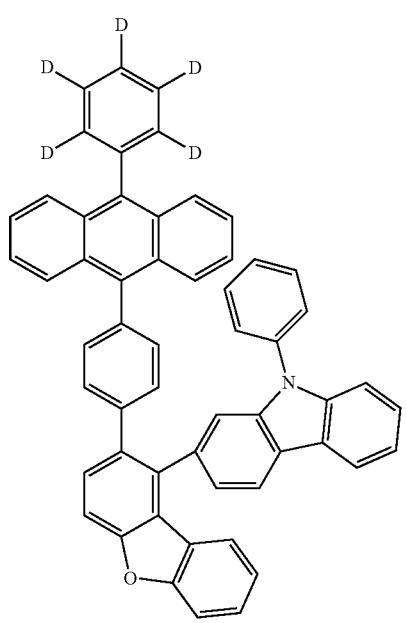
<Compound 22>
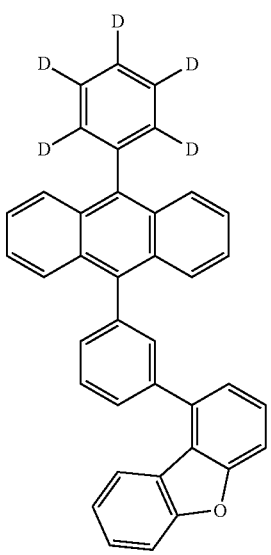

<Compound 23>
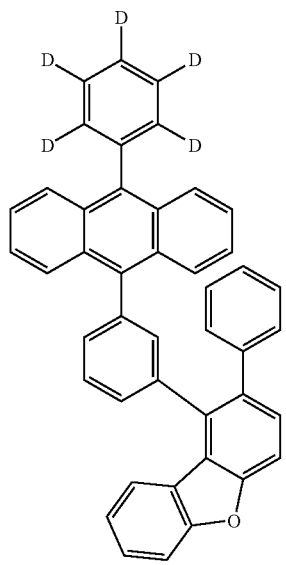
<Compound 25>
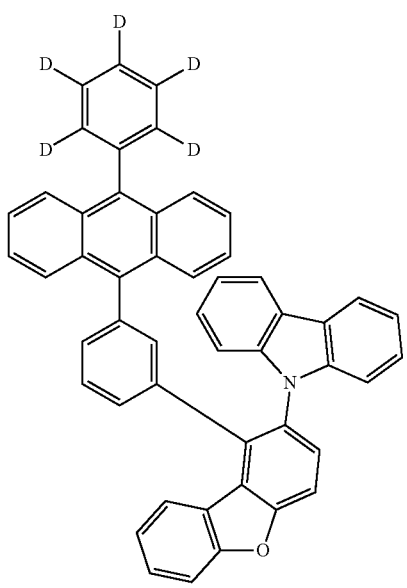
<Compound 24>
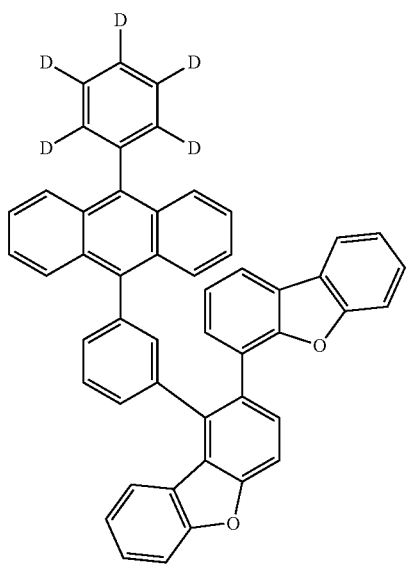
<Compound 26>
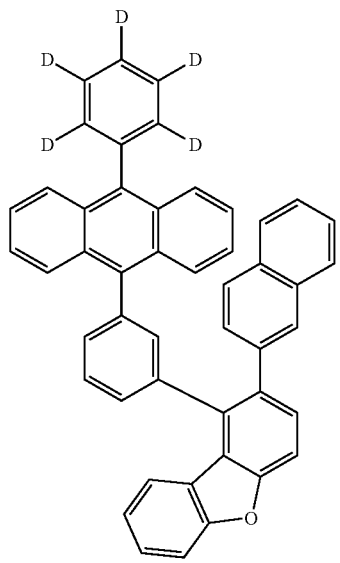

<Compound 27>
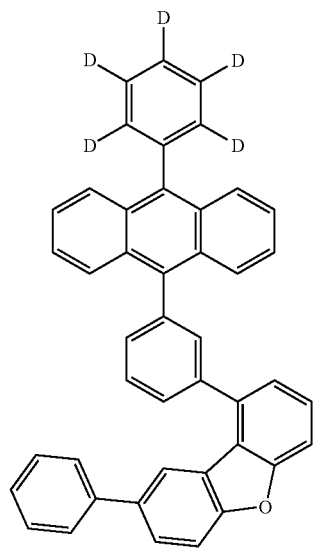
<Compound 28>
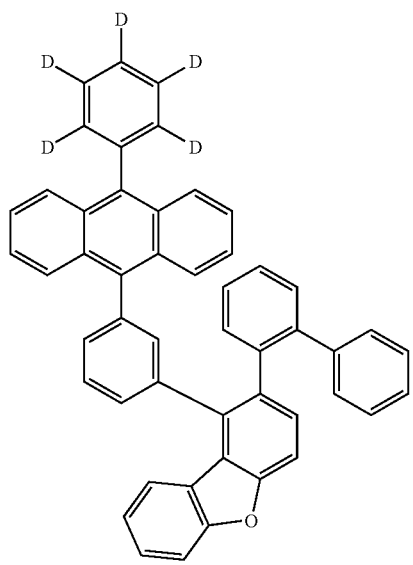
<Compound 29>
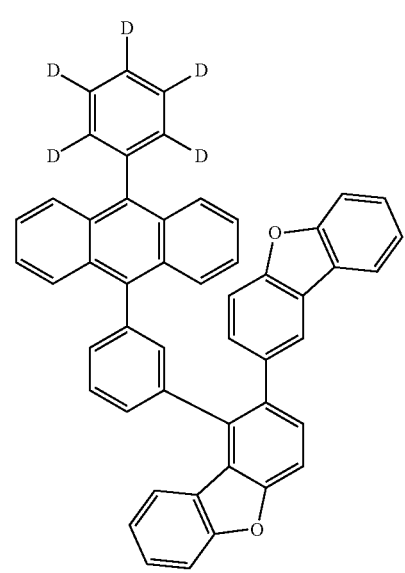
<Compound 30>
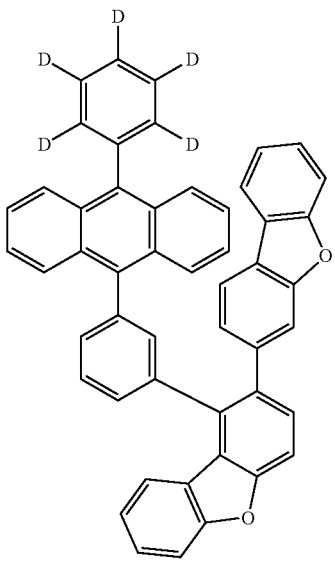
<Compound 31>
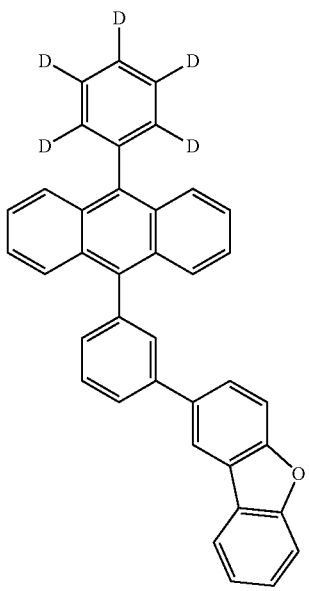

<Compound 32>
<Compound 33>
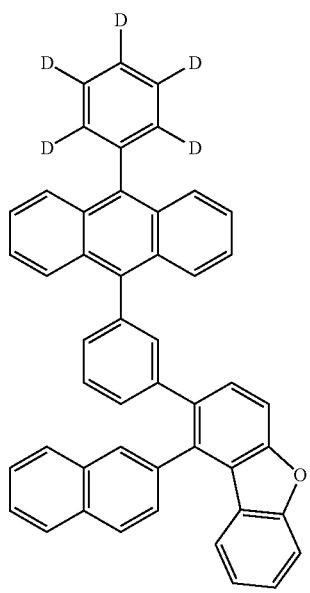
<Compound 34>
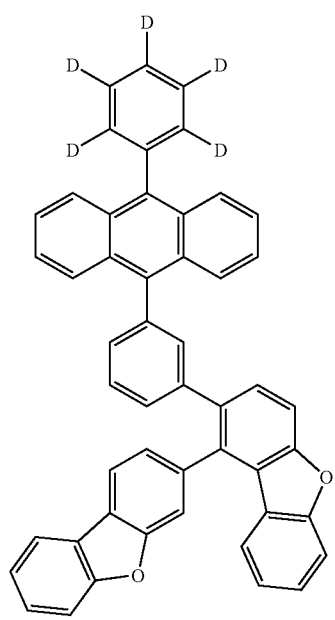
<Compound 35>
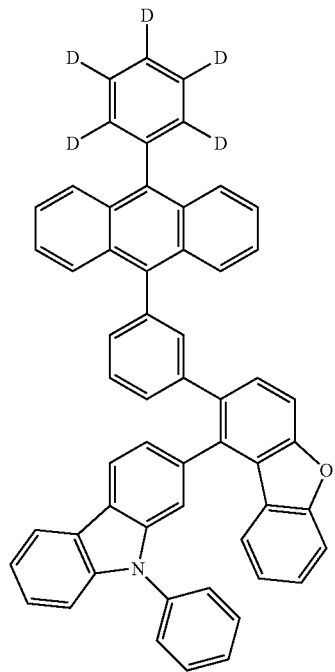

<Compound 36>
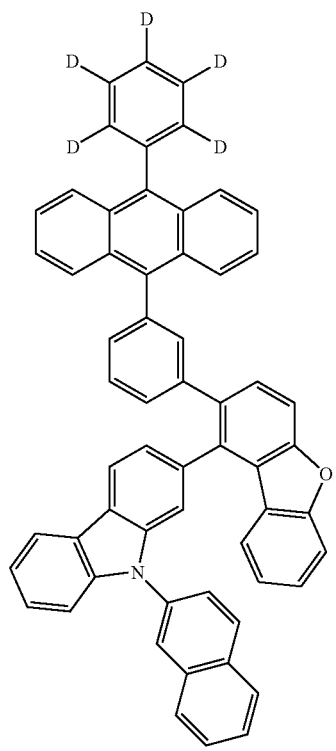
<Compound 38>
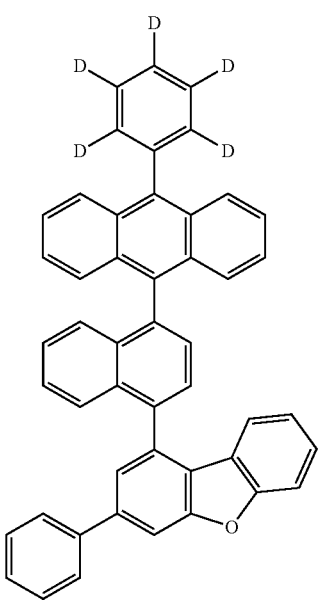
<Compound 37>
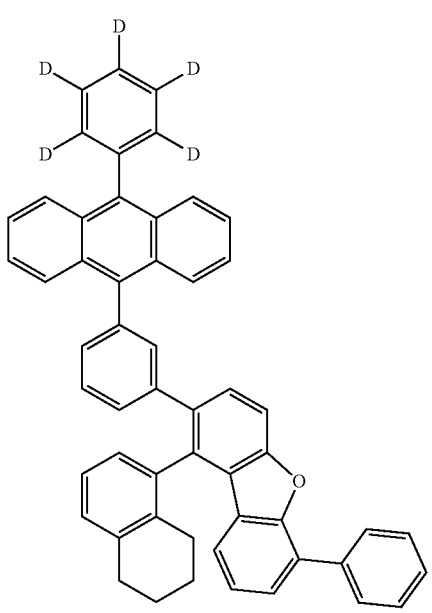
<Compound 39>
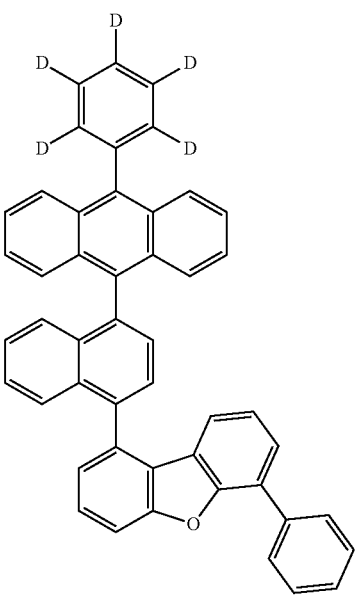

<Compound 40>
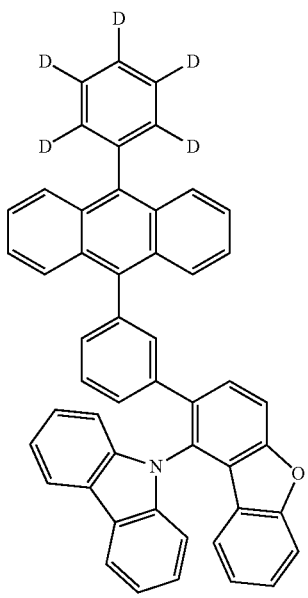
<Compound 41>
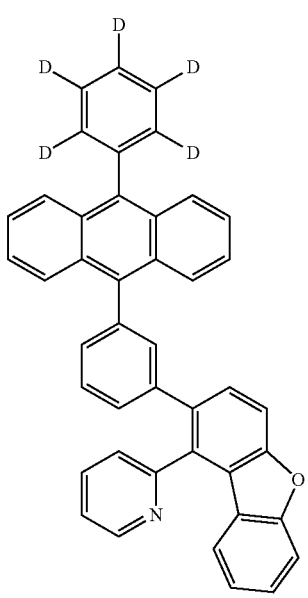
<Compound 42>
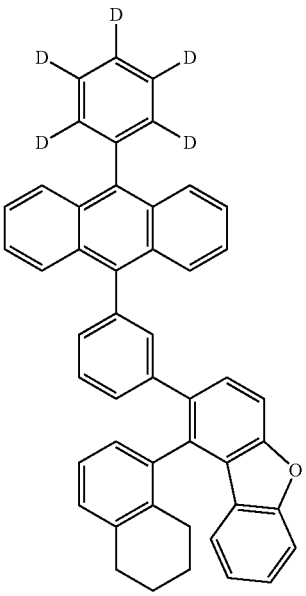
<Compound 43>
(structure)
<Compound 44>
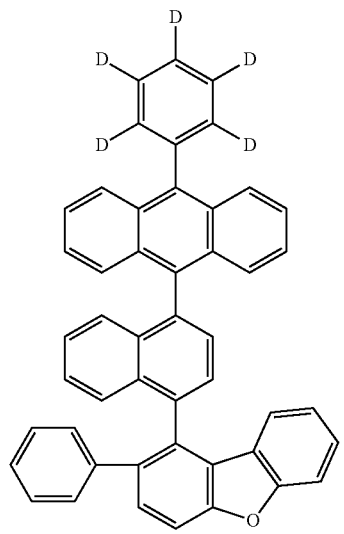

<Compound 45>
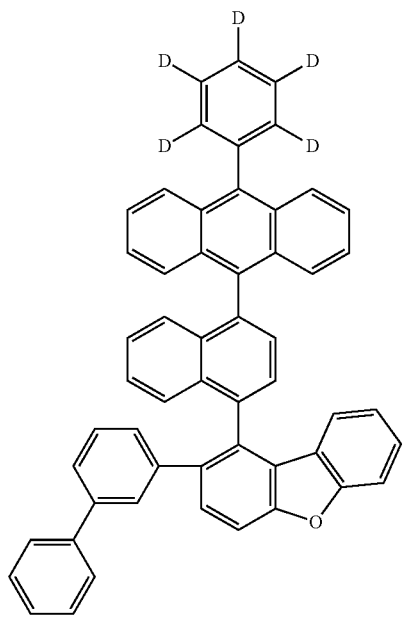
<Compound 46>
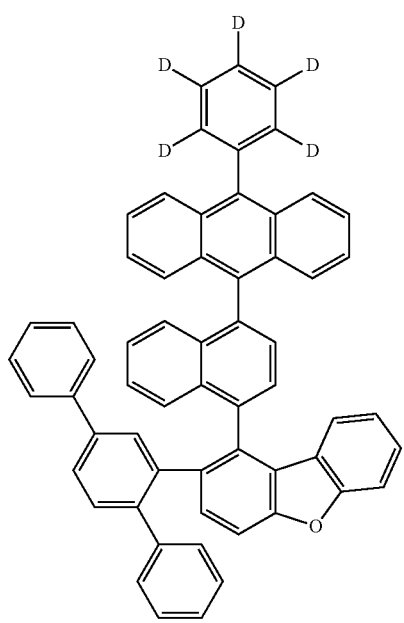
<Compound 47>
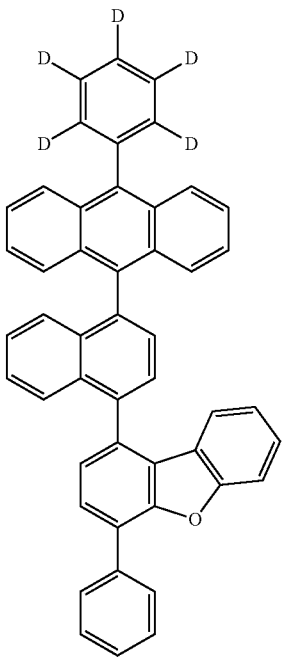
<Compound 48>
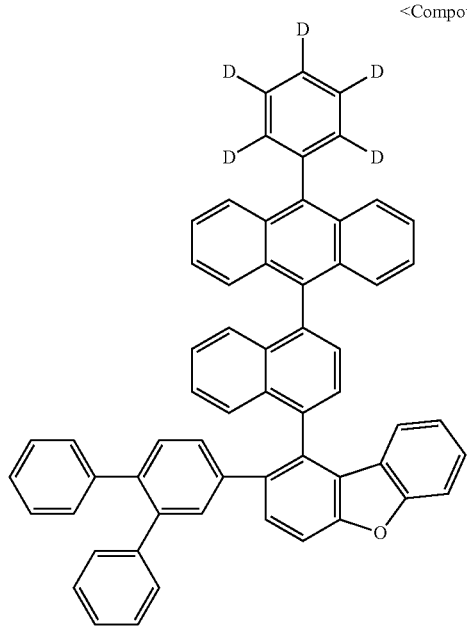

<Compound 49>
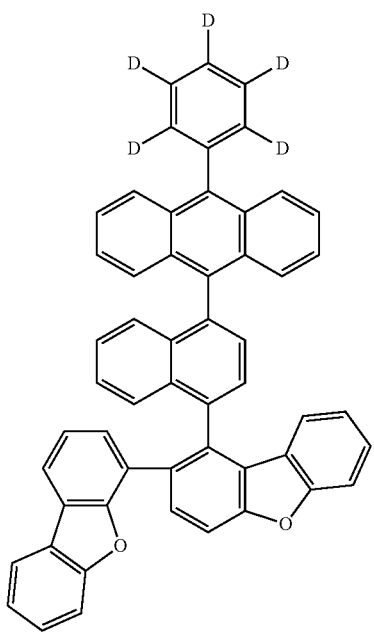
<Compound 50>
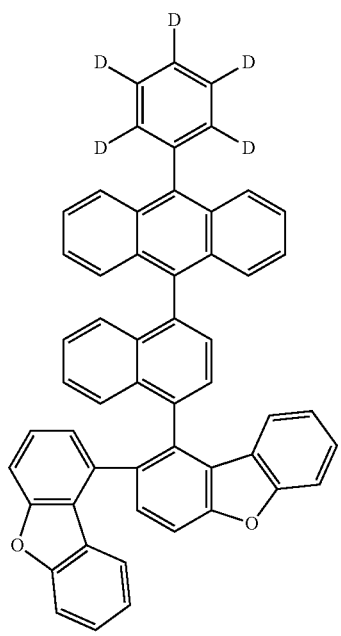
<Compound 51>
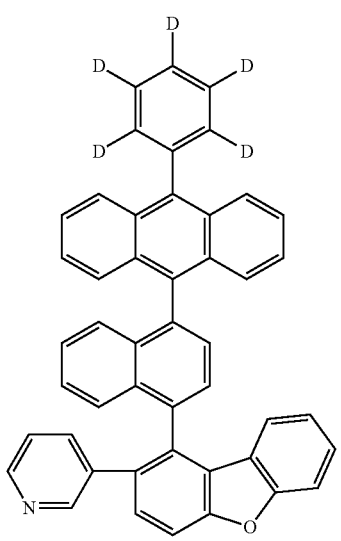
<Compound 52>
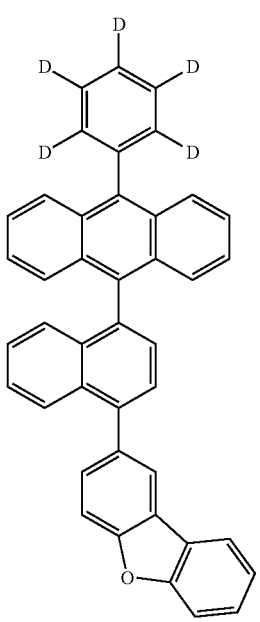

<Compound 53>
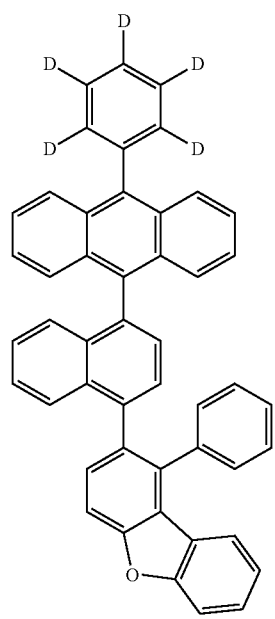
<Compound 54>
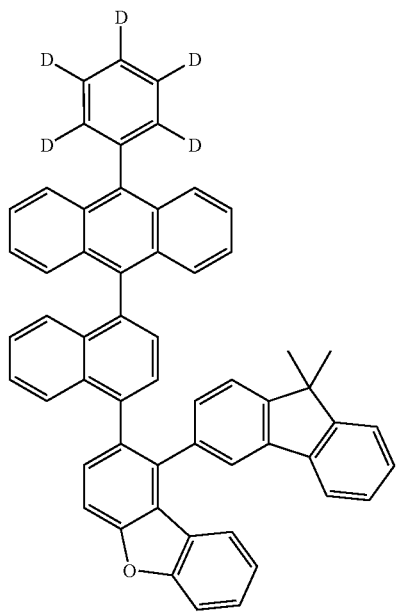
<Compound 55>
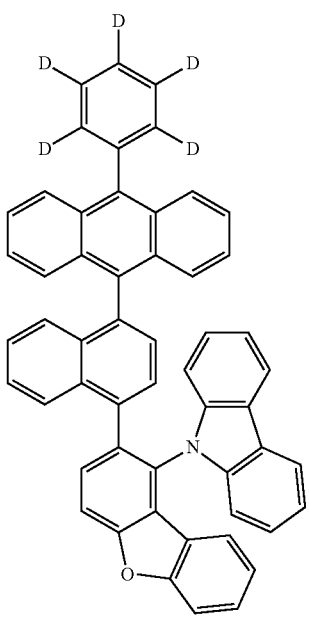
<Compound 56>
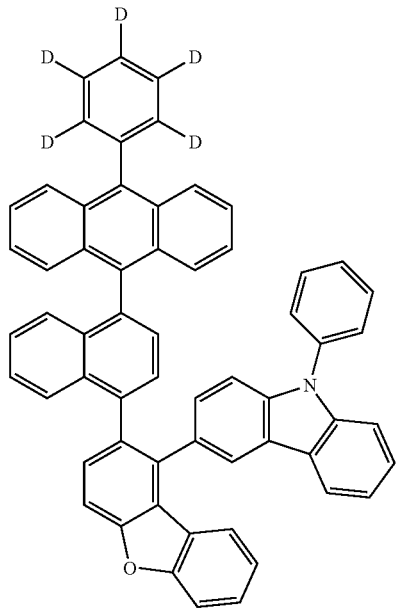

<Compound 57>
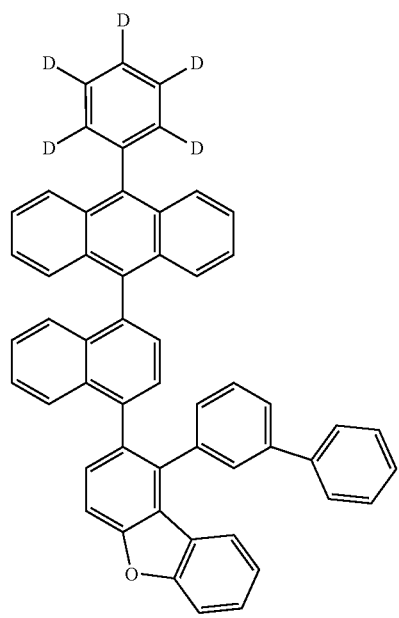
<Compound 58>
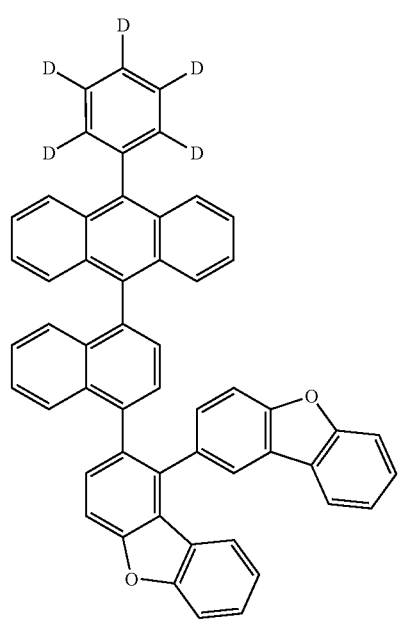
<Compound 59>
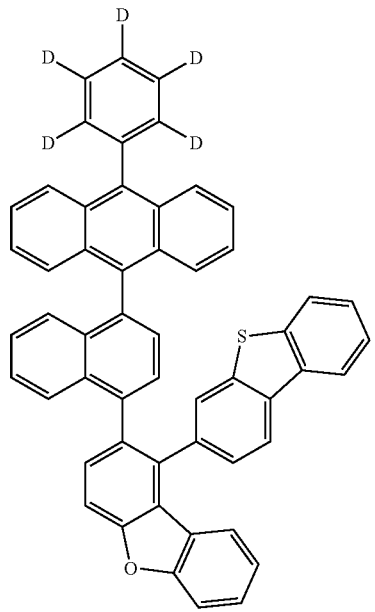
<Compound 60>
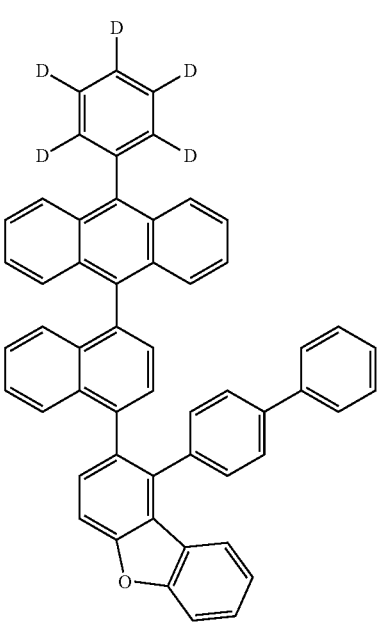

<Compound 61>
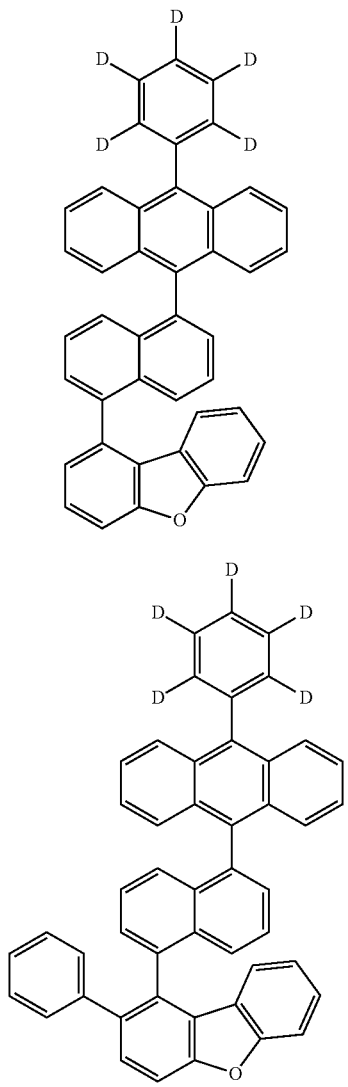
<Compound 62>
<Compound 63>
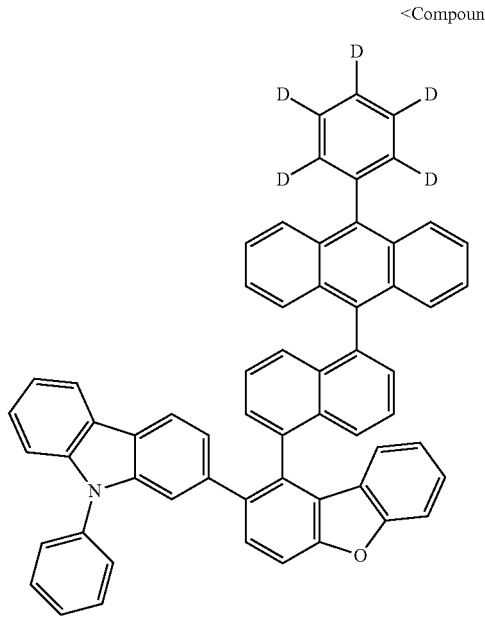
<Compound 64>
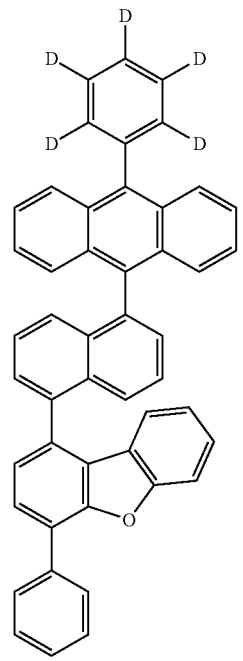
<Compound 65>
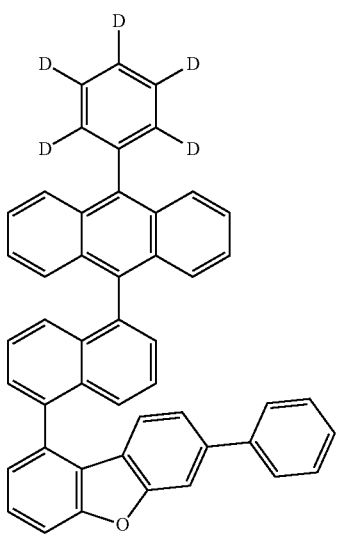

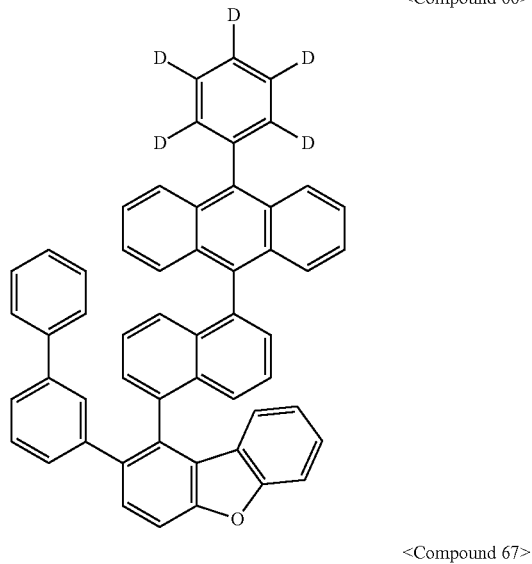
<Compound 66>
<Compound 67>
<Compound 68>
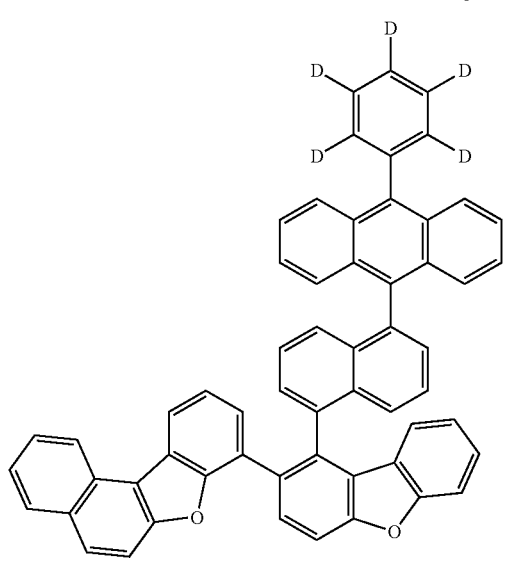
<Compound 69>
<Compound 70>

<Compound 71>
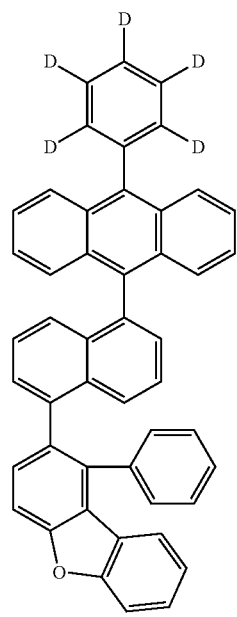
<Compound 72>
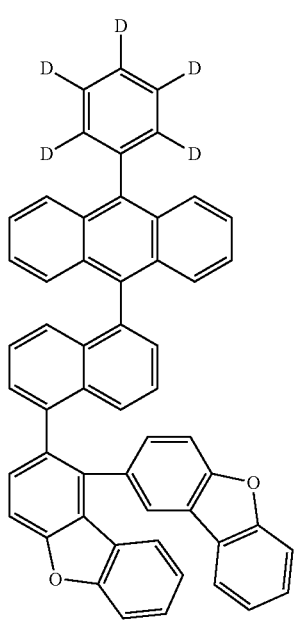
<Compound 73>
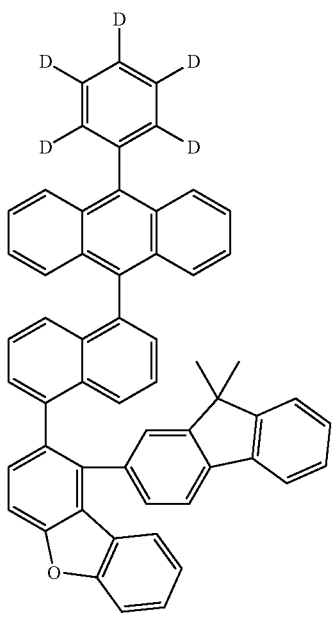
<Compound 74>
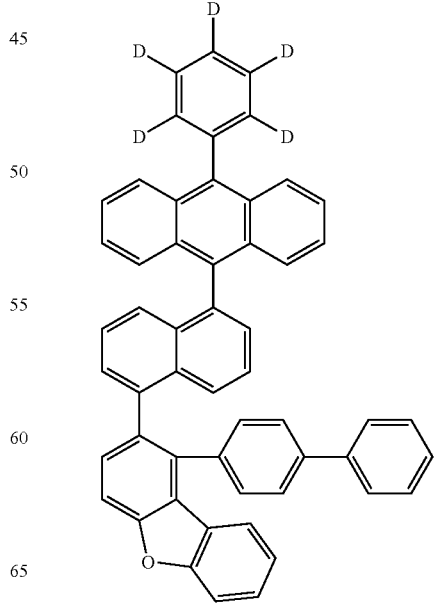

<Compound 75>
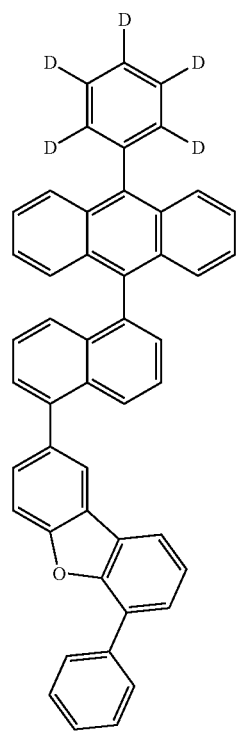
<Compound 77>
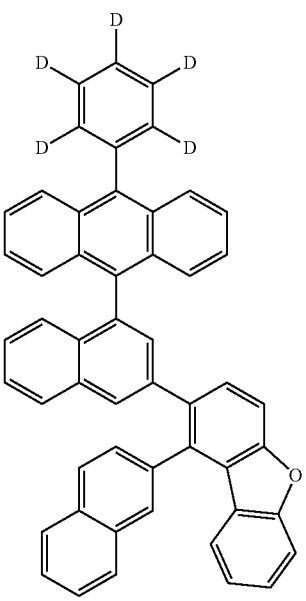
<Compound 76>
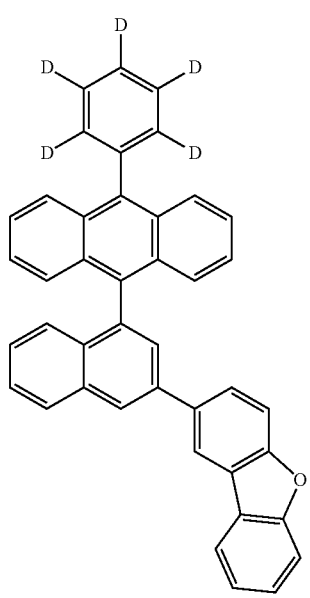
<Compound 78>
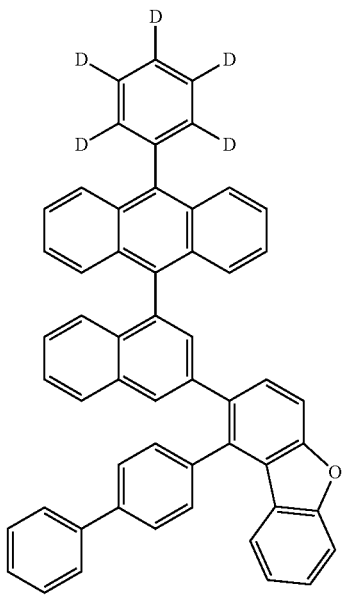

<Compound 79>
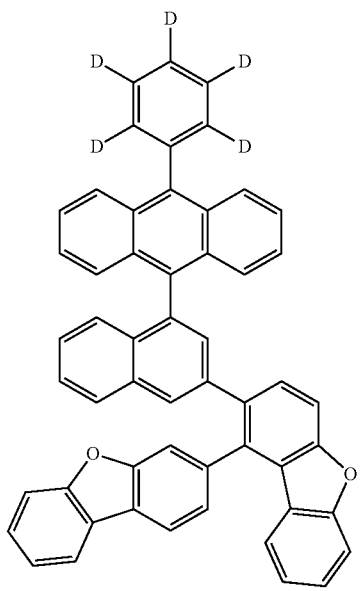
<Compound 81>
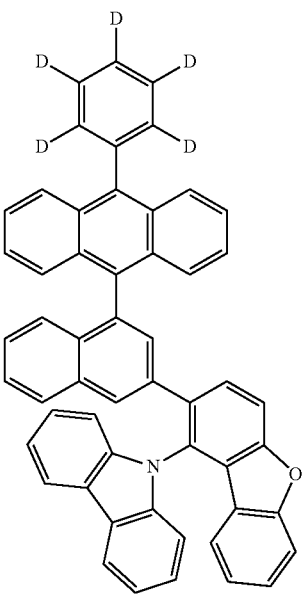
<Compound 80>
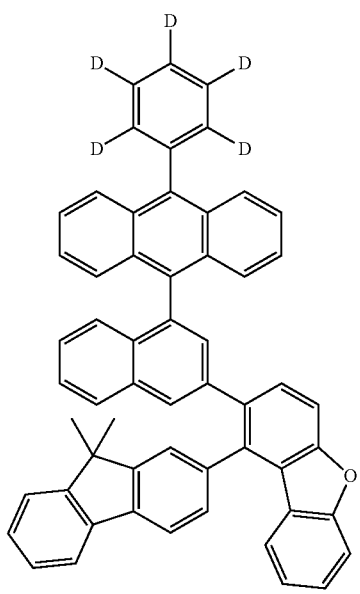
<Compound 82>
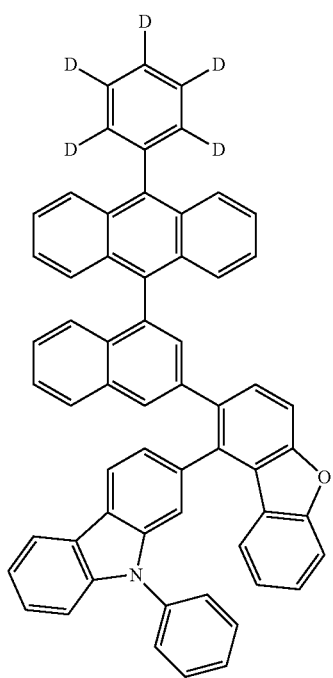

<Compound 83>
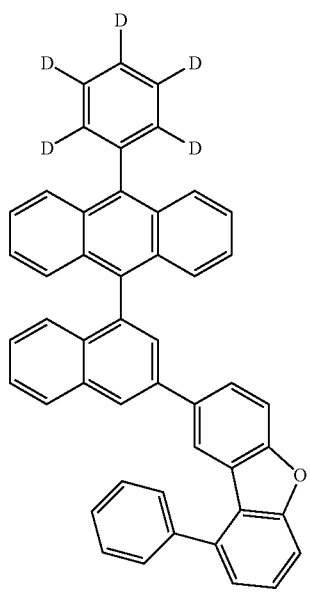
<Compound 84>
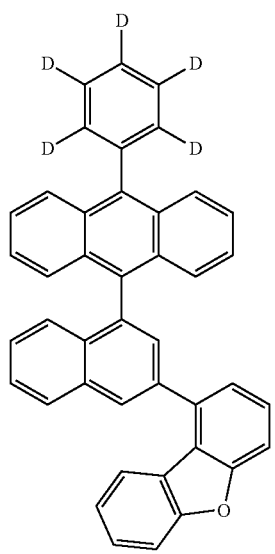
<Compound 85>
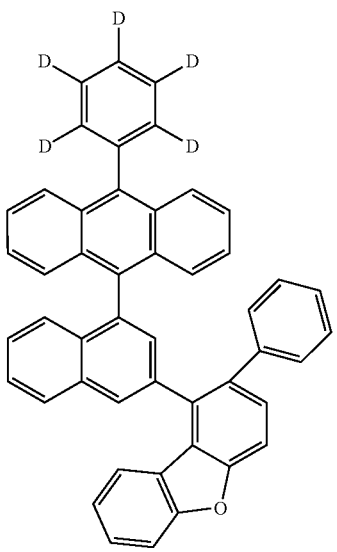
<Compound 86>
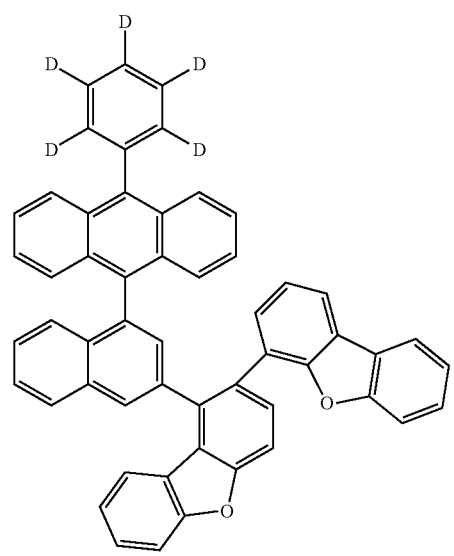

<Compound 87>
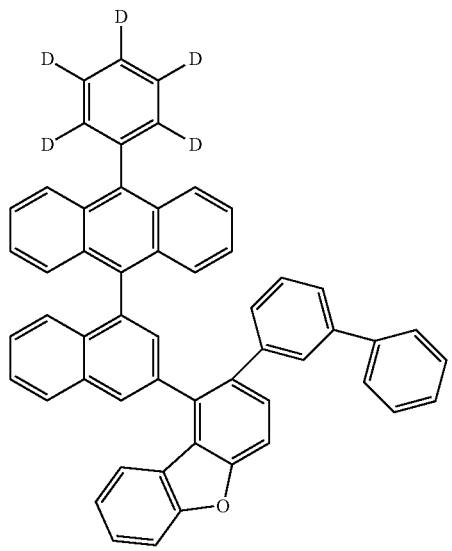
<Compound 88>
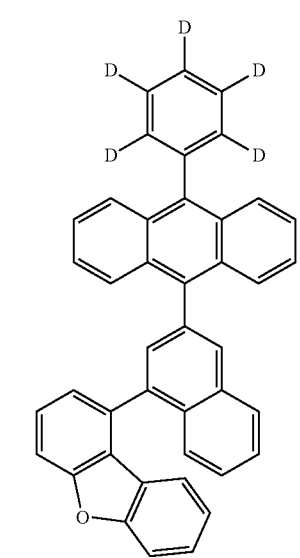
<Compound 90>
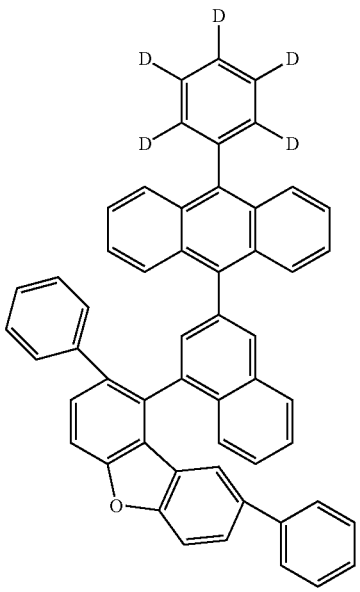
<Compound 89>
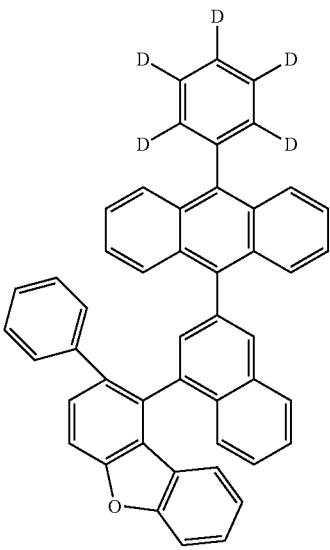
<Compound 91>
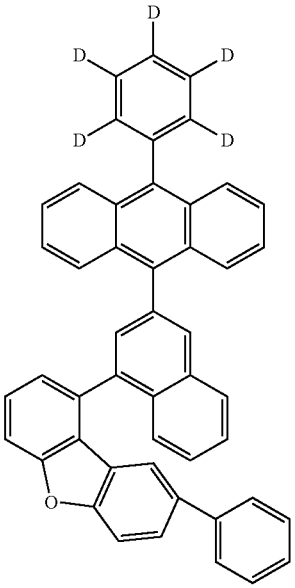

<Compound 92>
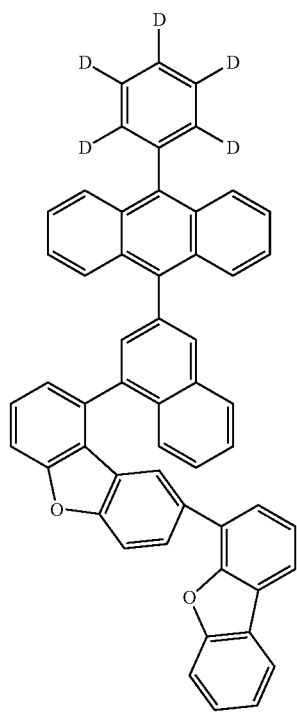
<Compound 93>
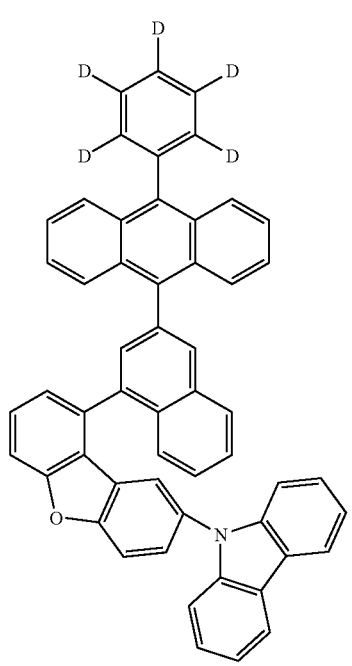
<Compound 94>
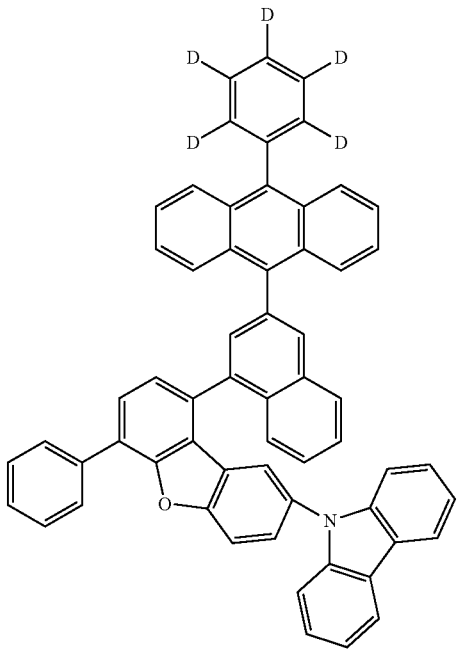
<Compound 95>
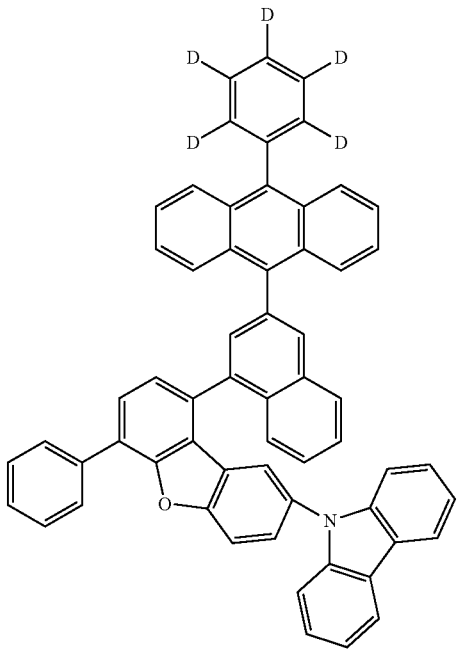

<Compound 96>
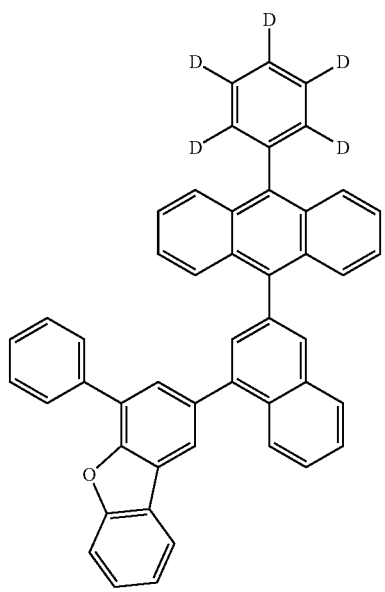
<Compound 97>
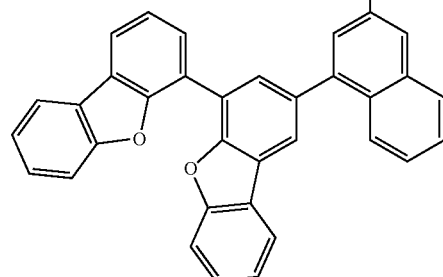
<Compound 98>
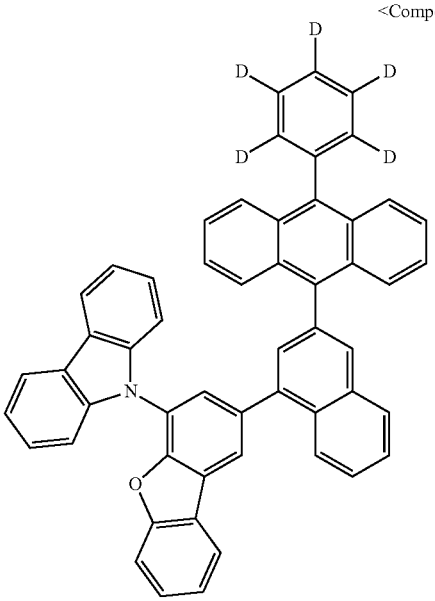
<Compound 99>
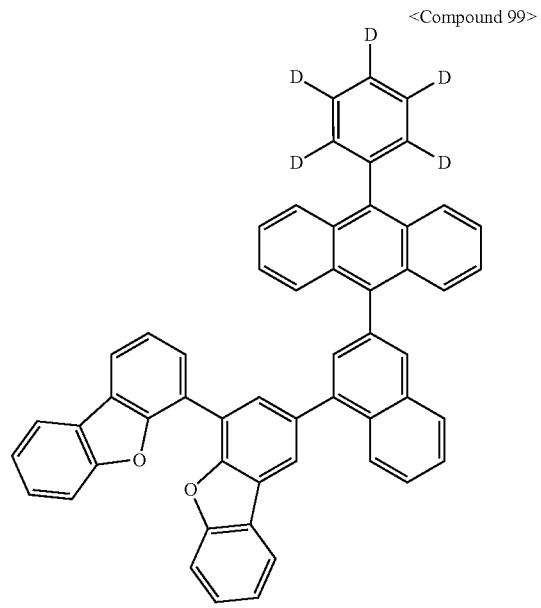
<Compound 100>
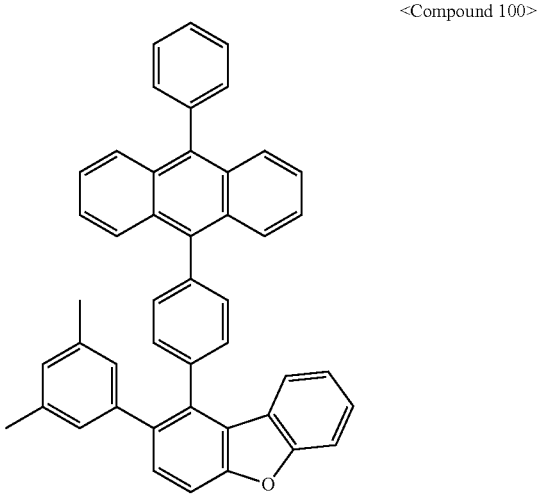

<Compound 101>
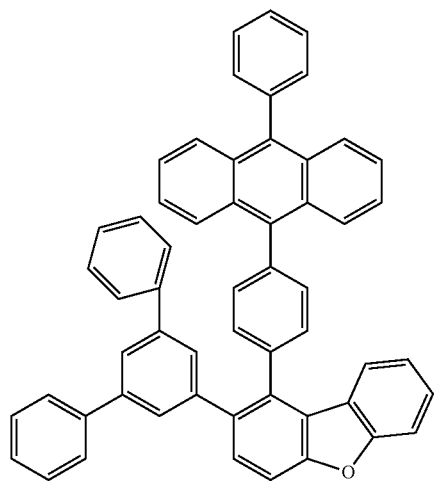
<Compound 102>
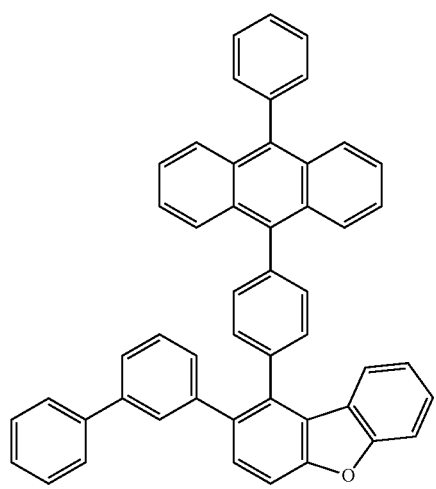
<Compound 103>
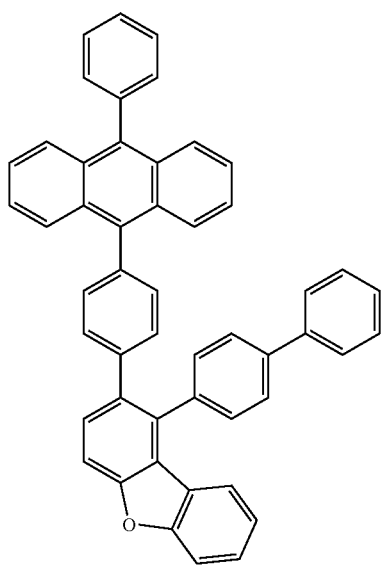
<Compound 104>
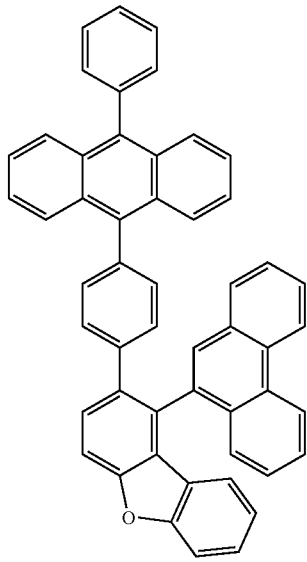
<Compound 105>
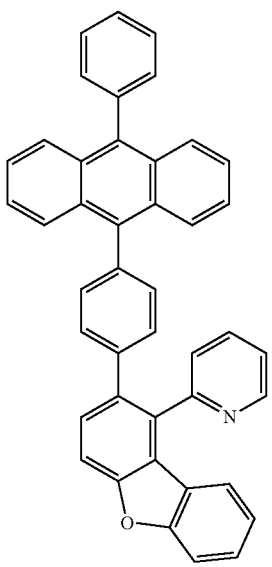
<Compound 106>
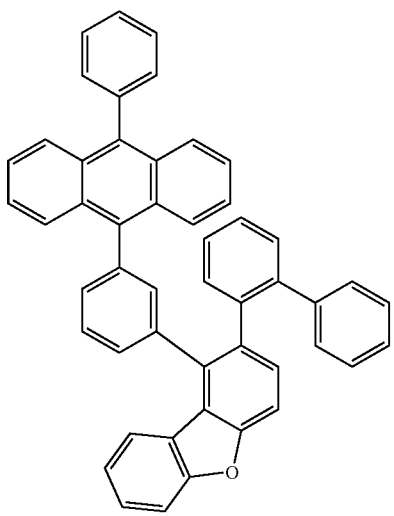

<Compound 107>
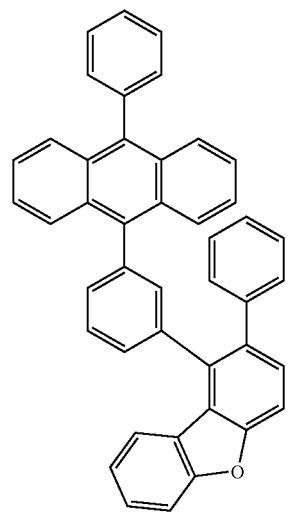
<Compound 108>
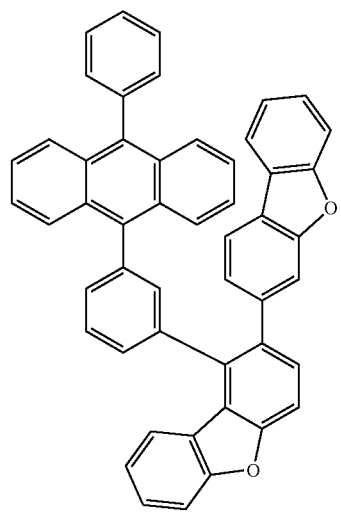
<Compound 109>
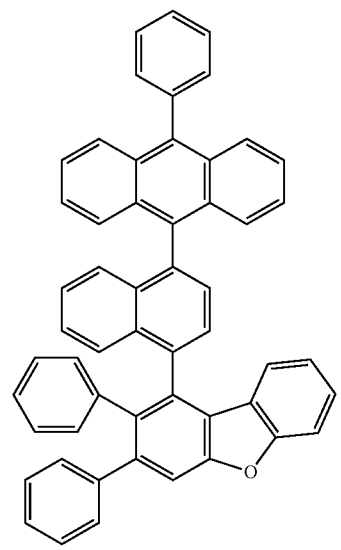
<Compound 110>
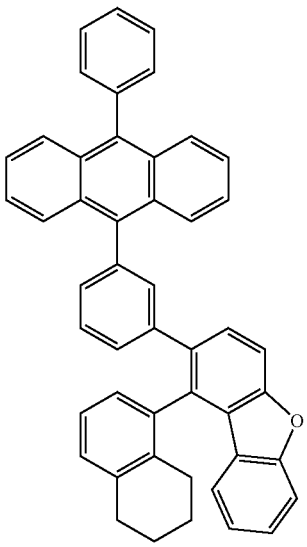
<Compound 111>
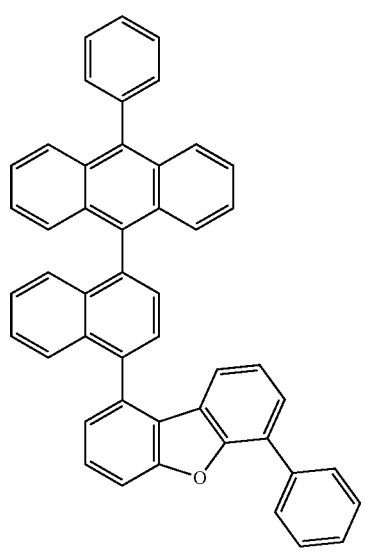
<Compound 112>
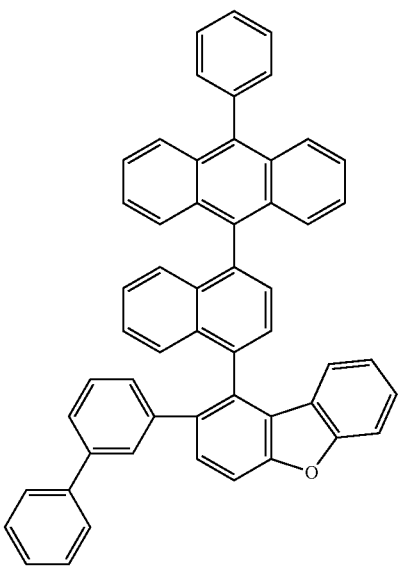

<Compound 113>
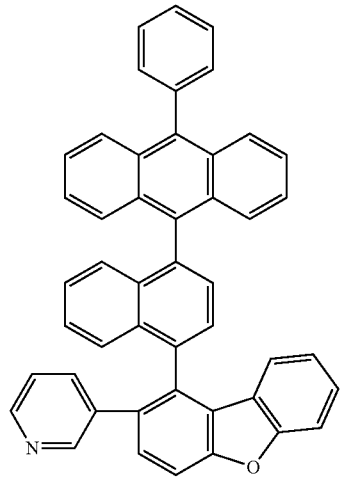
<Compound 114>
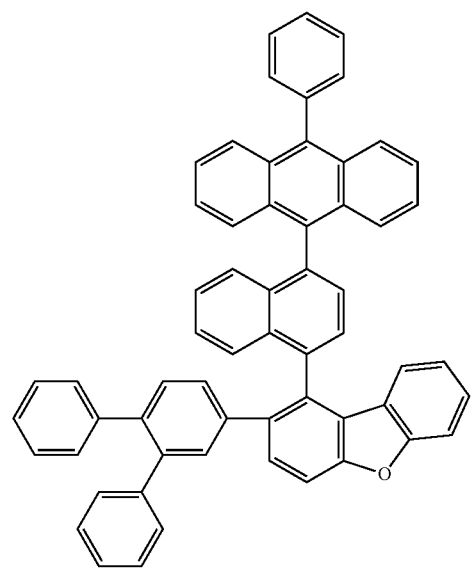
<Compound 115>
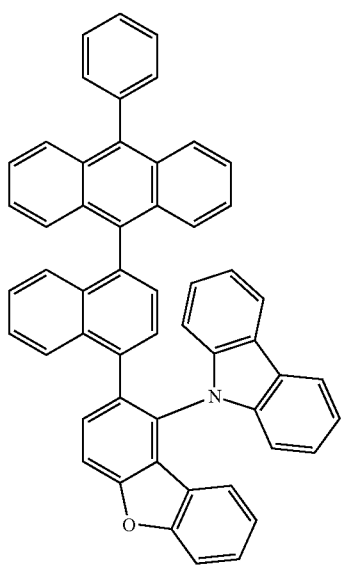
<Compound 116>
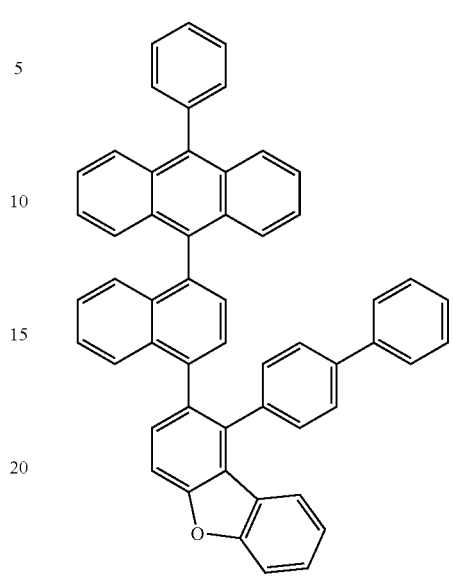
<Compound 117>
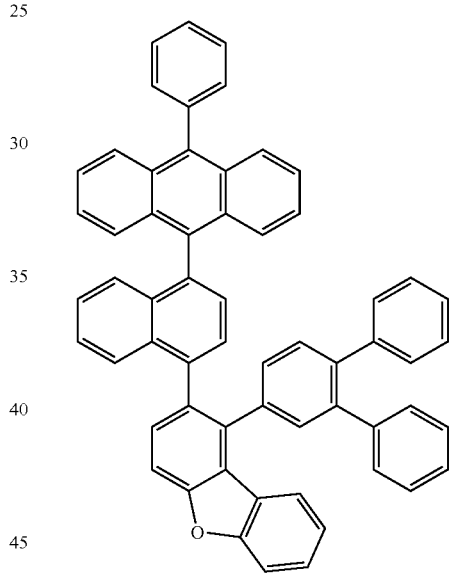
<Compound 118>
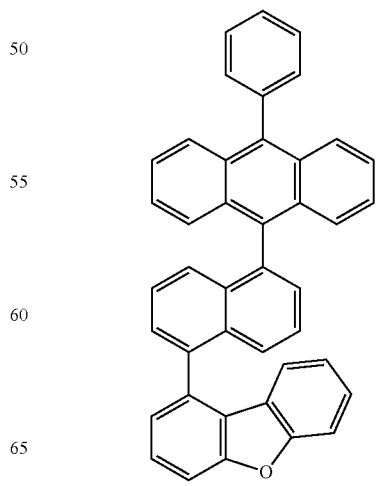

<Compound 119>
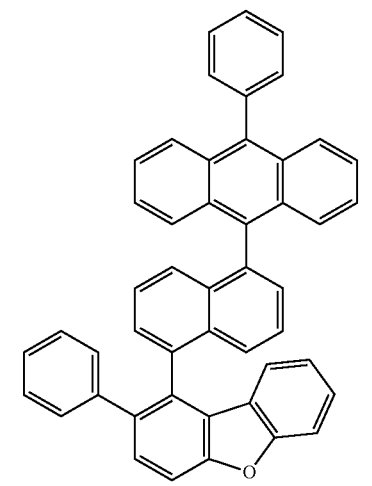
<Compound 120>
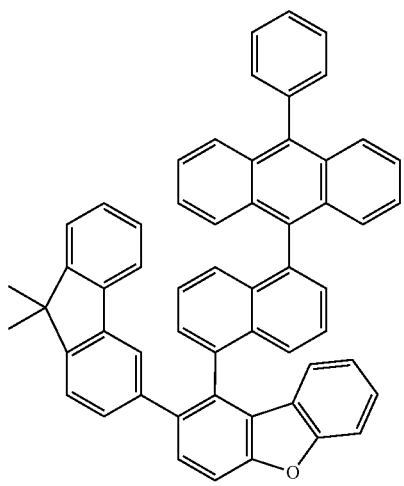
<Compound 121>
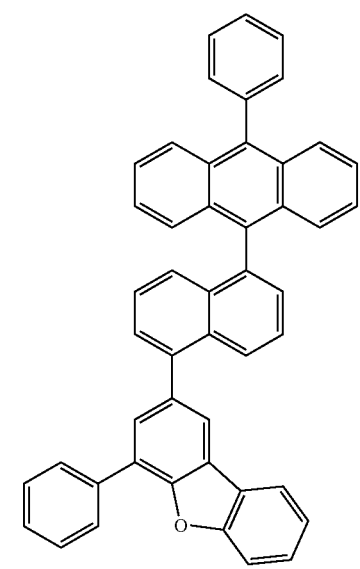
<Compound 122>
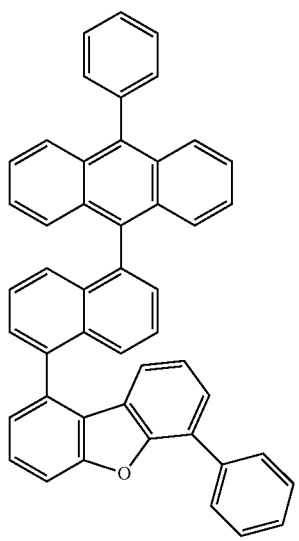
<Compound 123>
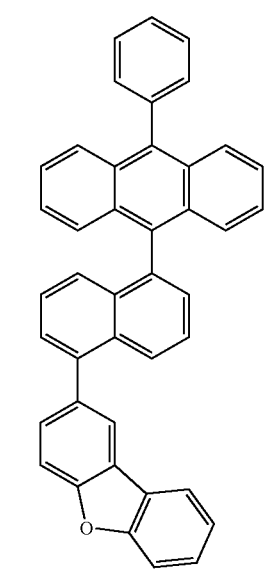
<Compound 124>

<Compound 125>
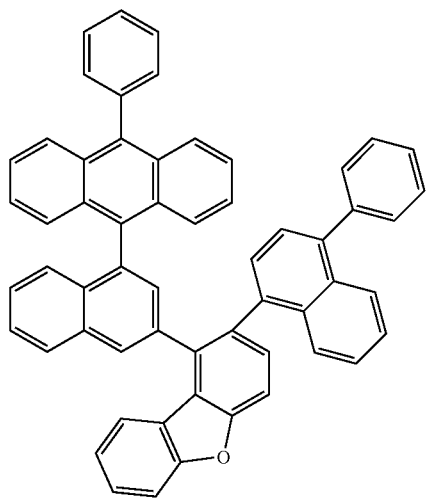
<Compound 126>
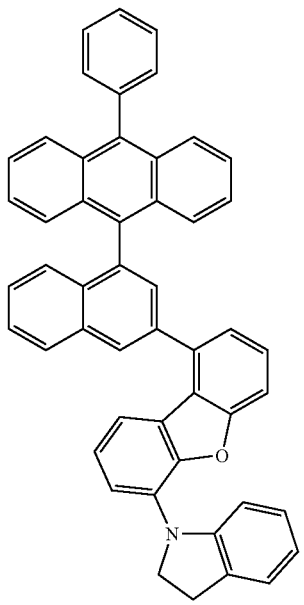
<Compound 127>
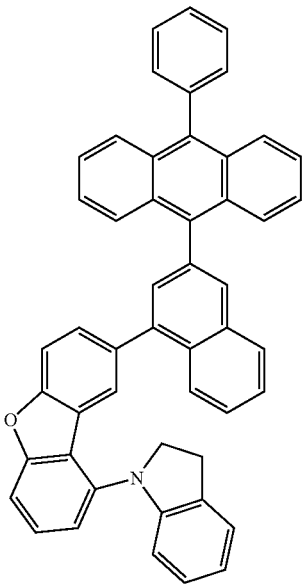
<Compound 128>
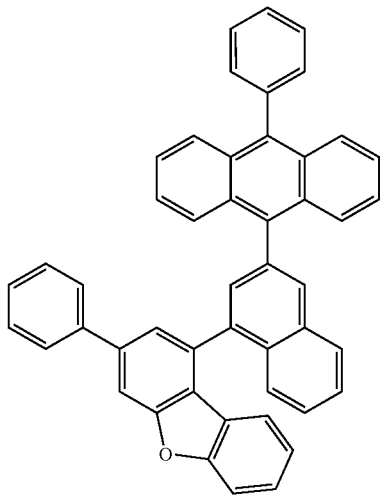

<Compound 129>
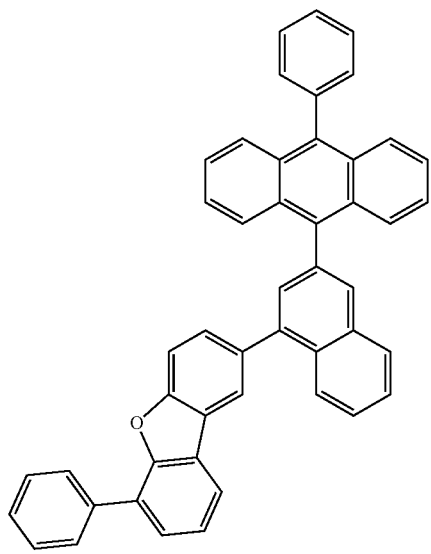
<Compound 130>
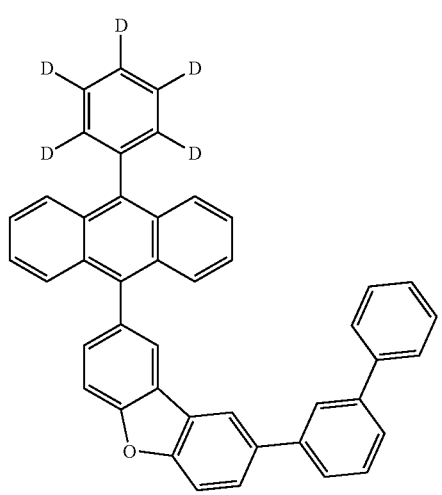
<Compound 131>
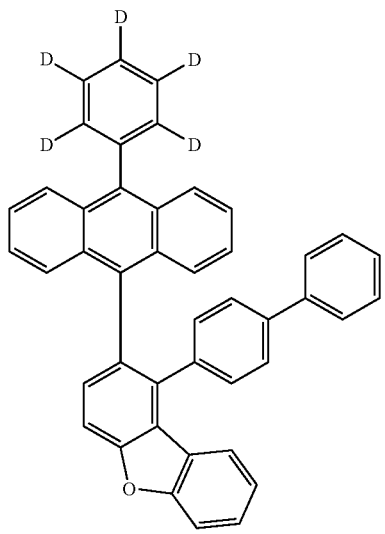
<Compound 132>
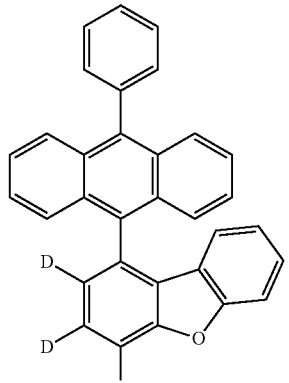
<Compound 133>
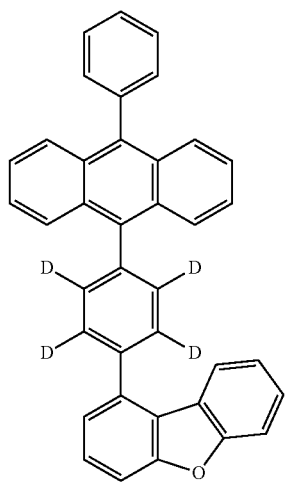
<Compound 134>
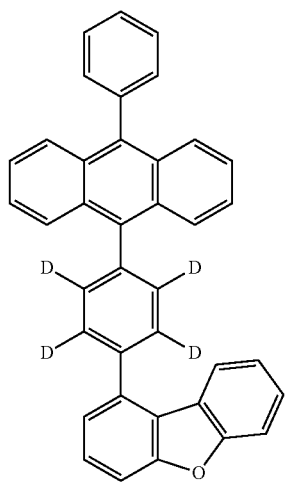

<Compound 135>

<Compound 136>

<Compound 137>

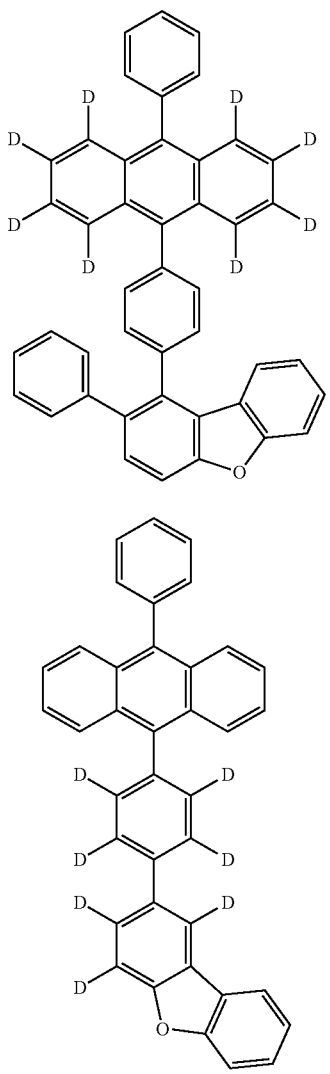

<Compound 138>

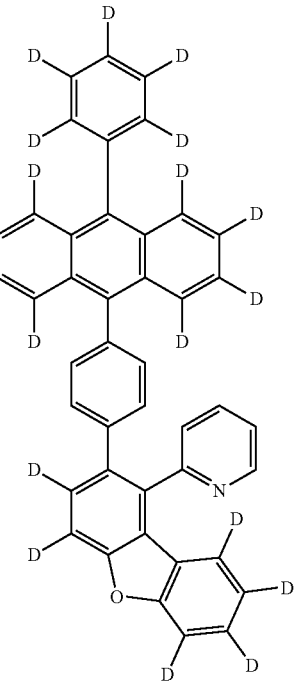

Also, the present disclosure provides an OLED, comprising a first electrode; a second electrode facing the first electrode; and an organic layer interposed therebetween, wherein the organic layer contains at least one of the organic luminescent compounds of the present disclosure.

As used herein, the expression "(the organic layer) contains at least one organic compound" is construed to mean that (the organic layer) may contain one organic compound falling within the scope of the present disclosure or two or more different compounds falling within the scope of the present disclosure.

According to some particular embodiments of the present disclosure, the organic layer containing the compound of the present disclosure may comprise at least one of a hole injecting layer, a hole transport layer, a functional layer capable of both hole injection and hole transport, an electron transport layer, and an electron injecting layer.

In addition, the organic layer interposed between the first electrode and the second electrode may be a light-emitting layer. In this regard, the light-emitting layer may be composed of a host and a dopant wherein the compound of Chemical Formula A may be used as the host.

Concrete examples of the dopant material used in the light-emitting layer include pyrene compounds, deuterium-substituted pyrene compounds, aryl amines, deuterium-substituted aryl amines, perylene compounds, deuterium-substituted perylene compounds, pyrrole compounds, deuterium-substituted pyrrole compounds, hydrazone compounds, deuterium-substituted hydrazone compounds, carbazole compounds, deuterium-substituted carbazole compounds, stilbene compounds, deuterium-substituted stilbene compounds, starburst-type compounds, deuterium-substituted starburst-type compounds, oxadiazole compounds, deuterium-substituted oxadiazole compounds, coumarin, and deuterium-substituted coumarin, but are not limited thereto.

According to the present disclosure, a dopant material may be used, together with a host, in the light-emitting layer.

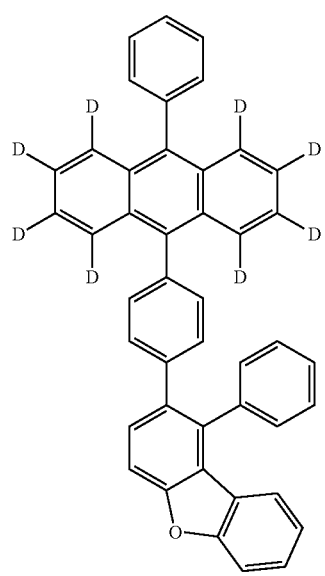

When the light-emitting layer comprises a host and a dopant, the content of the dopant in the light-emitting layer may range from about 0.01 to 20 parts by weight based on 100 parts by weight of the host, but is not limited thereto.

Further, one or more layers selected from among a hole injecting layer, a hole transport layer, a functional layer capable of both hole injection and hole transport, a light-emitting layer, an electron transport layer, and an electron injecting layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

In one embodiment of the present disclosure, a hole transport layer (HTL) may be further deposited between the anode and the organic light-emitting layer while an electron transport layer (ETL) may be further deposited between the cathode and the organic light-emitting layer.

As a material for the hole transport layer, an electron donating molecule with low ionization potential is used. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injecting layer (HIL) may be further deposited beneath the hole transport layer. No particular limitations are imposed on the hole injecting layer material, as long as it is one that is typically used in the art. Examples include CuPc (copperphthalocyanine), and the starburst amines TCTA (4,4',4''-tri(N-carbazolyl)triphenyl-amine), and m-MTDATA (4,4',4''-tris-(3-methylphenylphenyl amino)triphenylamine).

Further, other examples of the hole injecting layer material include the oxadiazole derivatives PBD, BMD, and BND, and Alq3.

An electron injecting layer that functions to facilitate electron injection from the cathode, thus improving the power efficiency of the diode, may be further deposited on the electron transport layer. So long as it is conventionally used in the art, any material can be available for the electron injecting layer without particular limitations. Examples include LiF, NaCl, CsF, Li2O, and BaO.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injecting layer 30 or an electron injecting layer 70. In addition, one or two intermediate layers may be further formed in the organic light-emitting diode.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used.

A hole injecting layer material is applied on the anode electrode 20 by thermal deposition in a vacuum or by spin coating to form a hole injecting layer 30. Subsequently, thermal deposition in a vacuum or by spin coating may also be conducted to form a hole transport layer 40 with a hole transport layer material on the hole injecting layer 30.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å. In addition, the light-emitting layer may be composed of a host and a dopant wherein the host may be the compound of the present disclosure.

The dopant may be a compound represented by Chemical Formula 1 or 2. In this regard, the light-emitting layer may further contain various dopant materials.

[Chemical Formula 1]

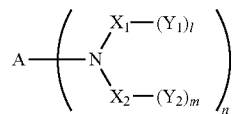

[Chemical Formula 2]

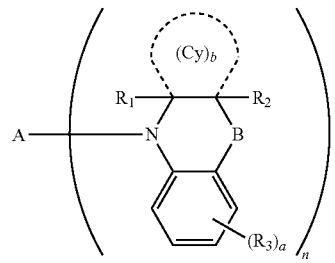

wherein A may be any one selected from among a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom.

In greater detail, A may be a substituted or unsubstituted arylene of 6 to 60 carbon atoms, or a single bond, particularly any one selected from among anthracene, pyrene, phenanthrene, indenophenanthrene, chrysene, naphthacene, pycene, triphenylene, perylene, and pentacene, and more particularly a substituent represented by the following Chemical Formulas A1 to A10:

[Chemical Formula A1]

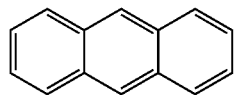

[Chemical Formula A2]

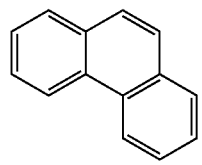

[Chemical Formula A3]

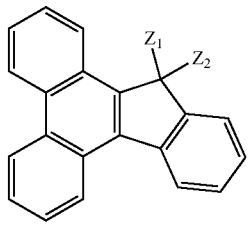

[Chemical Formula A4]

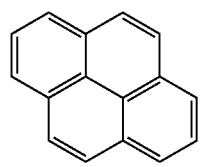

[Chemical Formula A5]

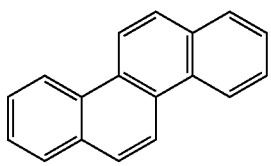

[Chemical Formula A6]

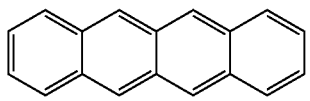

[Chemical Formula A7]

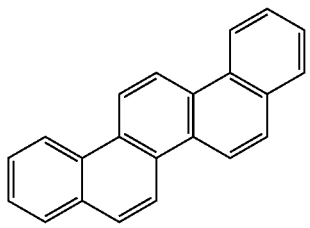

[Chemical Formula A8]

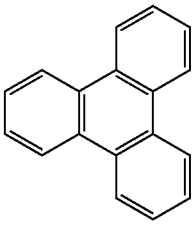

[Chemical Formula A9]

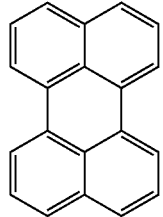

[Chemical Formula A10]

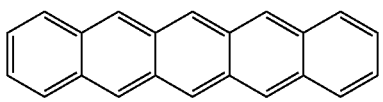

In Chemical Formula A3, Z1 and Z2 may be the same or different and are each independently selected from the group consisting of a hydrogen, a deuterium, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl)amino of 6 to 60 carbon atoms, with the proviso that Z1 and Z2 may each form a fused ring with an adjacent radical.

In Chemical Formula 1,

X1 and X2 may each be independently a substituted or unsubstituted arylene of 6 to 30 carbon atoms or a single bond, with the proviso that X1 and X2 may bond to each other, Y1 and Y2 may be the same or different and are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that Y1 and Y2 may each form with an aliphatic, aromatic, heteroaliphatic or heteroaromatic fused ring with an adjacent radical, l and m are each an integer of 1 to 20, and n is an integer of 1 to 4.

In Chemical Formula 2,

Cy is a substituted or unsubstituted cycloalkyl of 3 to 8 carbon atoms and b is an integer of 1 to 4, with the proviso that when b is an integer of 2 or greater, the corresponding cycloalkanes may be the same or different and may be individually in a fused form having a deuterium or an alkyl as a substituent.

In Chemical Formula 2,

B is a single bond or —[C(R5)(R6)]p- wherein p is an integer of 1 to 3, with the proviso that when p is 2 or greater, the corresponding R5's and R6's are individually the same or different;

R1, R2, R3, R5, and R6 may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl) amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, a is an integer of 1 to 4, with the proviso that when a is 2 or greater, the corresponding plural R3's may be the same or different and may be individually in a fused form, and n is an integer of 1 to 4.

The amine radical of Chemical Formulas 1 and 2, which is linked to A, may be represented by any one selected from among, but not limited to, the following Substituents 1 to 52:

[Substituent 1]

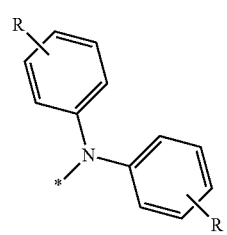

[Substituent 2]

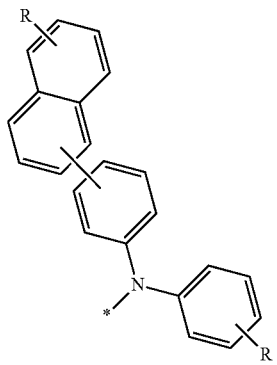

[Substituent 3]

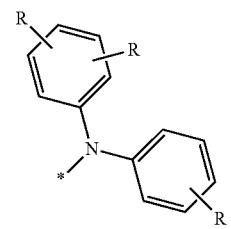

[Substituent 4]

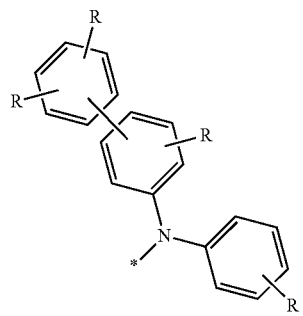

[Substituent 5]

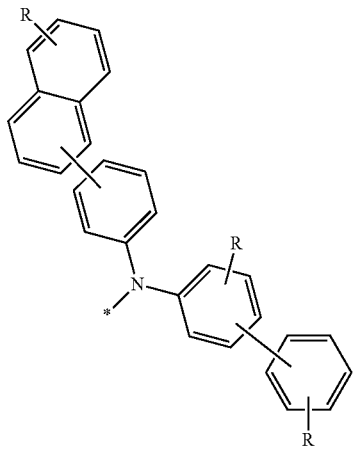

73
-continued
[Substituent 6]
[Substituent 7]
[Substituent 8]
[Substituent 9]
[Substituent 10]
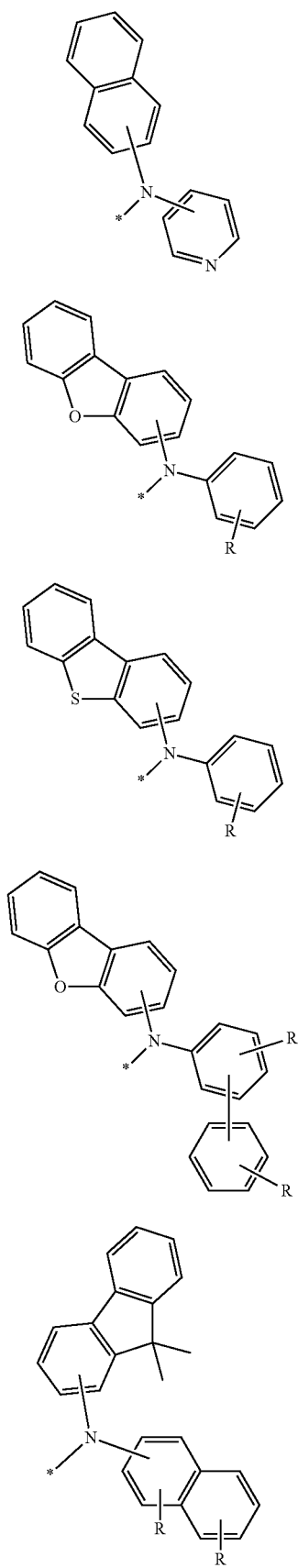
74
-continued
[Substituent 11]
[Substituent 12]
[Substituent 13]
[Substituent 14]
[Substituent 15]
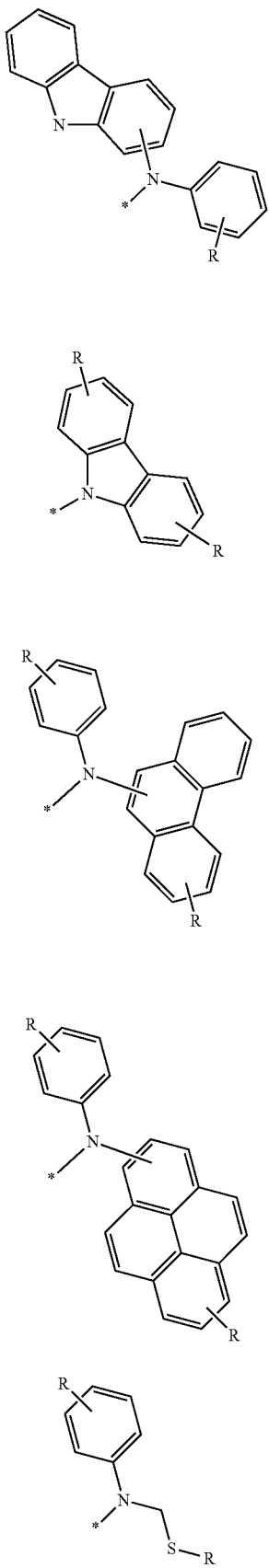

[Substituent 16]
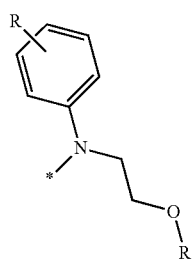
[Substituent 17]
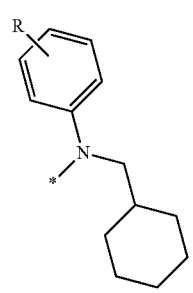
[Substituent 18]
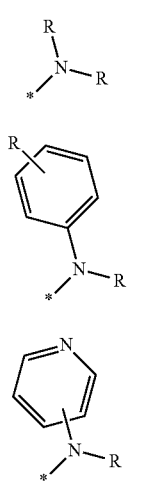
[Substituent 19]
[Substituent 20]
[Substituent 21]
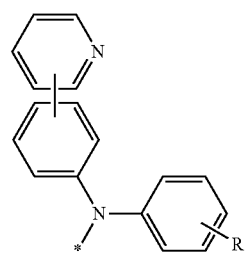
[Substituent 22]
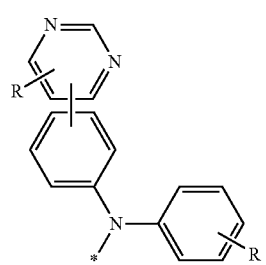
[Substituent 23]
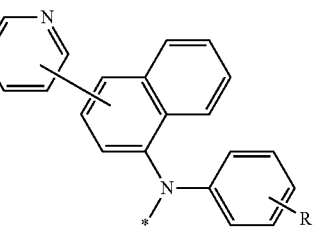
[Substituent 24]
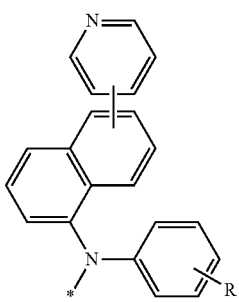
[Substituent 25]
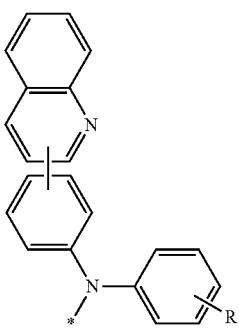
[Substituent 26]
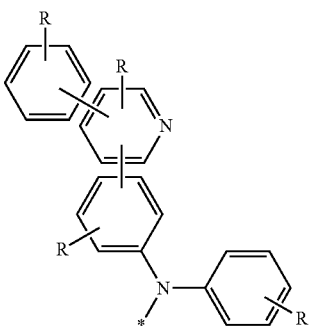
[Substituent 27]
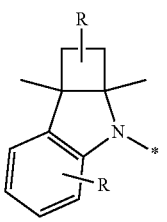

[Substituent 28] 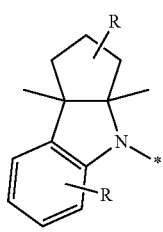
[Substituent 29] 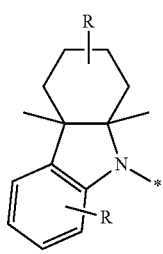
[Substituent 30] 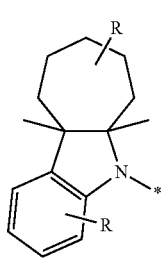
[Substituent 31] 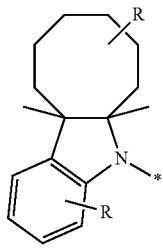
[Substituent 32] 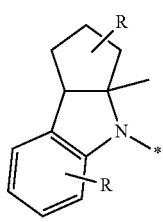
[Substituent 33] 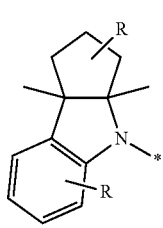
[Substituent 34] 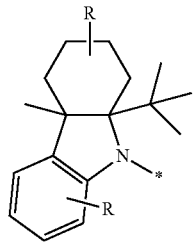
[Substituent 35] 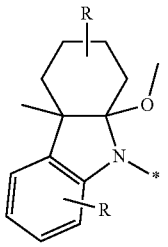
[Substituent 36] 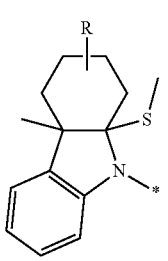
[Substituent 37] 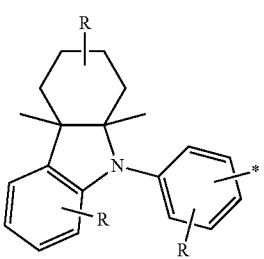
[Substituent 38] 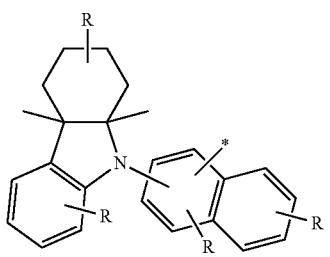
[Substituent 39] 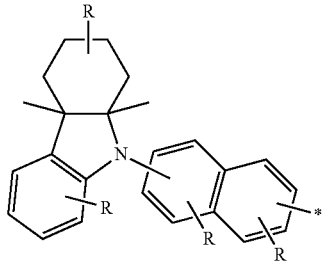

79
-continued
[Substituent 40]
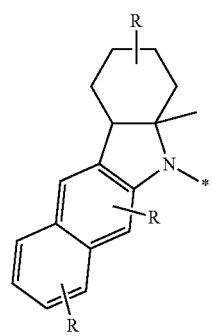
[Substituent 41]
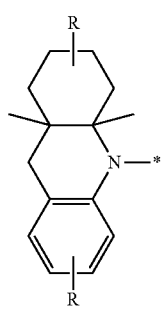
[Substituent 42]
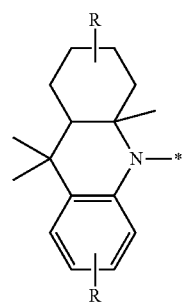
[Substituent 43]
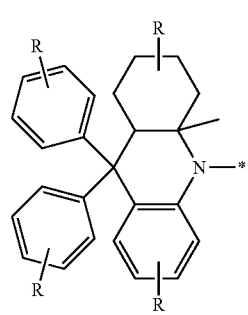
[Substituent 44]
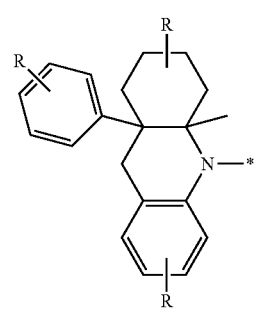
80
-continued
[Substituent 45]
[Substituent 46]
[Substituent 47]
[Substituent 48]
[Substituent 49]

-continued

[Substituent 50]

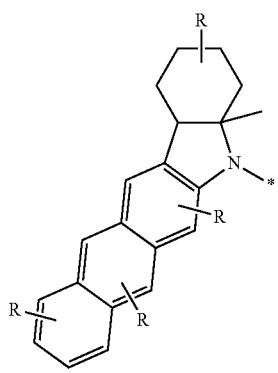

[Substituent 51]

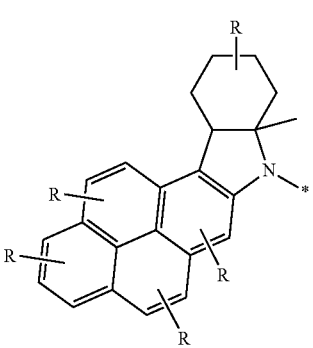

[Substituent 52]

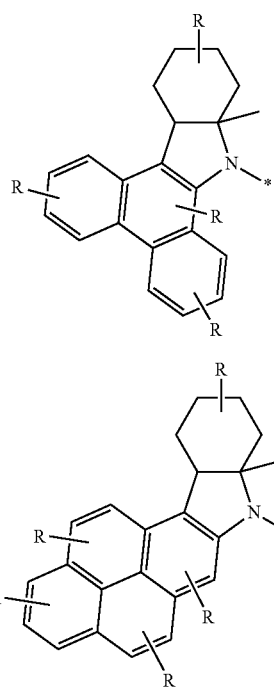

wherein R's may be the same or different and are each independently selected from among a hydrogen atom, a deuterium atom, a halogen atom, a hydroxyl, a cyano, a nitro, an amino, an amidino, a hydrazine, a hydrazaone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, and may each form a fused ring with an adjacent radical.

A better understanding of the present disclosure may be obtained through the following examples which are set forth to illustrate, but are not to be construed as limiting the present disclosure.

EXAMPLES

Synthesis Example 1: Synthesis of Compound 1

Synthesis Example 1-(1): Synthesis of Intermediate 1-a

Intermediate 1-a was synthesized as illustrated in the following Reaction Scheme 1:

<Reaction Scheme 1>

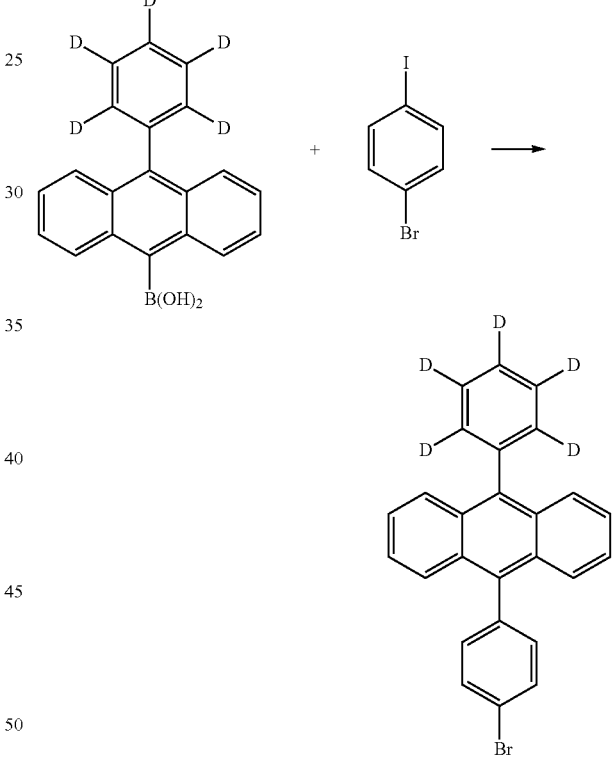

<Intermediate 1-a>

In a 500-mL round-bottom flask reactor, (10-phenyl(d5)-anthracene-9-boronic acid (38.6 g, 127 mmol), 1-bromo-4-iodobenzene (30.0 g, 106 mmol), tetrakis(triphenylphosphine)palladium (3.43 g, mmol), and potassium carbonate (27.35 g, 197.9 mmol) were placed, followed by toluene (150 mL), tetrahydrofuran (150 mL), and water (60 mL). The temperature of the reactor was increased to 90° C. and stirring was conducted overnight. After completion of the reaction, the reaction mixture was cooled to room temperature and extracted with ethyl acetate. The organic layer thus formed was separated and concentrated in a vacuum, followed by purification through column chromatography to afford <Intermediate 1-a>. (35.0 g, 79.7%)

Synthesis Example 1-(2): Synthesis of Intermediate 1-b

Intermediate 1-b was synthesized as illustrated in the following Reaction Scheme 2:

<Reaction Scheme 2>

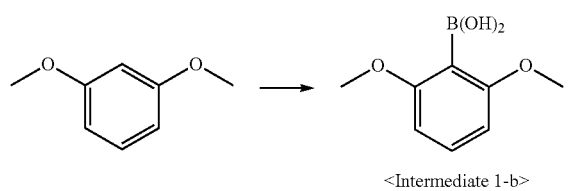

<Intermediate 1-b>

In a well-dried 2-L round-bottom flask reactor, 1,3-dimethoxy benzene (100.0 g, 0.724 mol) was dissolved in tetrahydrofuran (800 ml). The solution was chilled to −10° C. in a nitrogen atmosphere and then added slowly with drops of n-butyl lithium (543 ml, 0.868 mol). After 4 hrs of stirring at the same temperature, the temperature was decreased to −78° C. While this temperature was maintained, drops of trimethyl borate (112.8 g, 1.086 mol) were slowly added over 30 min, followed by stirring overnight at room temperature. After completion of the reaction, 2 N HCl was dropwise added for acidification. Extraction was made with water and ethyl acetate, and the organic layer thus formed was dried over magnesium sulfate. Subsequent to vacuum concentration, crystallization was conducted in heptane. The solid thus formed was filtered and washed with heptane to afford <Intermediate 1-b>. 92.0 g, 69%)

Synthesis Example 1-(3): Synthesis of Intermediate 1-c

Intermediate 1-c was synthesized as illustrated in the following Reaction Scheme 3:

<Reaction Scheme 3>

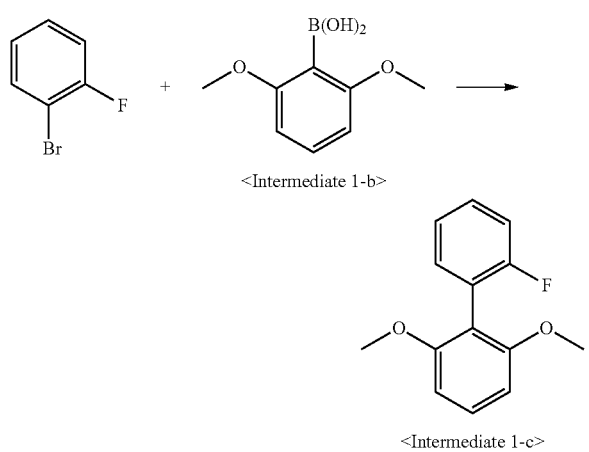

<Intermediate 1-c>

In a 2-L round-bottom flask reactor, 1-bromo-2-fluorobenzene (80.0 g, 0.457 mol), <Intermediate 1-b> (91.5 g, 0.503 mol), tetrakis(triphenylphosphine)palladium (11.6 g, 0.01 mol), and potassium carbonate (126.4 g, 0.914 mol) were placed, followed by toluene (400 mL), tetrahydrofuran (400 mL), and water (160 mL). The temperature of the reactor was increased to 80° C. and stirring was conducted overnight. After completion of the reaction, the reaction mixture was cooled to room temperature and extracted with ethyl acetate. The organic layer thus formed was separated and concentrated in a vacuum, followed by purification through column chromatography to afford <Intermediate 1-c>. (85.0 g, 80%)

Synthesis Example 1-(4): Synthesis of Intermediate 1-d

Intermediate 1-d was synthesized as illustrated in the following Reaction Scheme 4:

<Reaction Scheme 4>

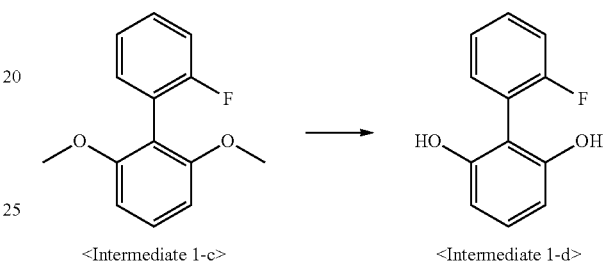

<Intermediate 1-c>        <Intermediate 1-d>

In a 2-L round-bottom flask reactor, <Intermediate 1-c> (85.0 g, 0.366 mol) was added with acetic acid (510 ml) and hydrobromic acid (340 ml) and stirred overnight under reflux. After completion of the reaction, the reaction mixture was cooled to room temperature and dropwise added little by little to cold water (1000 ml). Extraction was made with water and ethyl acetate and the organic layer thus formed was isolated, washed with an aqueous sodium hydrogen carbonate solution (400 ml), and concentrated in a vacuum. Purification through column chromatography afforded <Intermediate 1-d>. (71 g, 95%)

Synthesis Example 1-(5): Synthesis of Intermediate 1-e

Intermediate 1-e was synthesized as illustrated in the following Reaction Scheme 5:

<Reaction Scheme 5>

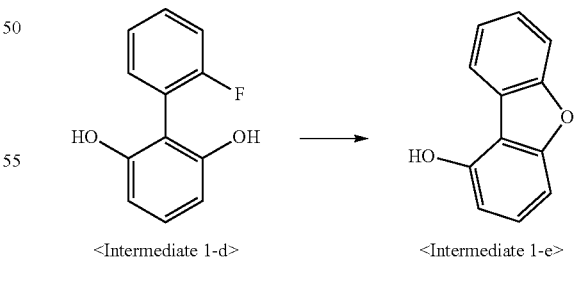

<Intermediate 1-d>        <Intermediate 1-e>

In a 2-L round-bottom flask reactor, <Intermediate 1-d> (71.0, 39 mmol), potassium carbonate (96.1 g, 0.695 mol), and 1-methyl-2-pyrrolidinone (1060 ml) were stirred together overnight at 120° C. After completion of the reaction, the reaction mixture was cooled to room temperature and dropwise added to cold water (1000 ml). Extraction with water and ethyl acetate formed an organic layer which was then isolated and concentrated in a vacuum. Purification through column chromatography afforded <Intermediate 1-e>. (60.0 g, 93.7%)

Synthesis Example 1-(6): Synthesis of Intermediate 1-f

Intermediate 1-f was synthesized as illustrated in the following Reaction Scheme 6:

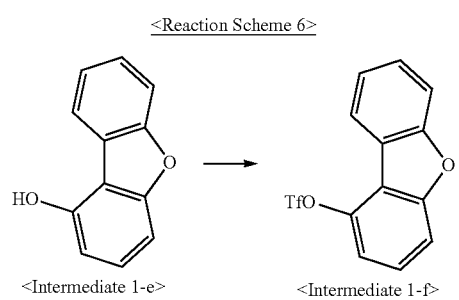 [SMILES: Oc1cccc2oc3ccccc3c12 ; O=S(=O)(Oc1cccc2oc3ccccc3c12)C(F)(F)F]

<Reaction Scheme 6>

<Intermediate 1-e>   <Intermediate 1-f>

In a 2-L round-bottom flask reactor, <Intermediate 1-e> (60.0 g, 0.326 mol) was dissolved in methylene chloride (600 ml) and slowed added with pyridine (38.7 g, 0.489 mol) before stirring at room temperature for 30 min. The solution was cooled to 0° C. and added with drops of trifluoromethane sulfonyl anhydride (137.8 g, 0.489 mol) at the same temperature. After 5 hrs of stirring at room temperature, the reaction solution was added with water (100 ml) and stirred again for 10 min. Extraction with water and ethyl acetate formed an organic layer which was then isolated and concentrated in a vacuum. Purification through column chromatography afforded <Intermediate 1-f>. (87 g, 84.5%)

Synthesis Example 1-(7): Synthesis of Intermediate 1-g

Intermediate 1-g was synthesized as illustrated in the following Reaction Scheme 7:

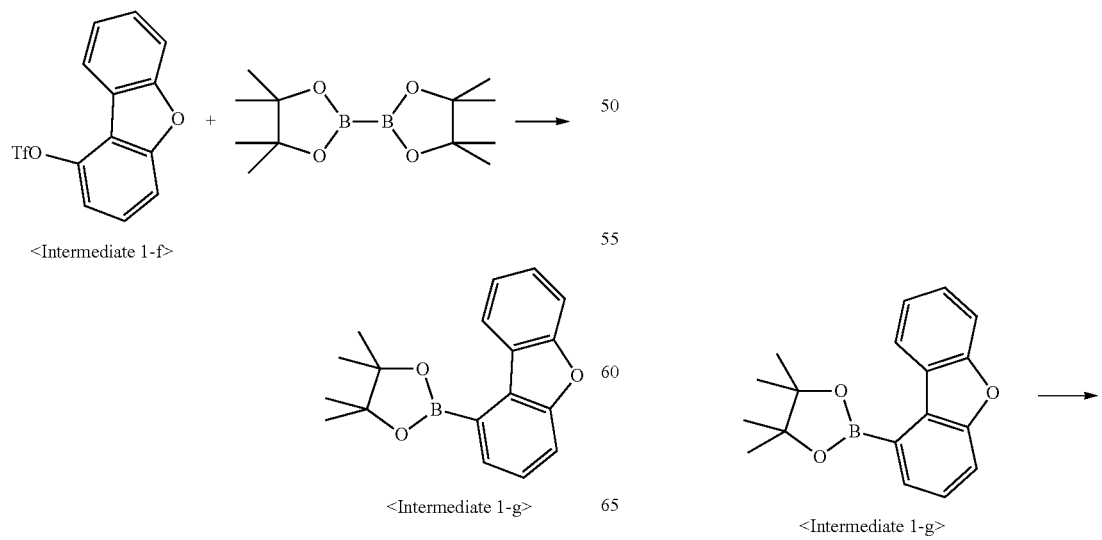

<Reaction Scheme 7>

<Intermediate 1-f>

<Intermediate 1-g>   <Intermediate 1-g>

In a 2-L round-bottom flask reactor, <Intermediate 1-f> (87.0 g, 0.275 mol), bis(pinacolato)diboron (83.8 g, 0.330 mol), 1,1'-bis(diphenylphosphino)ferocene-palladium(II) dichloride (4.5 g, 0.006 mol), potassium acetate (54.0 g, 0.550 mol), and 1,4-dioxane (870 ml) were placed and stirred overnight under reflux. After completion of the reaction, the reaction mixture was filtered through a celite pad and the filtrate was concentrated in a vacuum. The concentrate was purified by column chromatography to afford <Intermediate 1-g>. (65.3 g, 80.7%)

Synthesis Example 1-(8): Synthesis of Compound 1

Compound 1 was synthesized as illustrated in the following Reaction Scheme 8:

<Reaction Scheme 8>

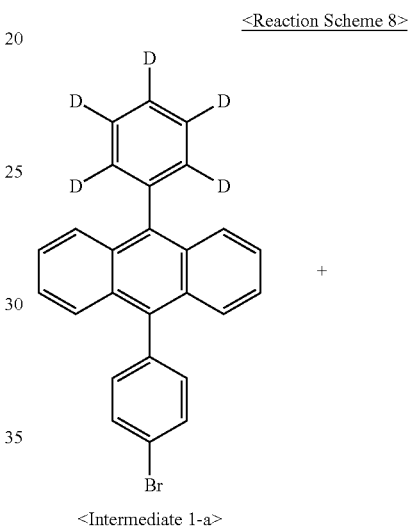

+

<Intermediate 1-a>

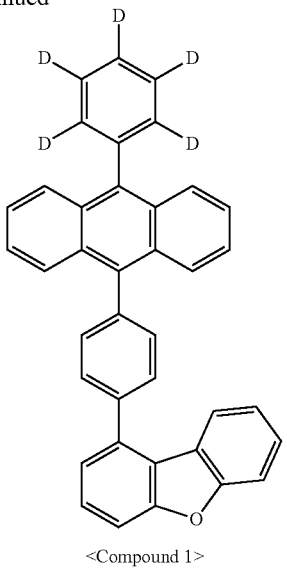

<Compound 1>

In a 250-mL round-bottom flask reactor, <Intermediate 1-a> (5.5 g, 13 mmol), <Intermediate 1-g> (4.7 g, 16 mmol), tetrakis(triphenylphosphine)palladium (0.46 g, 3 mmol), and potassium carbonate (3.67 g, 26.5 mmol) were placed, followed by toluene (30 mL), 1,4-dioxane (30 mL) and water (11 mL). The temperature of the reactor was elevated to 90° C. before stirring overnight. After completion of the reaction, the reaction mixture was cooled to room temperature and extracted with ethyl acetate. The organic layer thus formed was isolated and concentrated in a vacuum, followed by purification through column chromatography. Recrystallization in toluene and acetone afforded <Compound 1>. (3.2 g, 48%)

MS: m/z 502.2 [M+]

Synthesis Example 2: Synthesis of Compound 13

Synthesis Example 2-(1): Synthesis of Intermediate 2-a

Intermediate 2-a was synthesized as illustrated in the following Reaction Scheme 9:

<Reaction Scheme 9>

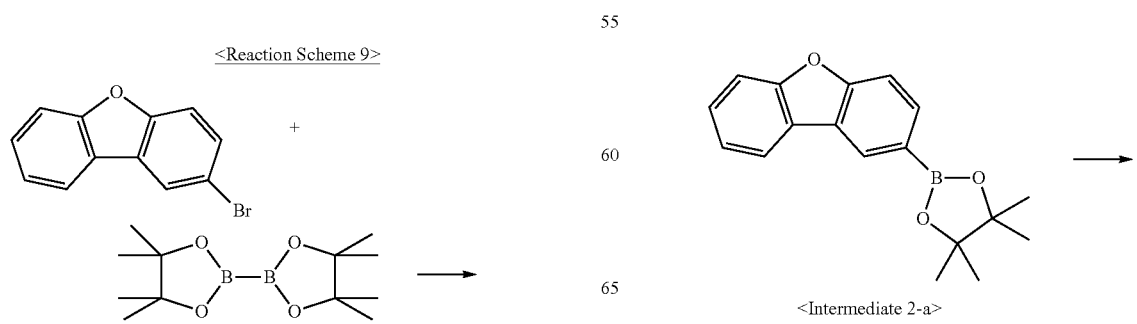

<Intermediate 2-a>

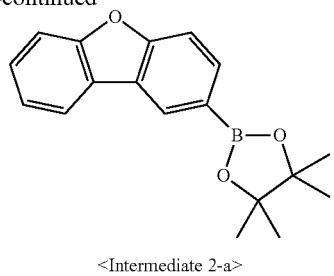

<Intermediate 2-a>

In a 2-L round-bottom flask reactor, a mixture of 2-bromodibenzofuran (70.0 g, 0.283 mol), bis(pinacolato)diboron (86.3 g, 0.340 mol), 1,1'-bis(diphenylphosphino)ferrocene-palladium(II) dichloride (4.6 g, 0.006 mol), potassium acetate (56.6 g, 0.567 mol), and 1,4-dioxane (700 ml) was stirred overnight under reflux. After completion of the reaction, the reaction mixture was filtered through a celite pade and the filtrate was concentrated in a vacuum. The concentrate was purified using column chromatography to afford Intermediate 2-a. (66.4 g, 79%)

Synthesis Example 2-(2): Synthesis of Compound 13

Compound 13 was synthesized as illustrated in the following Reaction Scheme 10:

<Reaction Scheme 10>

<Intermediate 1-a>

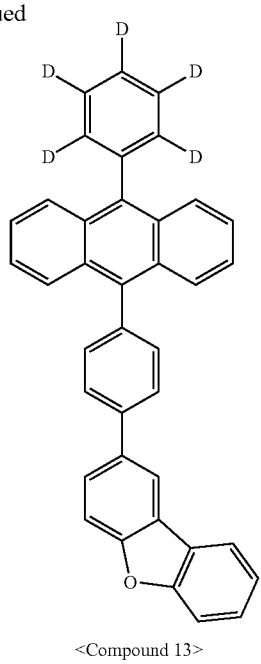

<Compound 13>

The same procedure was carried out as in Synthesis Example 1-(8), with the exception of using Intermediate 2-a instead of Intermediate 1-g, to afford Compound 13. (3.0 g, 66.1%).

MS: m/z 502.2 [M+]

Synthesis Example 3: Synthesis of Compound 22

Synthesis Example 3-(1): Synthesis of Intermediate 3-a

Intermediate 3-a was synthesized as illustrated in the following Reaction Scheme 11:

<Reaction Scheme 11>

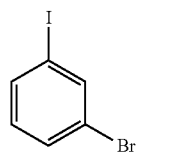

+

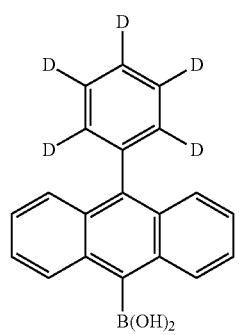

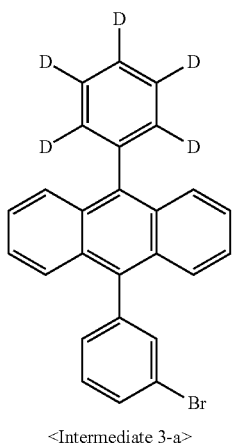

<Intermediate 3-a>

The same procedure was carried out as in Synthesis Example 1-(1), with the exception of using 1-bromo-3-iodobenzene instead of 1-bromo-4-iodobenzene, to afford Intermediate 3-a. (32 g, 72.8%)

Synthesis Example 3-(2): Synthesis of Compound 22

Compound 22 was synthesized as illustrated in the following Reaction Scheme 12:

<Reaction Scheme 12>

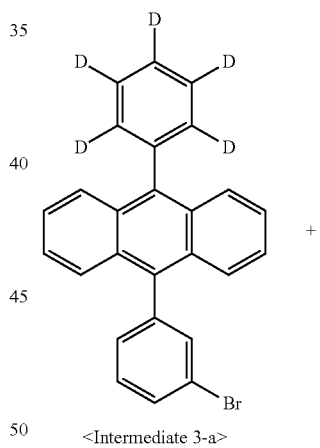

+

<Intermediate 3-a>

<Intermediate 1-g>

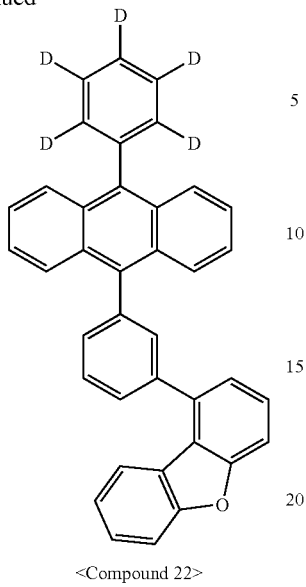

<Compound 22>

The same procedure was carried out as in Synthesis Example 1-(8), with the exception of using Intermediate 3-a instead of Intermediate 1-a, to afford Compound 22. (3.5 g, 57.8%)

MS: m/z 502.2 [M+]

Synthesis Example 4: Synthesis of Compound 31

Synthesis Example 4-(1): Synthesis of Compound 31

Compound 31 was synthesized as illustrated in the following Reaction Scheme 13:

<Reaction Scheme 13>

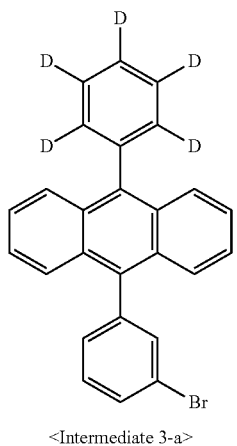

+

<Intermediate 3-a>

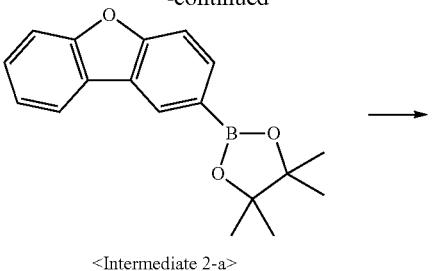

<Intermediate 2-a>

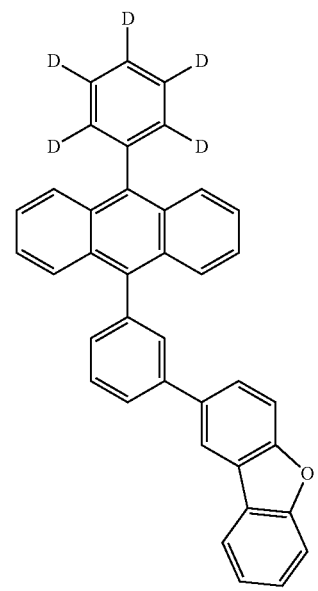

<Compound 31>

The same procedure was carried out as in Synthesis Example 2-(2), with the exception of using Intermediate 3-a instead of Intermediate 1-a, to afford Compound 31. (2.7 g, 44.6%)

MS: m/z 502.2 [M+]

Synthesis Example 5: Synthesis of Compound 43

Synthesis Example 5-(1): Synthesis of Intermediate 5-a

Intermediate 5-a was synthesized as illustrated in the following Reaction Scheme 14:

<Reaction Scheme 14>

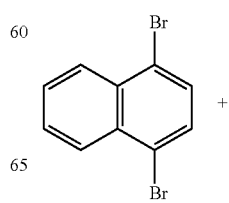

+

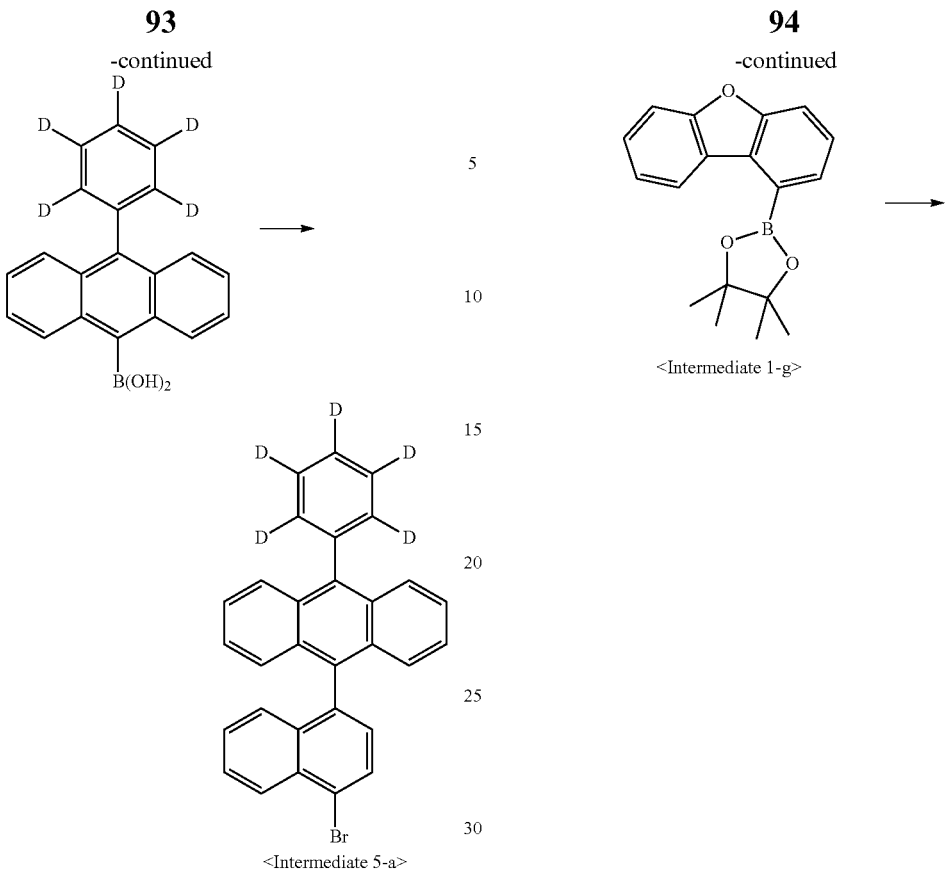

<Intermediate 5-a>

The same procedure was carried out as in Synthesis Example 1-(1), with the exception of using 1,4-dibromonaphthalene instead of 1-bromo-4-iodobenzene, to afford Intermediate 5-a. (29 g, 59.5%)

Synthesis Example 5-(2): Synthesis of Compound 43

Compound 43 was synthesized as illustrated in the following Reaction Scheme 15:

<Reaction Scheme 15>

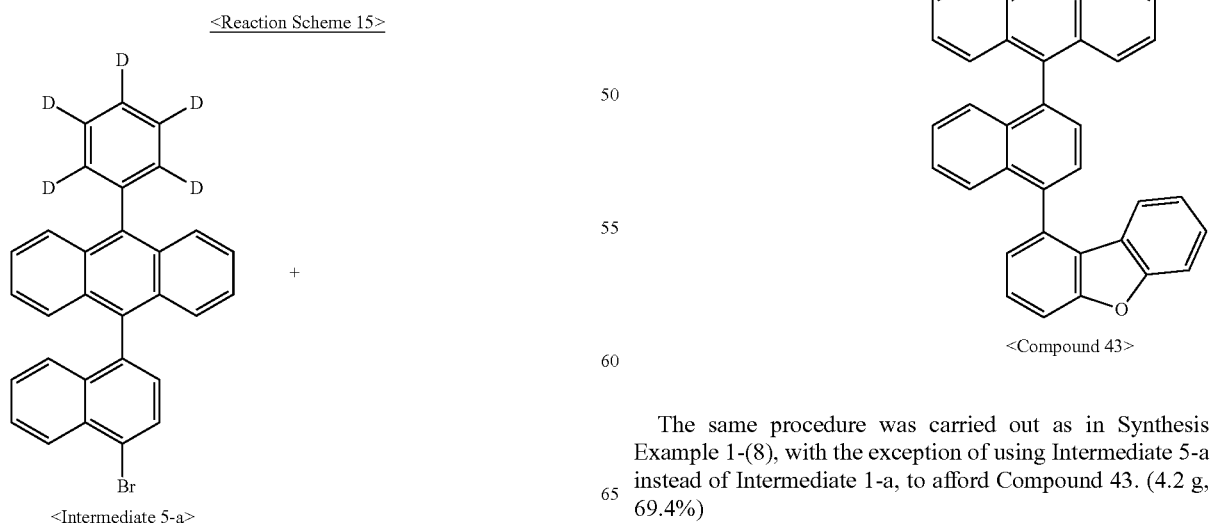

<Compound 43>

The same procedure was carried out as in Synthesis Example 1-(8), with the exception of using Intermediate 5-a instead of Intermediate 1-a, to afford Compound 43. (4.2 g, 69.4%)

MS: m/z 552.2 [M+]

Synthesis Example 6: Synthesis of Compound 52

Synthesis Example 6-(1): Synthesis of Compound 52

Compound 52 was synthesized as illustrated in the following Reaction Scheme 16:

<Reaction Scheme 16>

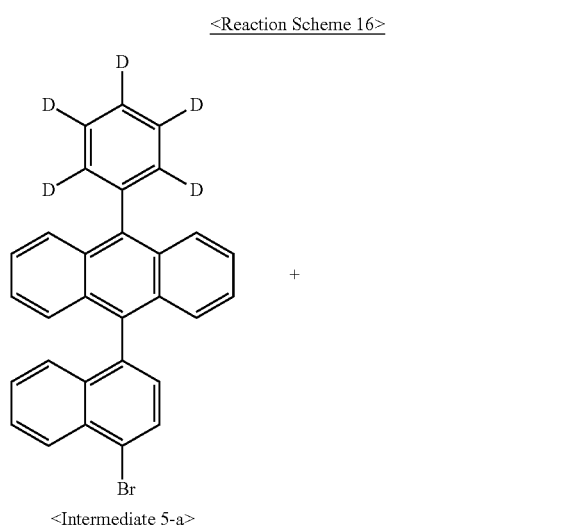

The same procedure was carried out as in Synthesis Example 2-(2), with the exception of using Intermediate 5-a instead of Intermediate 1-a, to afford Compound 52. (4.0 g, 67.4%)

MS: m/z 552.2 [M+]

Synthesis Example 7: Synthesis of Compound 61

Synthesis Example 7-(1): Synthesis of Intermediate 7-a

Intermediate 7-a was synthesized as illustrated in the following Reaction Scheme 17:

<Reaction Scheme 17>

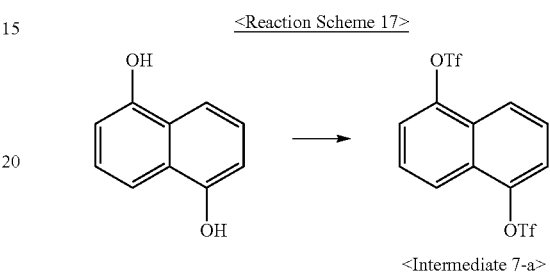

The same procedure was carried out as in Synthesis Example 1-(6), with the exception of using 1,4-dihydroxynaphthalene instead of Intermediate 1-e, to afford Intermediate 7-a. (244 g, 95%)

Synthesis Example 7-(2): Synthesis of Intermediate 7-b

Intermediate 7-b was synthesized as illustrated in the following Reaction Scheme 18:

<Reaction Scheme 18>

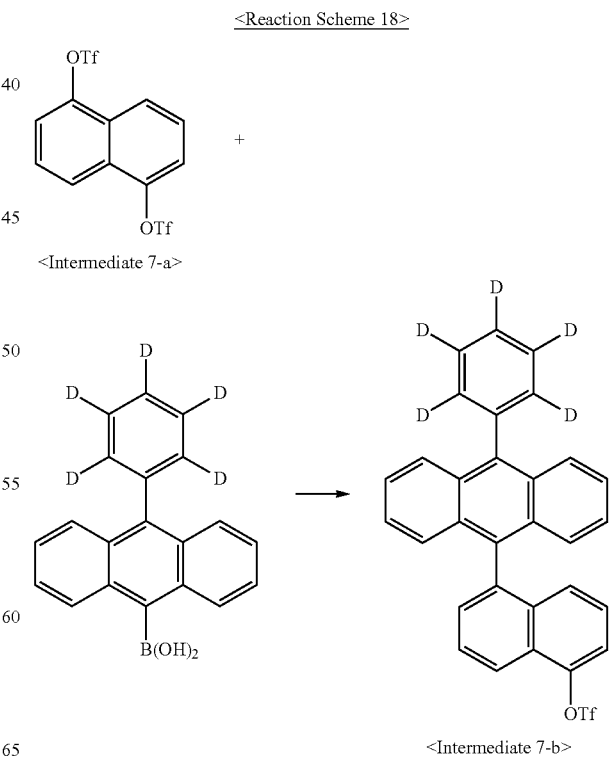

In a 2-L round-bottom flask reactor, Intermediate 7-a (110.0 g, 0.259 mol), 10-phenyl(d5)-anthracene-9-boronic acid (78.6 g, 0.259 mol), tetrakis(triphenylphosphine)palladium (6.0 g, 5 mmol), and potassium carbonate (71.7 g, 0.519 mol) were placed, followed by toluene (770 mL), ethanol (330 mL) and water (220 mL). The mixture was heated to 60° C. and stirred for 1 hr. After completion of the reaction, the reaction mixture was cooled to room temperature and the precipitates were filtered off. The filtrate was extracted with water and ethyl acetate and the organic layer was separated and concentrated in a vacuum. The concentrate was dissolved in toluene and recrystallized in methanol to afford Intermediate 7-b. (100.0 g, 72.3%)

Synthesis Example 7-(3): Synthesis of Compound 61

Compound 61 was synthesized as illustrated in the following Reaction Scheme 19:

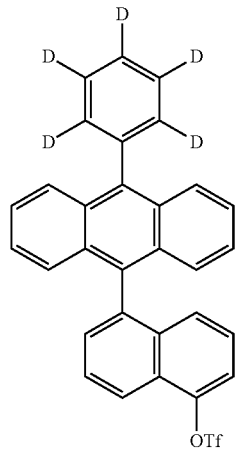

<Reaction Scheme 19>

<Compound 61>

The same procedure was carried out as in Synthesis Example 1-(8), with the exception of using Intermediate 7-b instead of Intermediate 1-a, to afford Compound 61. (2.8 g, 54%)

MS: m/z 552.2 [M+]

Synthesis Example 8: Synthesis of Compound 70

Synthesis Example 8-(1): Synthesis of Compound 70

Compound 70 was synthesized as illustrated in the following Reaction Scheme 20:

<Reaction Scheme 20>

-continued

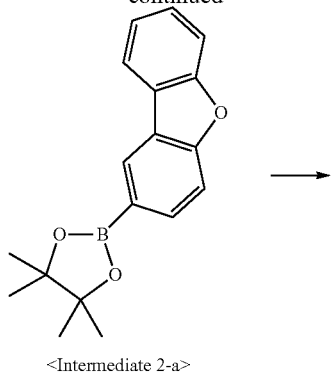

<Intermediate 2-a>

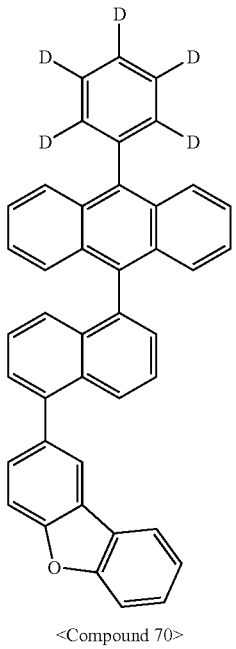

<Compound 70>

The same procedure was carried out as in Synthesis Example 2-(2), with the exception of using Intermediate 7-b instead of Intermediate 1-a, to afford Compound 70. (2.4 g, 46%).

MS: m/z 552.2 [M+]

Synthesis Example 9: Synthesis of Compound 118

Synthesis Example 9-(1): Synthesis of Compound 118

Compound 118 was synthesized as illustrated in the following Reaction Scheme 21:

<Reaction Scheme 21>

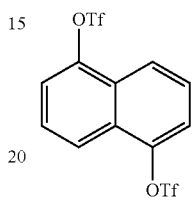 + 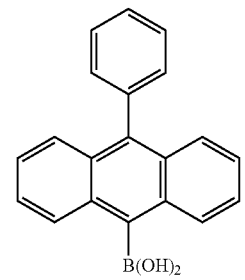 →

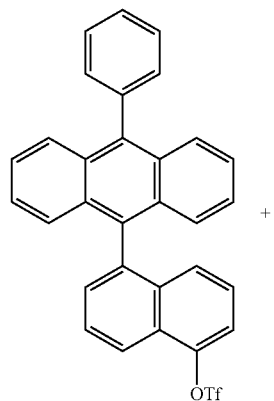 +

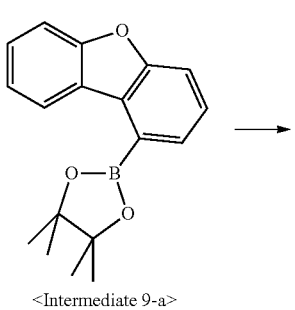

<Intermediate 9-a>

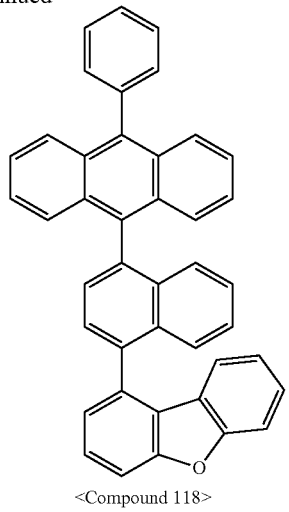
<Compound 118>

The same procedure was carried out as in Synthesis Examples 7-(2) and 7-(3), with the exception of using 10-phenyl(H5)-anthracene-9-boronic acid and Intermediate 9-a instead of 10-phenyl(d5)-anthracene-9-boronic acid and Intermediate 7-b, respectively, to afford Compound 118. (3.5 g, 58%)

MS: m/z 547.2 [M+]

Examples 1-7: Fabrication of OLEDs

An ITO glass substrate was patterned to have a translucent area of 2 mm×2 mm and cleansed. The ITO glass was mounted in a vacuum chamber that was then set to have a base pressure of 1×10$^{-7}$ torr. On the ITO glass substrate, films were formed of HAT-CN (50 Å) and α-NPD (600 Å) in that order. A light-emitting layer (200 Å) was formed of a mixture including each of the compounds shown in Table 1 and BD1 (5 wt %). Then, [Chemical Formula E-1] and [Chemical Formula E-2] were deposited at a ratio of 1:1 to form an electron transport layer 300 Å thick, on which an electron injection layer of [Chemical Formula E-1] (10 Å thick) was formed and then covered with an Al layer (1000 Å) to fabricate an organic light-emitting diode. The organic light-emitting diodes thus obtained were measured at 0.4 mA for luminescence properties.

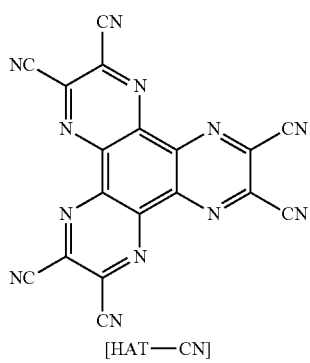
[HAT—CN]

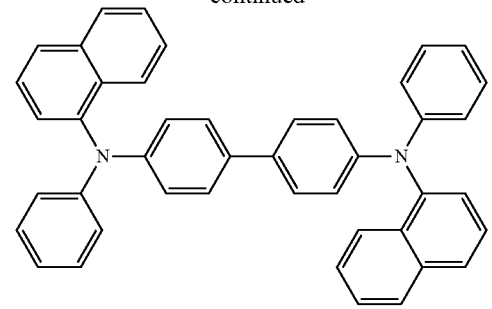
[α-NPD]

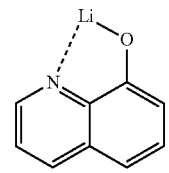
[Chemical FormulaE-1]

[Chemical FormulaE-2]

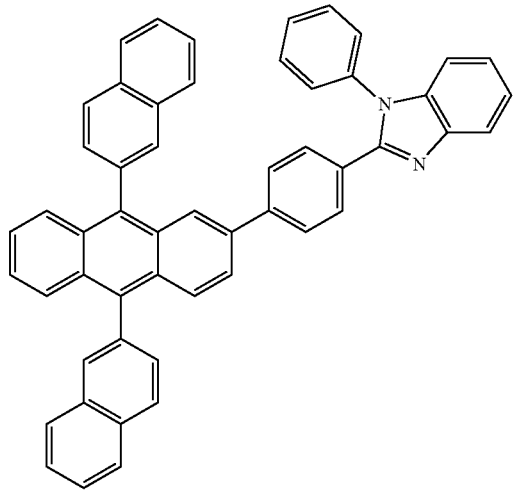
[BD1]

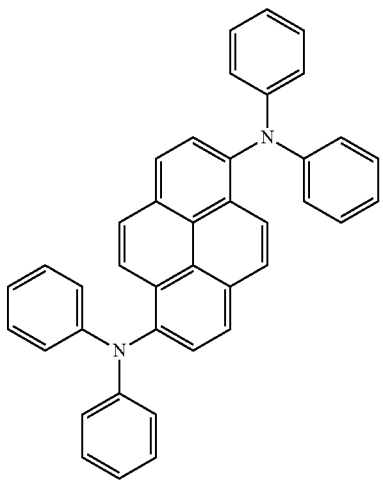

Comparative Examples 1-7

Organic light-emitting diodes were fabricated in the same manner as in Examples 1 to 7, with the exception that [BH1]

to [BH7] were used, instead of the compounds used in Examples 1 to 7. The structures of [BH1] to [BH7] are as follows:
[BH1]
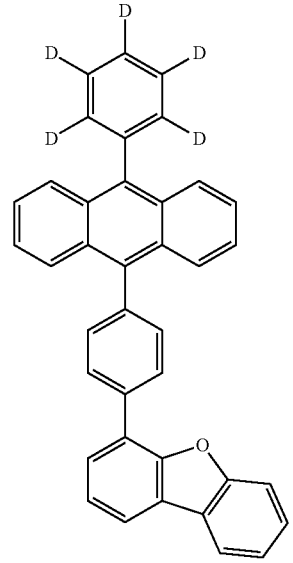
[BH2]
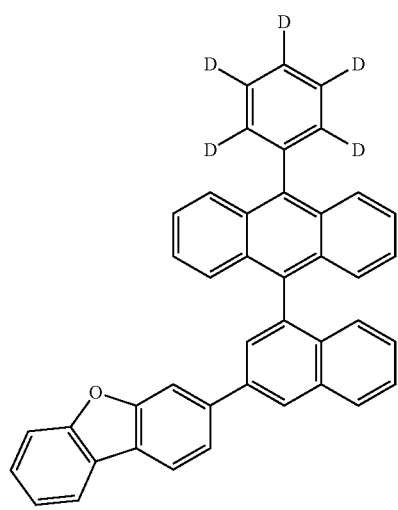
[BH3]
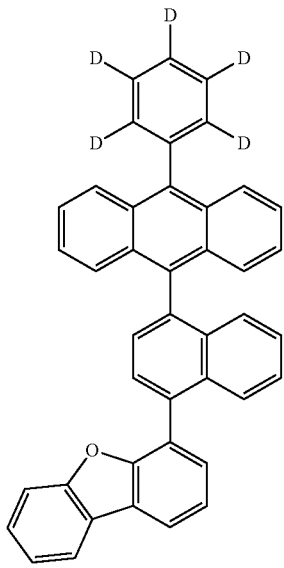
[BH4]
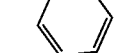

-continued

[BH5]

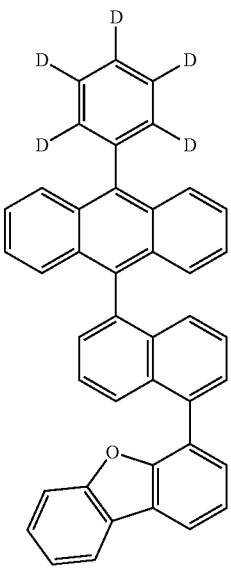

[BH6]

[BH7]

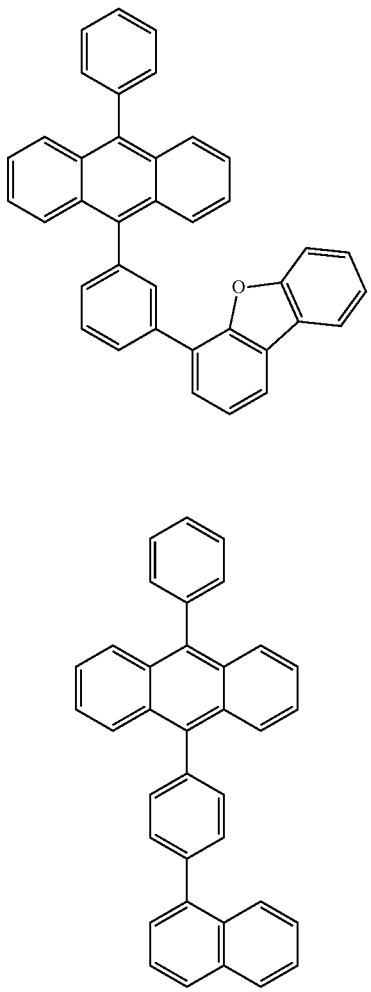

The OLEDs fabricated in Examples 1 to 7 and Comparative Examples 1 to 7 were measured for driving voltage, and the results are summarized in Table 1, below. For voltage, measurement was made at a current density of 10 mA/cm$^2$.

TABLE 1

| Host | | Driving Volt. (V) | ost | | Driving Volt. (V) |
|---|---|---|---|---|---|
| Example 1 | Compound 1 | 3.57 | C. Example 1 | H1 | 3.97 |
| Example 2 | Compound 13 | 3.54 | C. Example 2 | H2 | 3.85 |
| Example 3 | Compound 22 | 3.74 | C. Example 3 | H3 | 3.9 |
| Example 4 | Compound 31 | 3.73 | C. Example 4 | H4 | 3.78 |
| Example 5 | Compound 84 | 3.64 | C. Example 5 | H5 | 3.8 |
| Example 6 | Compound 52 | 3.53 | C. Example 6 | H6 | 3.98 |
| Example 7 | Compound 70 | 3.51 | C. Example 7 | H7 | 3.9 |

As is understood from the data of Table 1, the OLEDs using the compounds according to the Examples of the present disclosure operated at lower driving voltages, compared to those using the compounds according to the Comparative Examples.

INDUSTRIAL APPLICABILITY

The present disclosure is industrially applicable as it enables the fabrication of OLEDs that have the diode property of operating at low driving voltages.

The invention claimed is:

1. An organic luminescent compound, represented by the following Chemical Formula A:

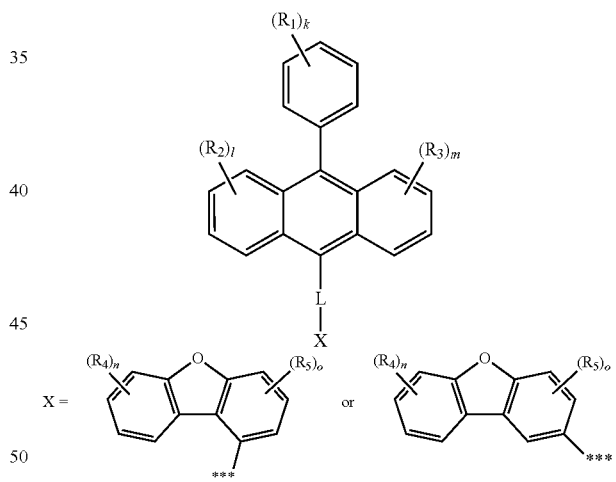

wherein,
R1 to R5 are the same or different and are each independently any one selected from among a hydrogen, a deuterium, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, and a substituted or unsubstituted silyl of 1 to 30 carbon atoms,
wherein each of unsubstituted carbon atoms of R1 to R5 is bound with a hydrogen atom or a deuterium atom,
linker L is a single bond, or a substituted or unsubstituted arylene of 6 to 60 carbon atoms;

k is an integer of 1 to 5, l to n are the same or different and are each independently an integer of 1 to 4, o is an integer of 1 to 3, with the proviso that when k to o are each an integer of 2 or greater, corresponding R1's to R5's are individually the same or different, and "***" of X denotes a bonding site to be linked to linker L, wherein R1 in Chemical Formula A is a deuterium and k is 5, or R4 and/or R5 in Chemical Formula A is a deuterium, and n is 2 or greater, or o is 2 or greater, wherein the term 'substituted' in the expression 'substituted or unsubstituted' used in Chemical Formula A means having at least one substituent selected from the group consisting of a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 7 to 24 carbon atoms, an alkylsilyl of 1 to 24 carbon atoms, and an arylsilyl of 6 to 24 carbon atoms.

2. The organic luminescent compound as set forth in claim 1, wherein the linker L is a single bond or one selected from among compounds represented by the following Structural Formulas 1 and 2:

[Structural Formula 1]

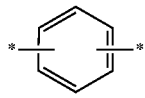

[Structural Formula 2]

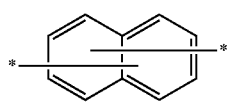

wherein each of the unsubstituted carbon atoms of the aromatic ring moiety may be bound with a hydrogen atom or a deuterium atom.

3. The organic luminescent compound as set forth in claim 1, wherein R2 and/or R3 is a deuterium, and l is 2 or greater, or m is 2 or greater.

4. The organic luminescent compound as set forth in claim 1, wherein the organic luminescent compound is any one selected from among compounds represented by the following Chemical Formulas 1 to 99, 130 to 132, 134, 136, and 138:

<Compound 1>

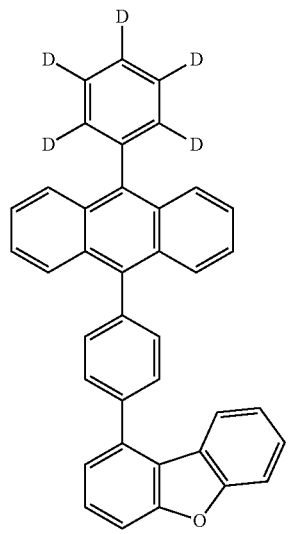

<Compound 2>

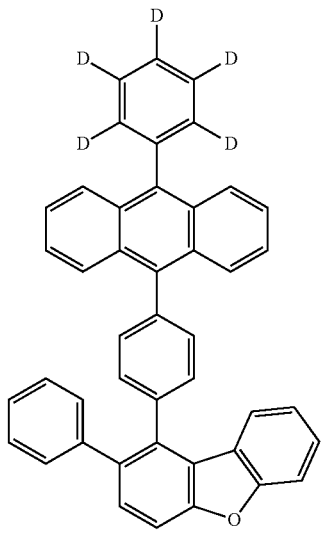

<Compound 3>

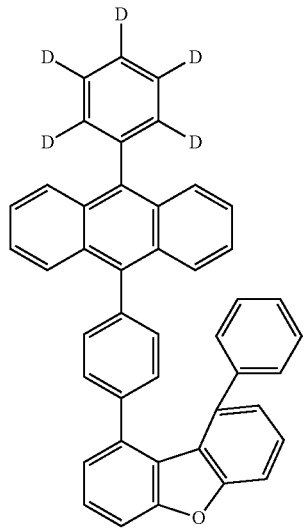

<Compound 4>
<Compound 5>
<Compound 6>
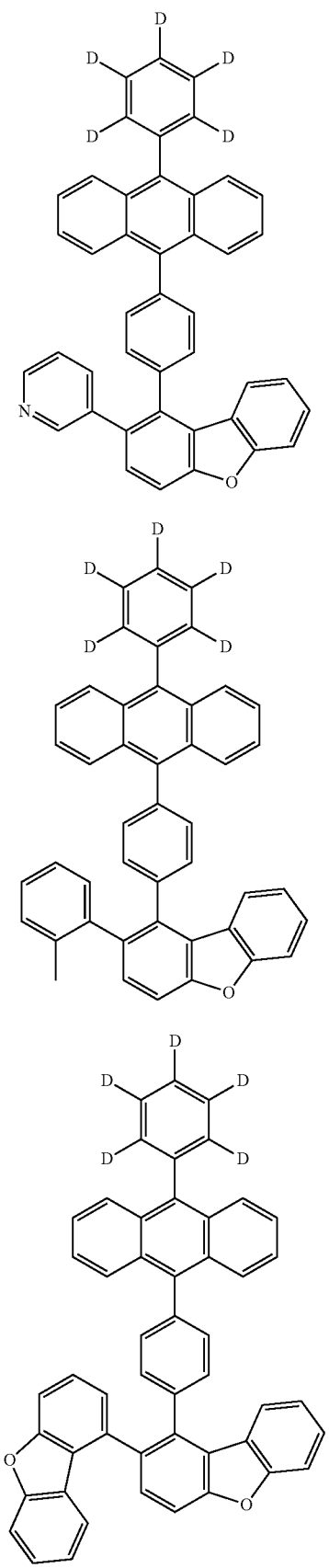
<Compound 7>
<Compound 8>
<Compound 9>
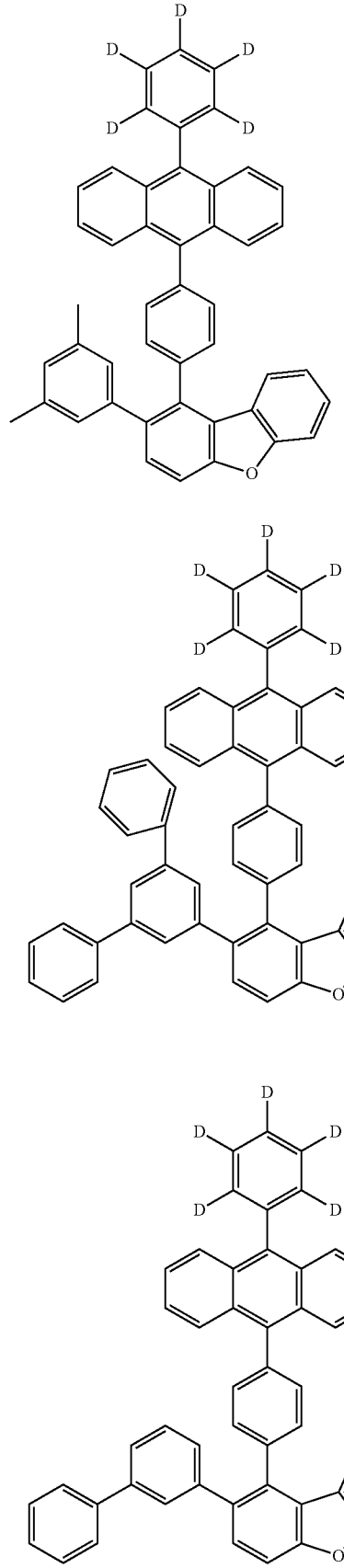

<Compound 10>
<Compound 11>
<Compound 12>
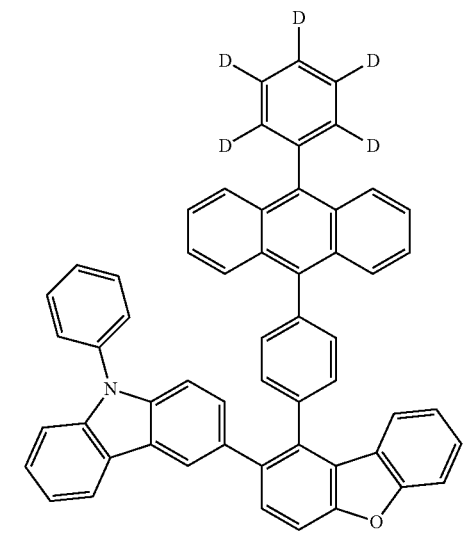
<Compound 13>
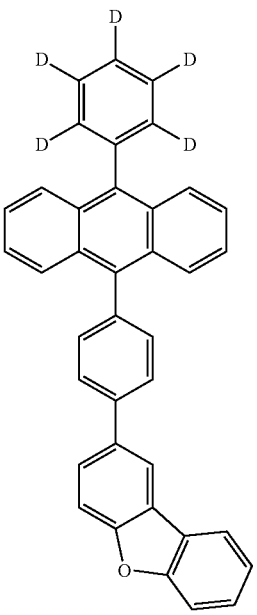
<Compound 14>
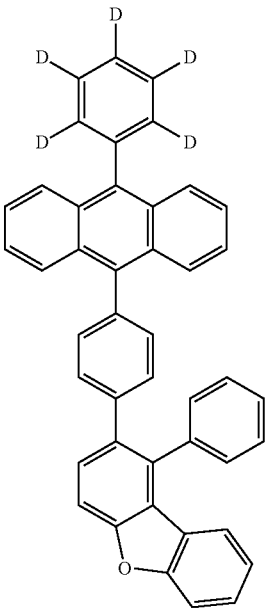

<Compound 15>
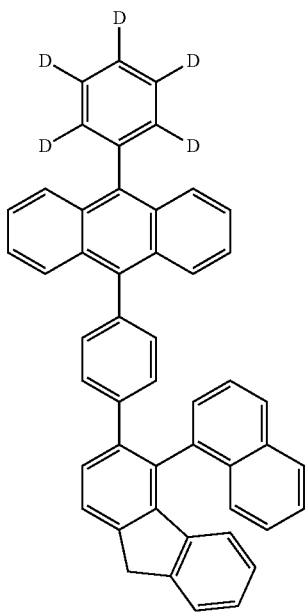
<Compound 17>
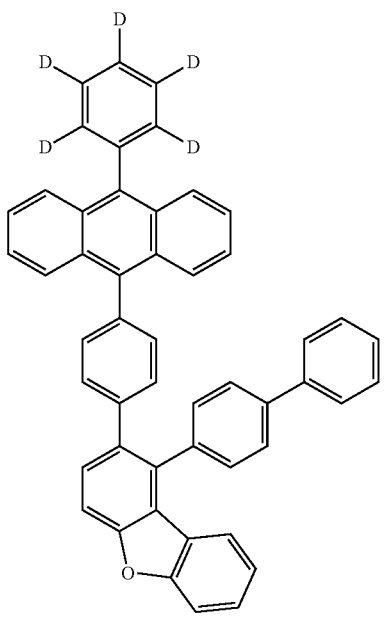
<Compound 16>
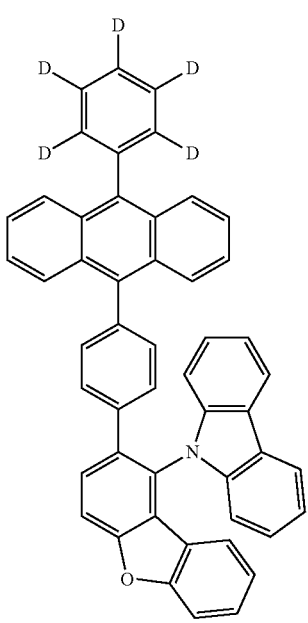
<Compound 18>
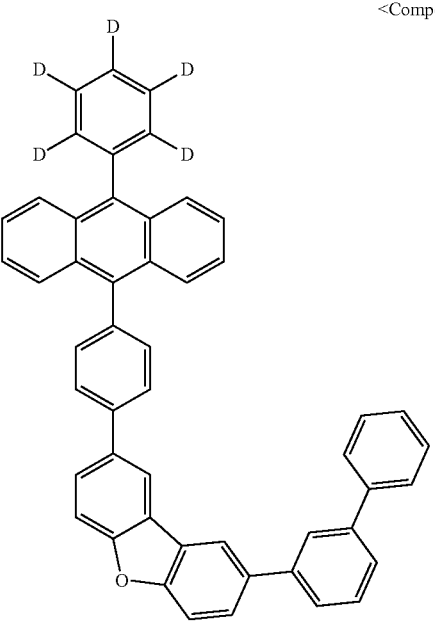

<Compound 19>
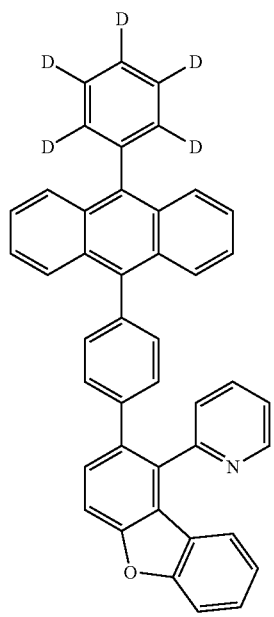
<Compound 20>
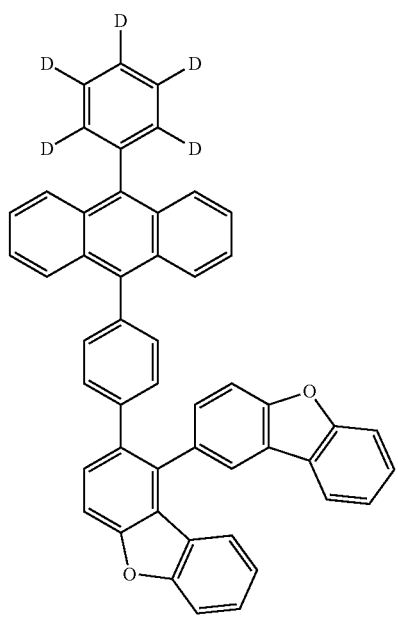
<Compound 21>
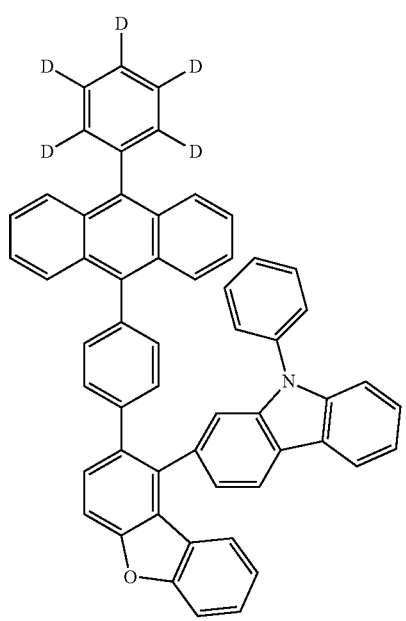
<Compound 22>
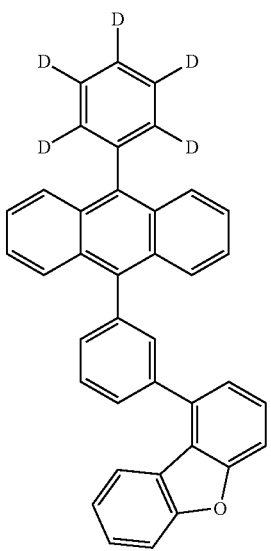

<Compound 23>
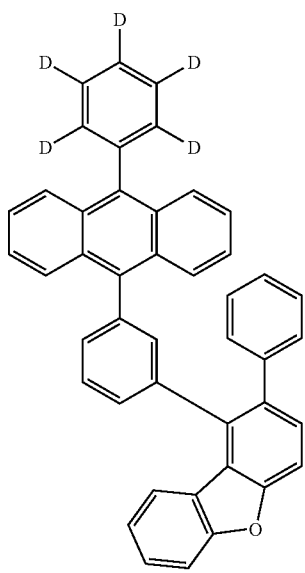
<Compound 24>
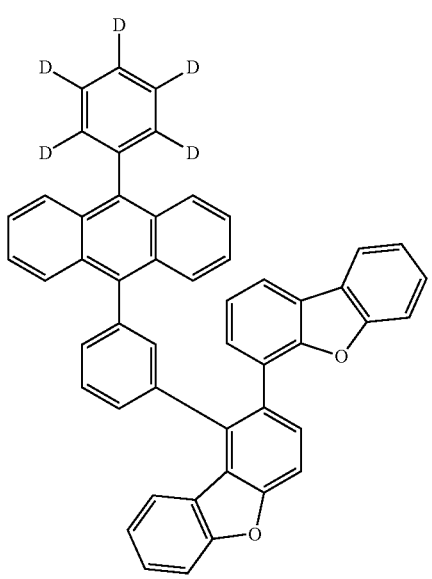
<Compound 25>
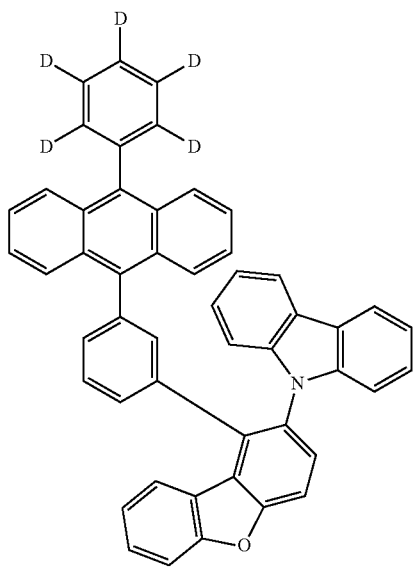
<Compound 26>
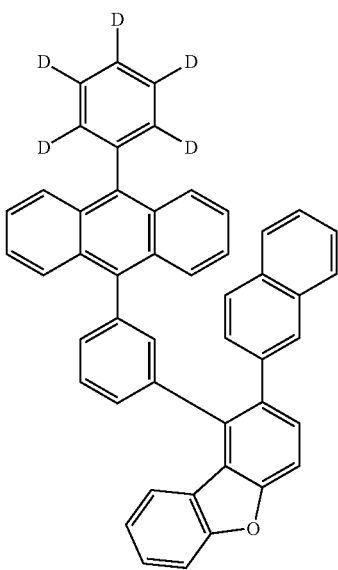

<Compound 27>
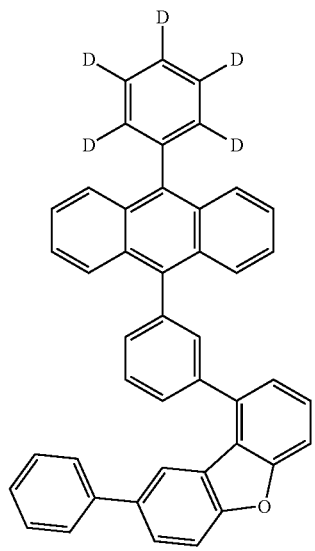
<Compound 29>
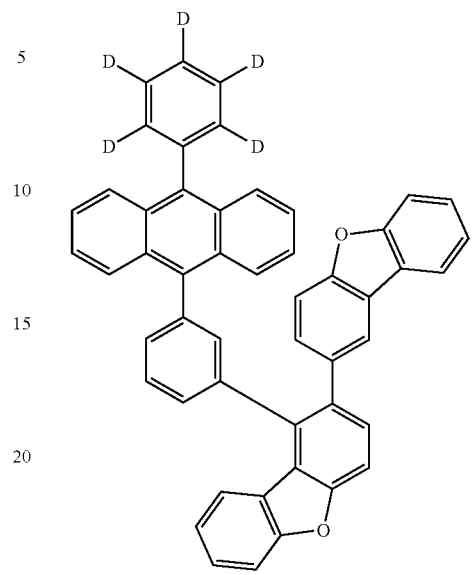
<Compound 28>
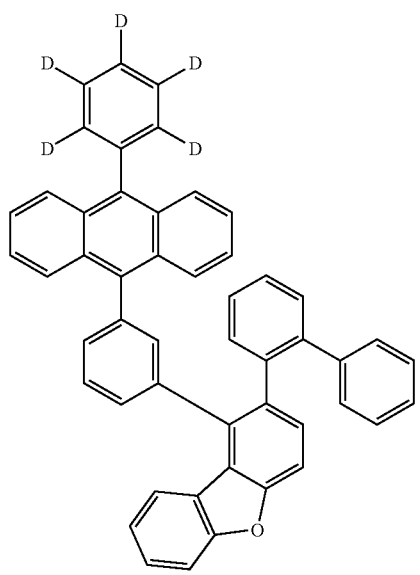
<Compound 30>
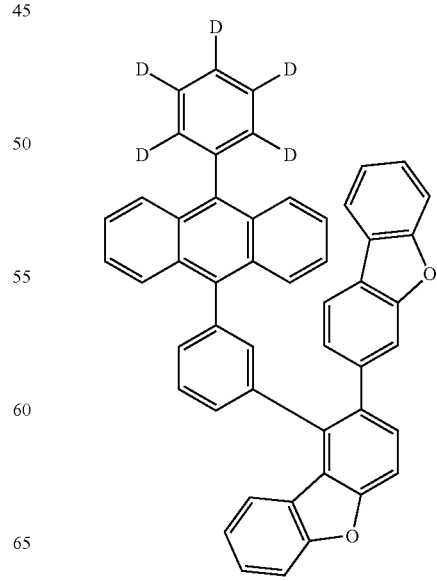

<Compound 31>
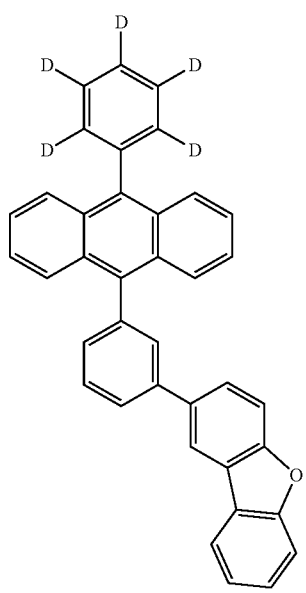
<Compound 32>
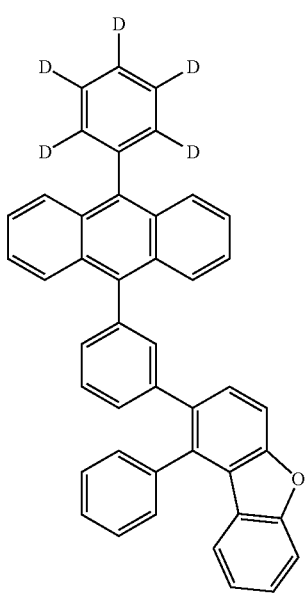
<Compound 33>
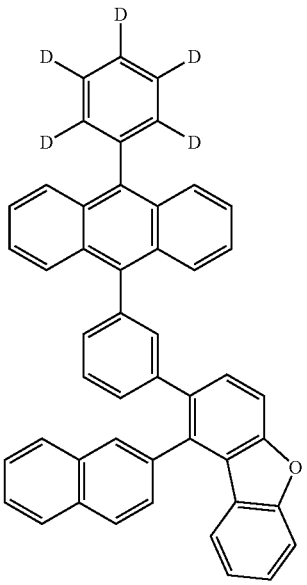
<Compound 34>
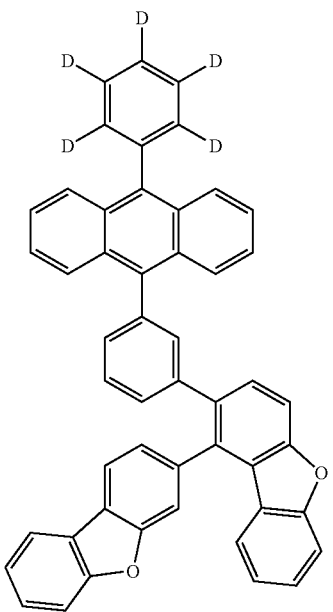

<Compound 35>
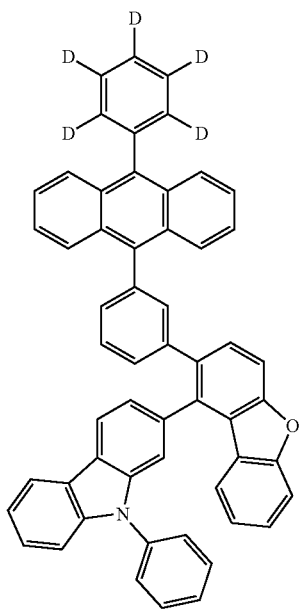
<Compound 36>
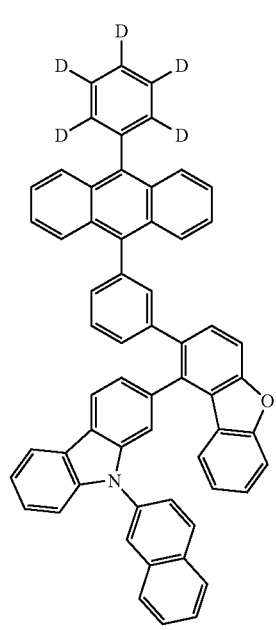
<Compound 37>
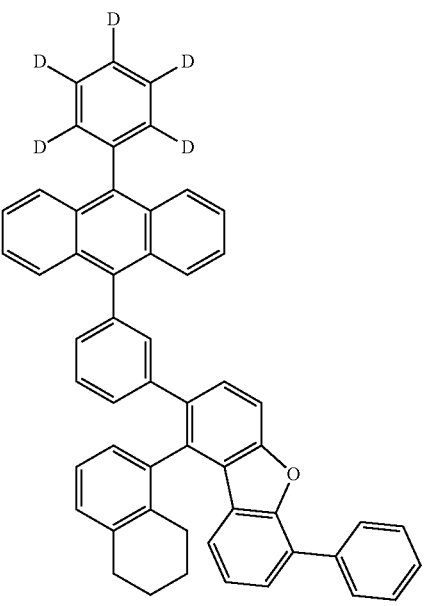
<Compound 38>
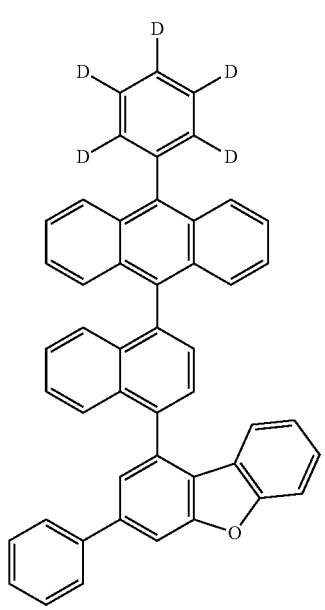

<Compound 39>
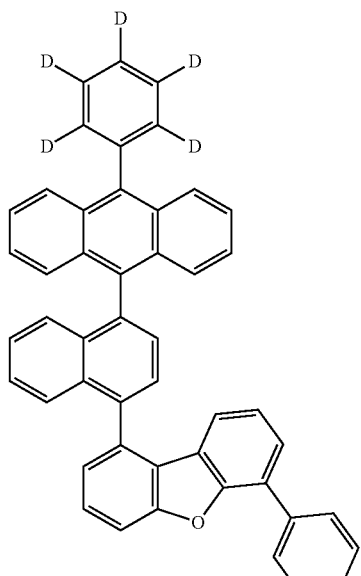
<Compound 40>
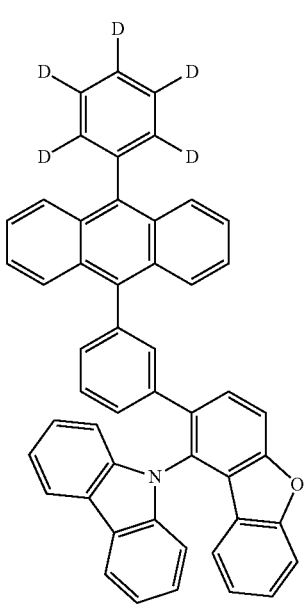
<Compound 41>
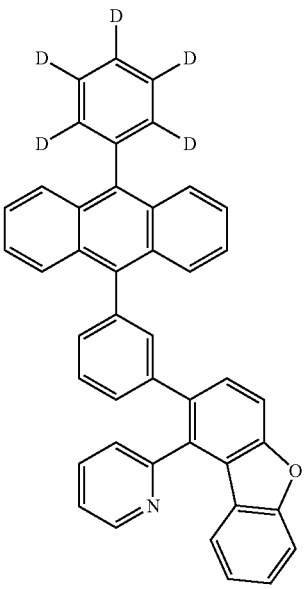
<Compound 42>
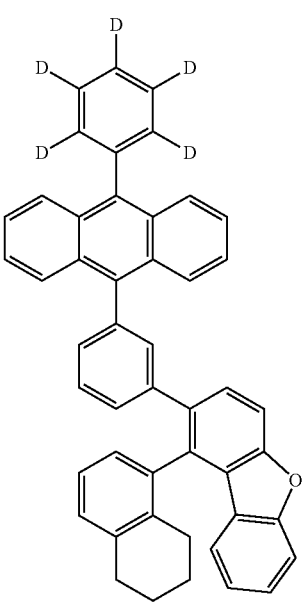

<Compound 43>
<Compound 44>
<Compound 45>
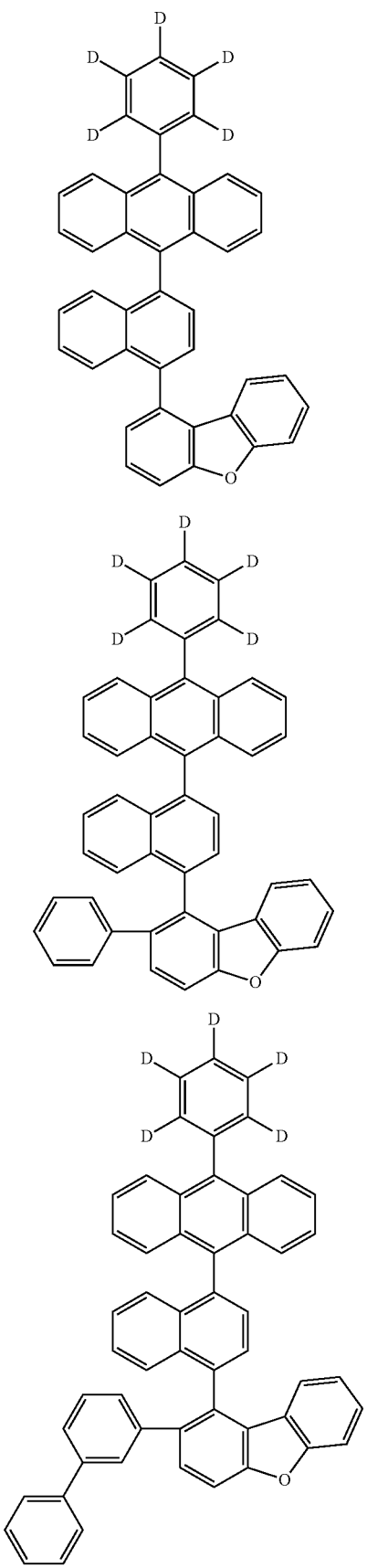
<Compound 46>
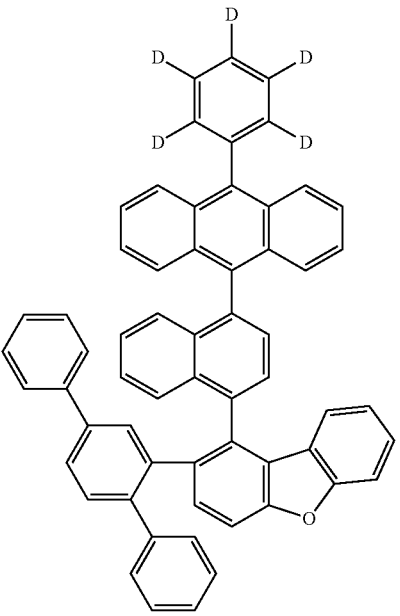
<Compound 47>
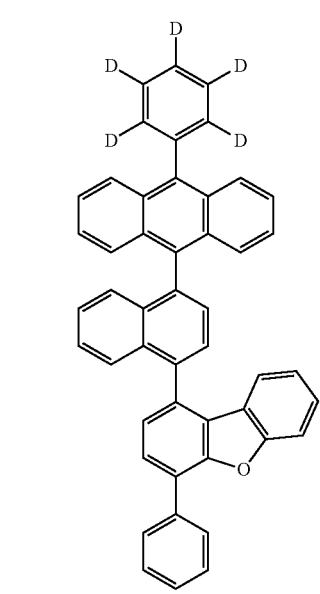

<Compound 48>
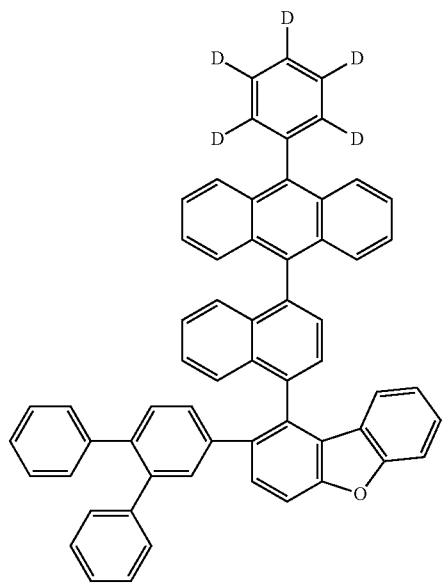
<Compound 49>
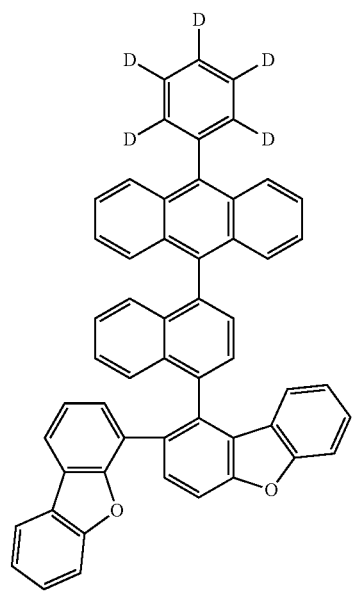
<Compound 50>
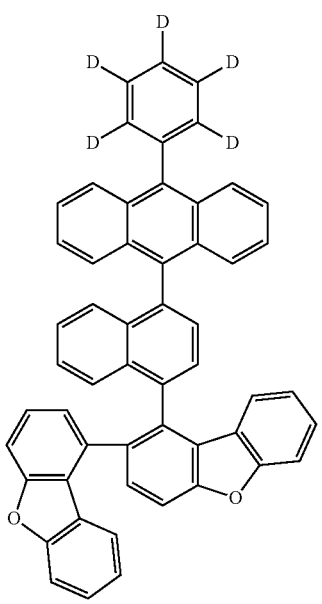
<Compound 51>
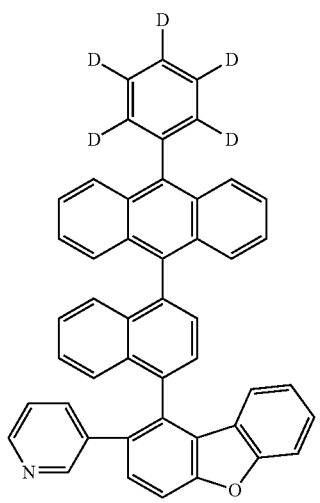

<Compound 52>
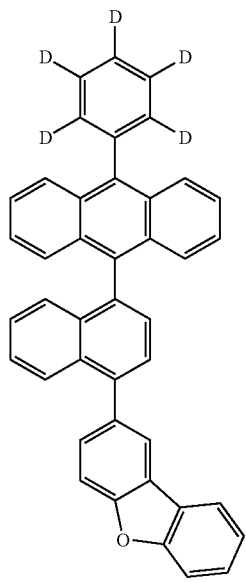
<Compound 53>
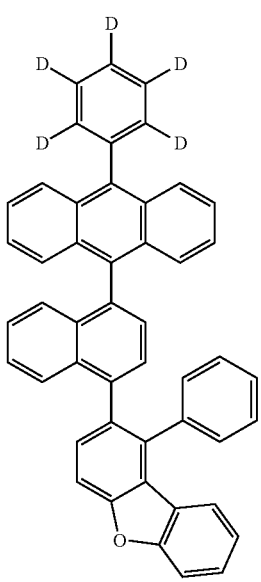
<Compound 54>
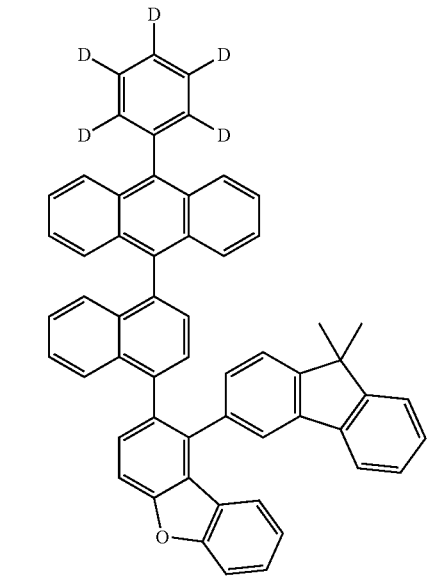
<Compound 55>
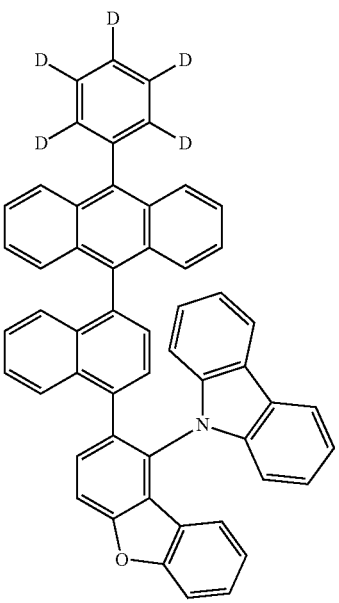

<Compound 56>
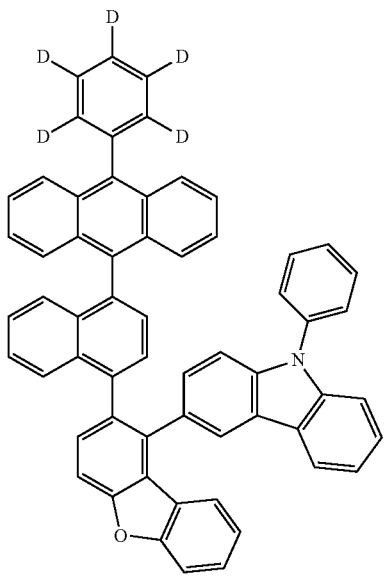
<Compound 58>
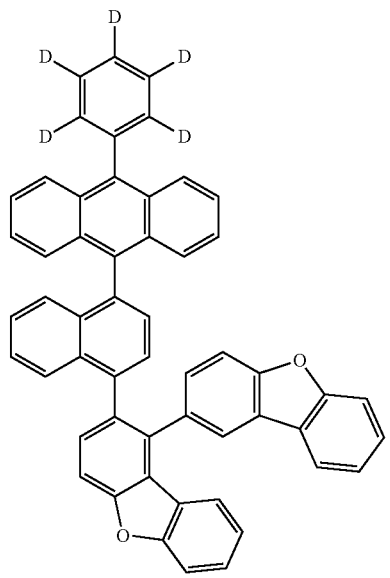
<Compound 57>
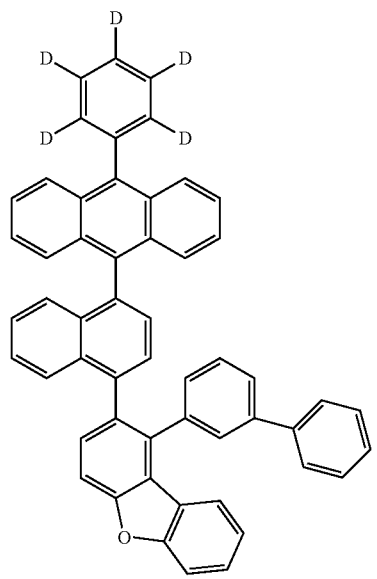
<Compound 59>
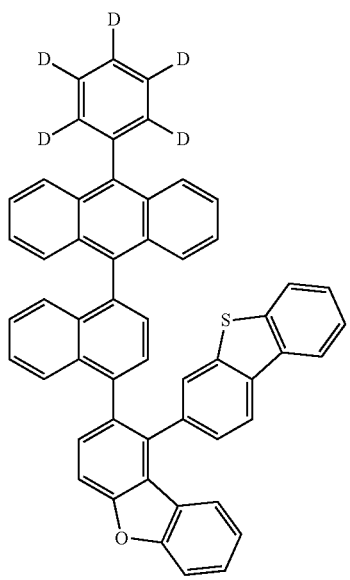

<Compound 60>
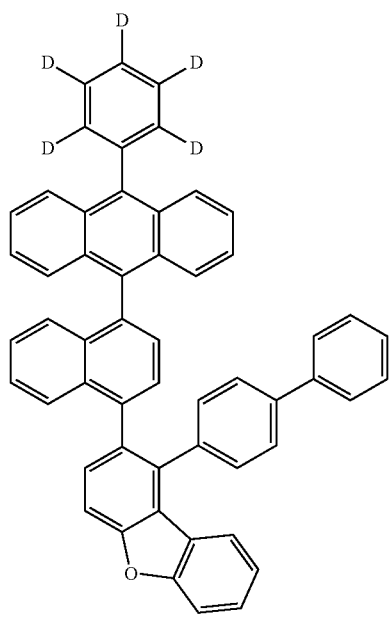
<Compound 61>
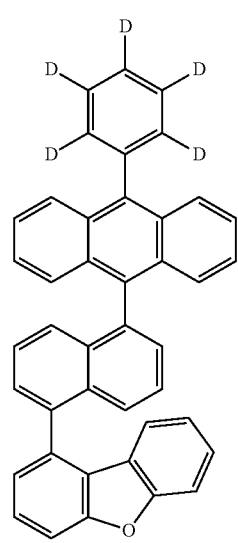
<Compound 62>
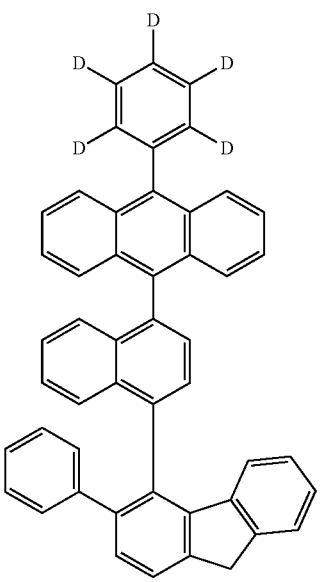
<Compound 63>
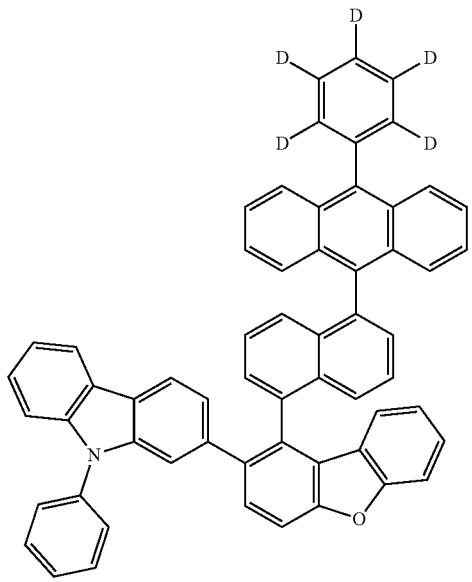

<Compound 64>
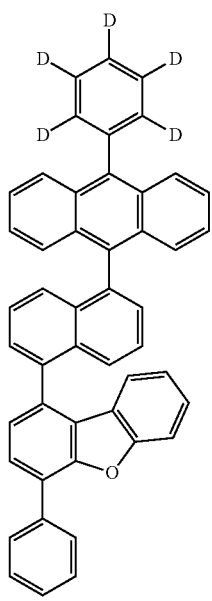
<Compound 65>
<Compound 66>
<Compound 67>
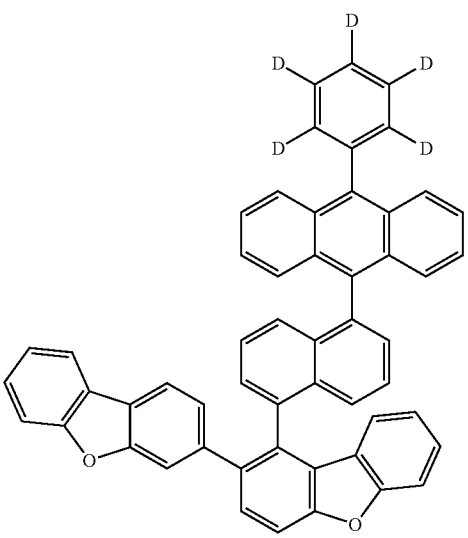
<Compound 68>
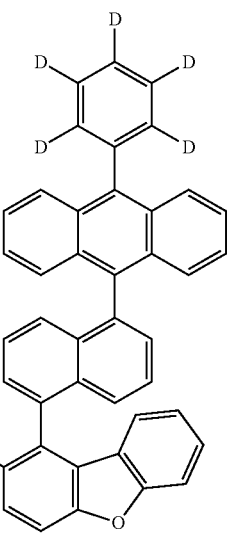

<Compound 69>
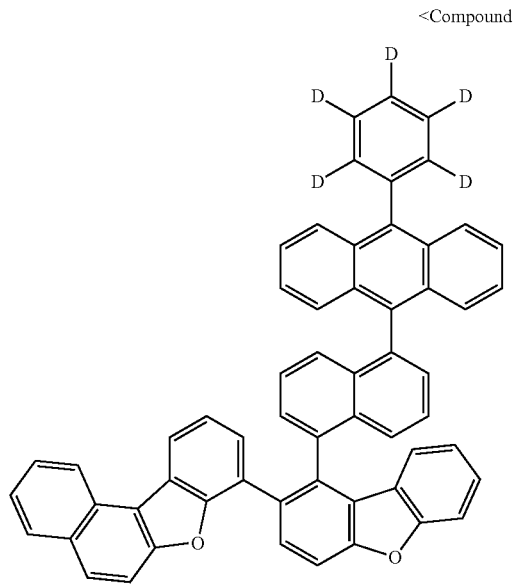
<Compound 71>
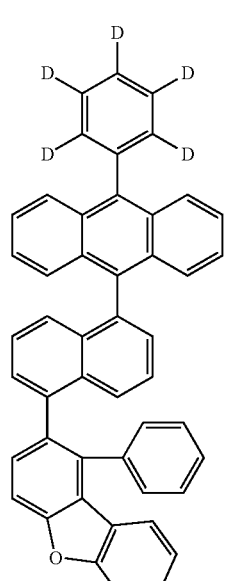
<Compound 70>
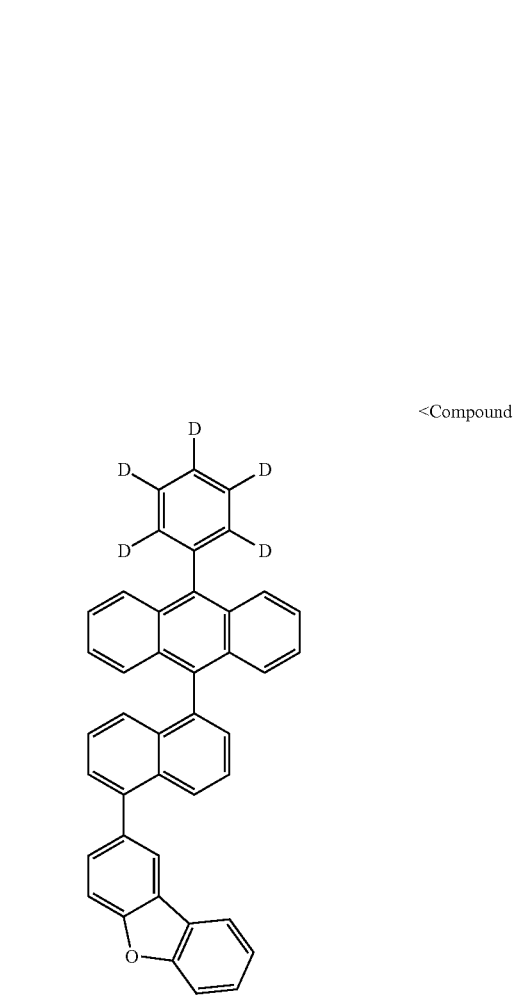
<Compound 72>
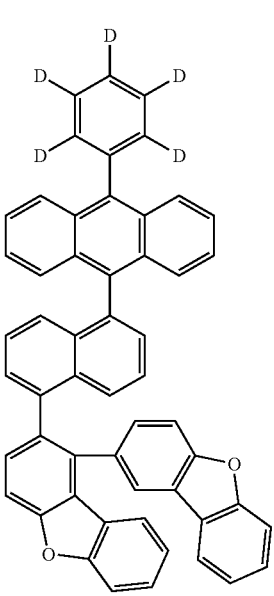

<Compound 73>
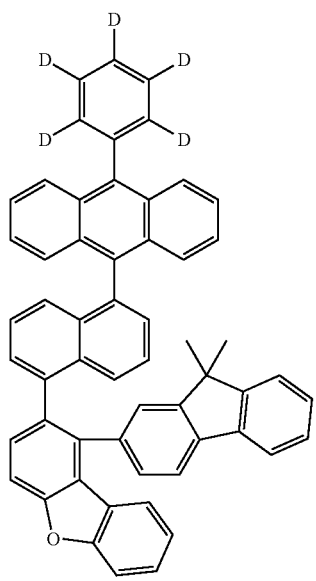
<Compound 74>
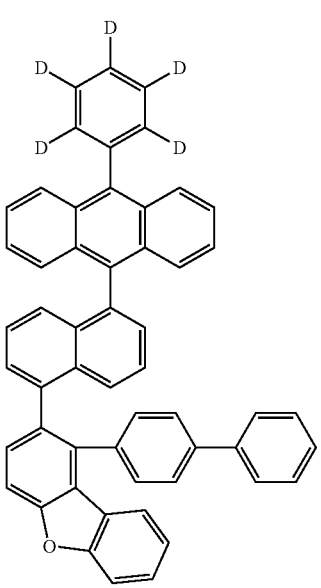
<Compound 75>
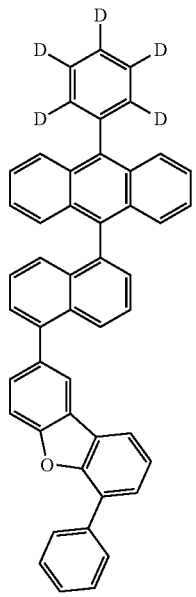
<Compound 76>
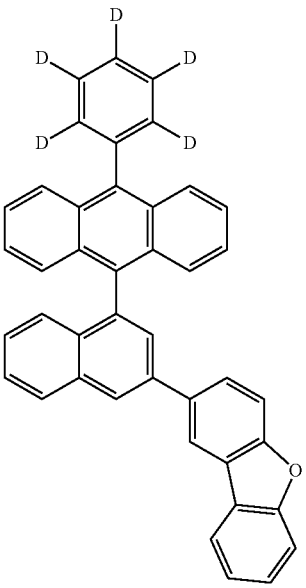

<Compound 77>
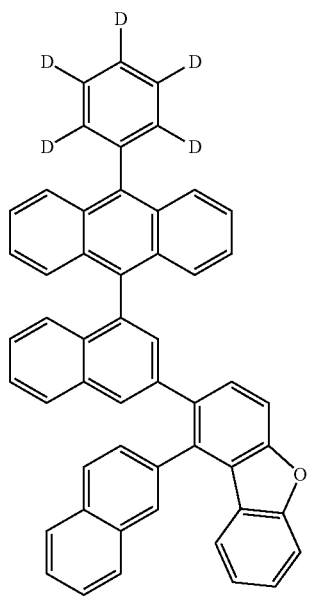
<Compound 78>
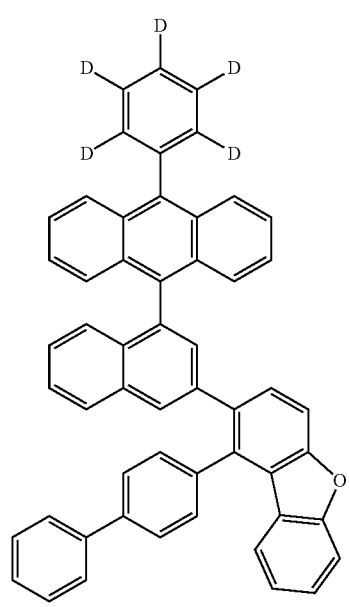
<Compound 79>
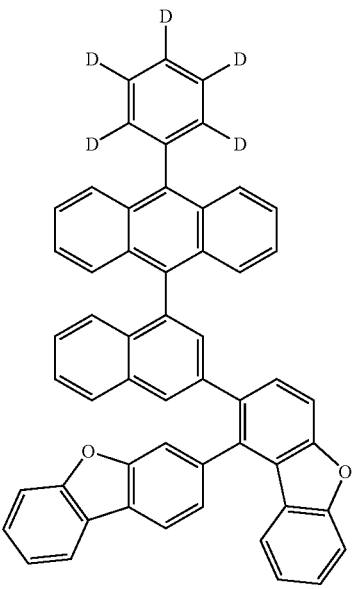
<Compound 80>
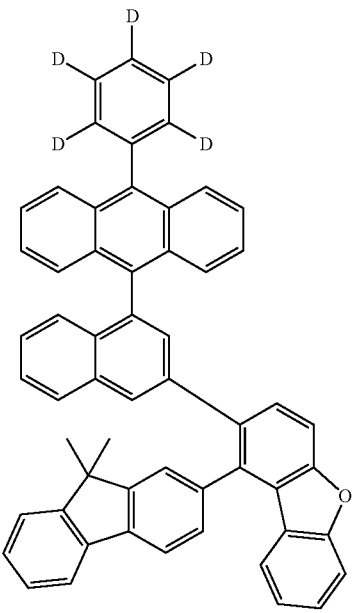

<Compound 81>
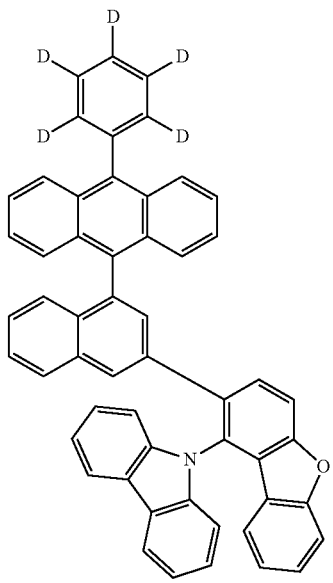
<Compound 82>
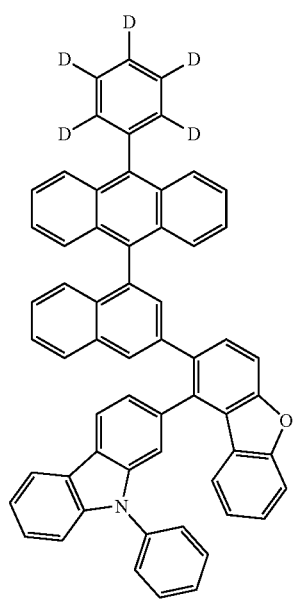
<Compound 83>
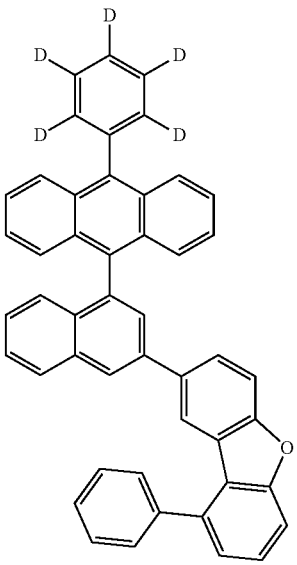
<Compound 84>
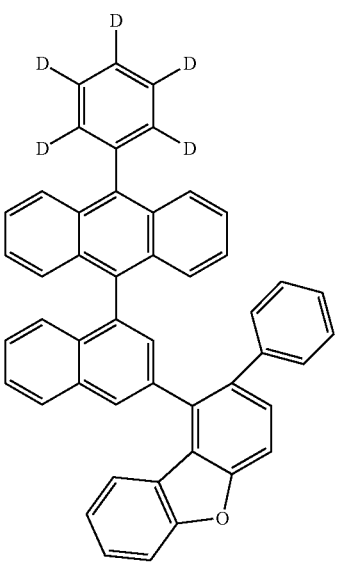
<Compound 85>

<Compound 86>
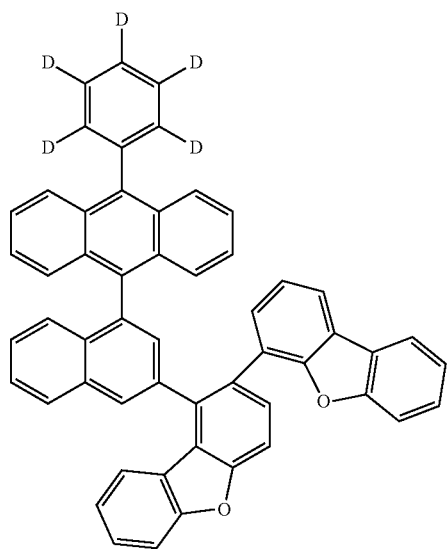
<Compound 88>
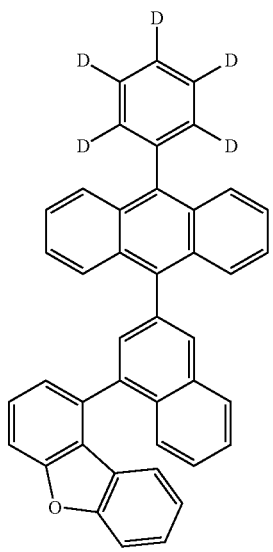
<Compound 87>
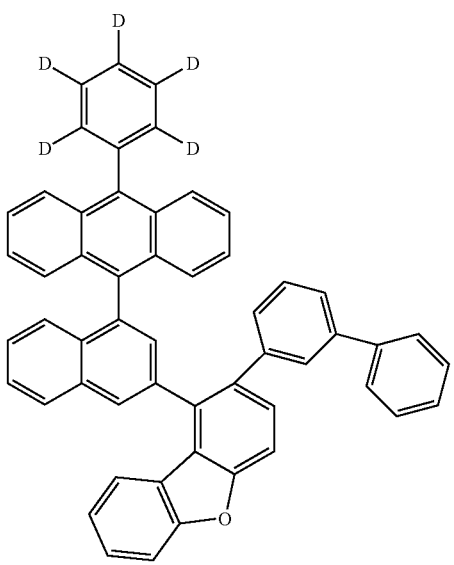
<Compound 89>
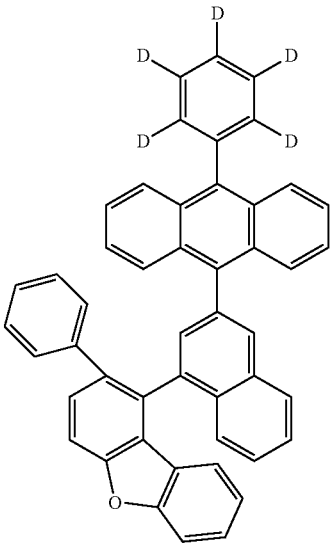

<Compound 90>
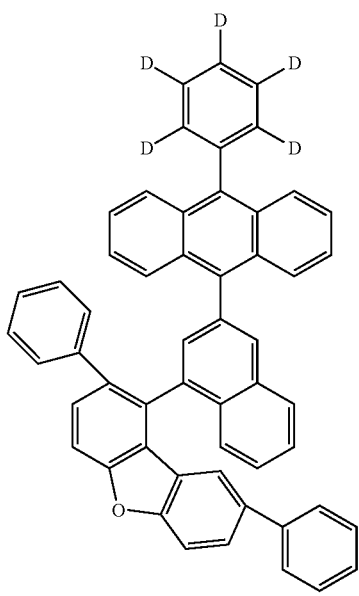
<Compound 91>
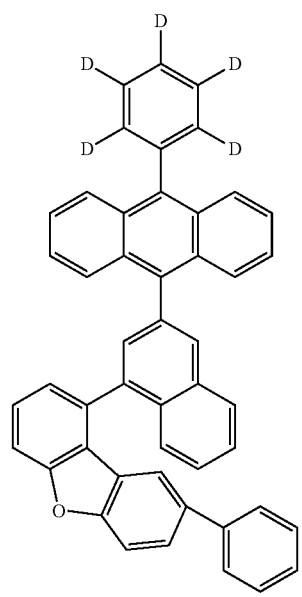
<Compound 92>
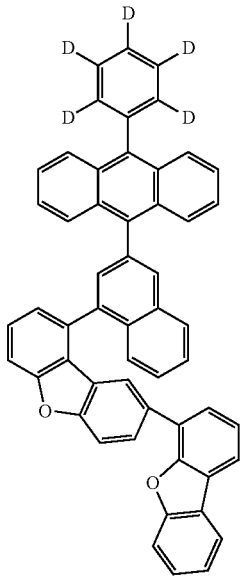
<Compound 93>
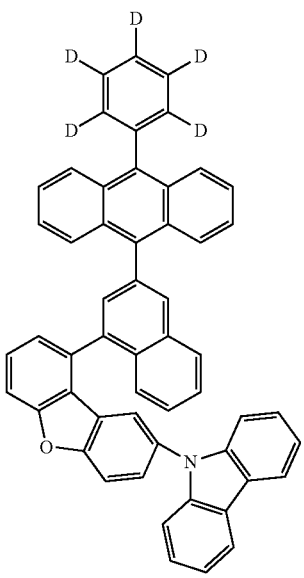

<Compound 94>
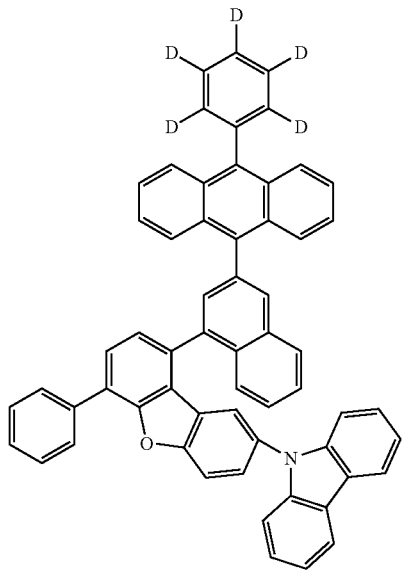
<Compound 95>
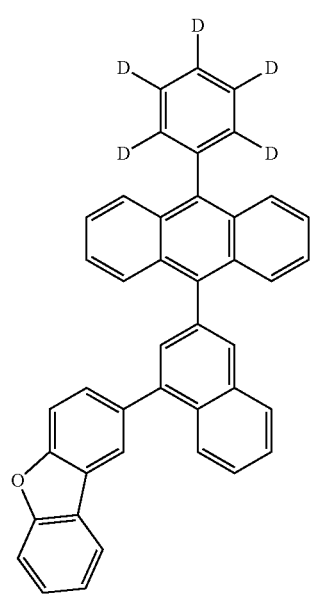
<Compound 96>
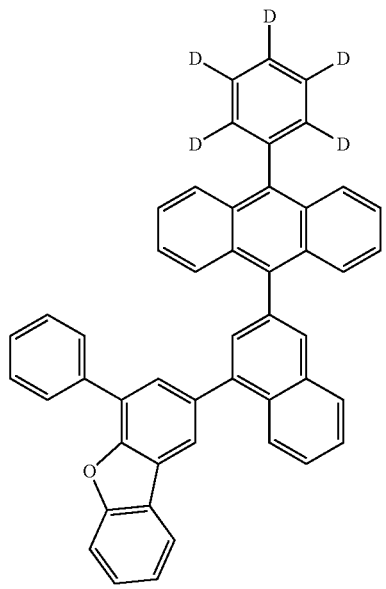
<Compound 97>
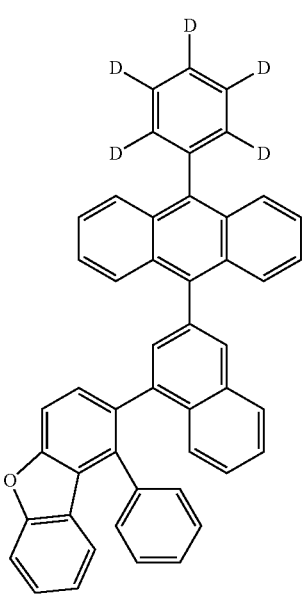

<Compound 98>
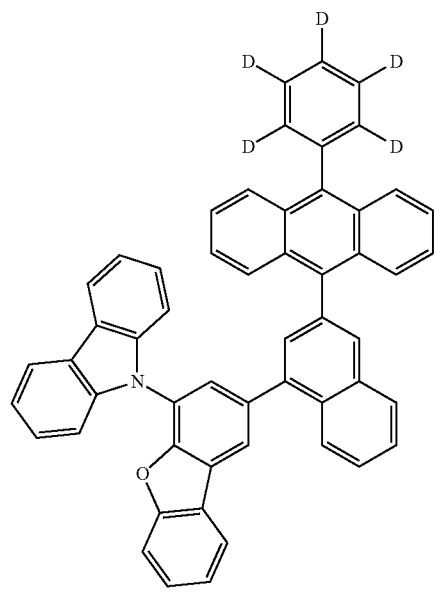
<Compound 130>
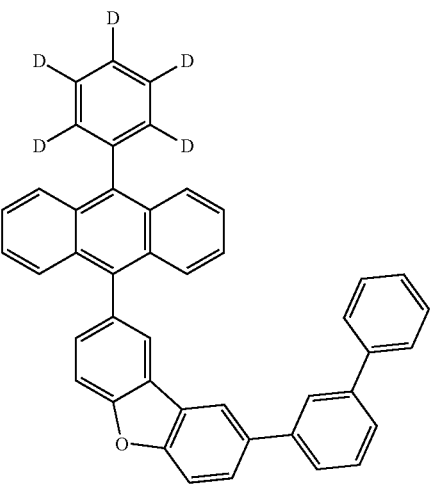
<Compound 131>
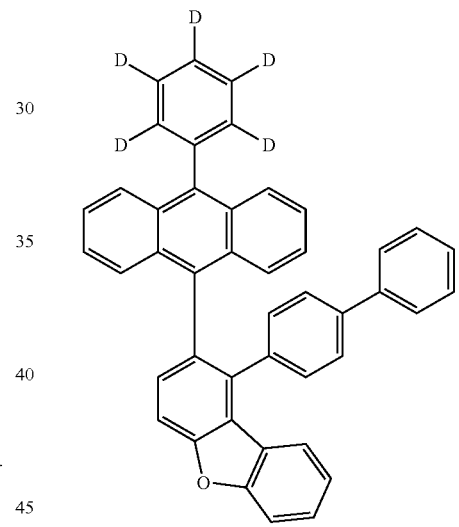
<Compound 99>
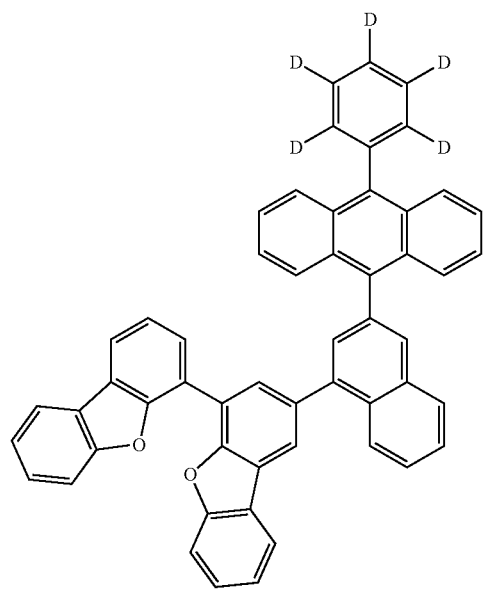
<Compound 132>
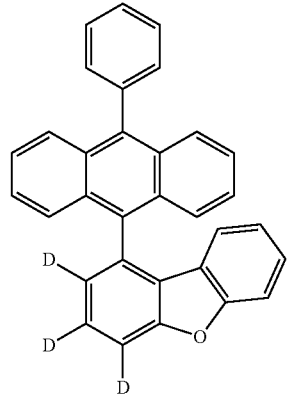

<Compound 134>

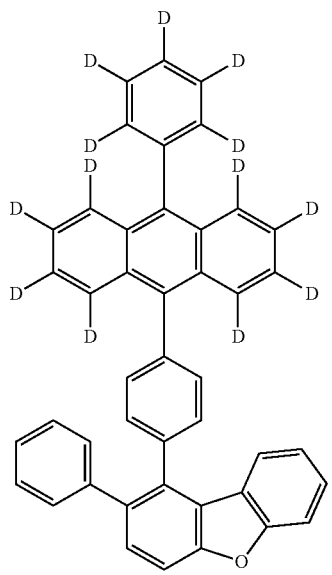

<Compound 136>

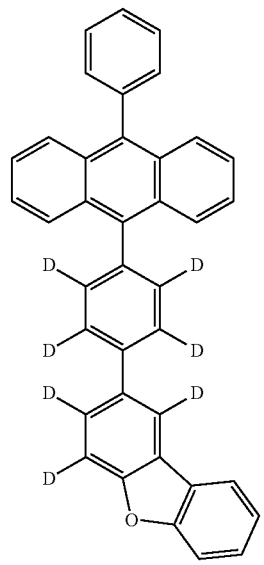

<Compound 138>

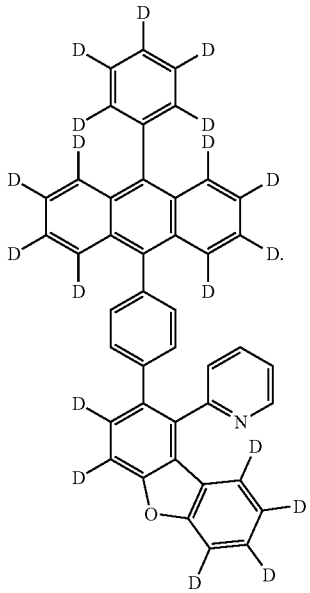

5. An organic light-emitting diode comprising:
a first electrode;
a second electrode facing the first electrode; and
an organic layer interposed therebetween, wherein the organic layer contains at least one organic luminescent compound of any one of claim 1.

6. The organic light-emitting diode as set forth in claim 5, wherein the organic layer comprises at least one of a hole injecting layer, a hole transport layer, a functional layer capable of both hole injection and hole transport, a light-emitting layer, an electron transport layer, and an electron injecting layer.

7. The organic light-emitting diode as set forth in claim 6, wherein the organic layer interposed between the first electrode and the second electrode is a light-emitting layer composed of a host and a dopant, the organic luminescent compound serving as the host.

8. The organic light-emitting diode as set forth in claim 6, wherein at least one selected from among the layers is deposited using a single-molecule deposition process or a solution process.

9. The organic light-emitting diode as set forth in claim 5, wherein the organic light-emitting diode is used for a device selected from among a flat display device, a flexible display device, a monochrome or grayscale flat illumination device, and a monochrome or grayscale flexible illumination device.

\* \* \* \* \*